US007429596B2

(12) United States Patent
Tanaka et al.

(10) Patent No.: US 7,429,596 B2
(45) Date of Patent: Sep. 30, 2008

(54) 1H-PYRROLO [2,3-D] PYRIMIDINE DERIVATIVES AND METHODS OF USE THEREOF

(75) Inventors: Masahiro Tanaka, San Francisco, CA (US); Chao Zhang, San Francisco, CA (US); Kevan M. Shokat, San Francisco, CA (US); Alma L. Burlingame, Sausalito, CA (US); Kirk Hansen, San Mateo, CA (US); Raynard L. Bateman, San Francisco, CA (US); Stephen G. DiMagno, Lincoln, NE (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/871,732

(22) Filed: Jun. 18, 2004

(65) Prior Publication Data

US 2005/0085472 A1 Apr. 21, 2005

Related U.S. Application Data

(60) Provisional application No. 60/480,501, filed on Jun. 20, 2003.

(51) Int. Cl.
| | |
|---|---|
| *C07D 487/04* | (2006.01) |
| *C07D 413/06* | (2006.01) |
| *A61K 31/519* | (2006.01) |
| *A61K 31/675* | (2006.01) |
| *A61K 31/662* | (2006.01) |
| *A61K 31/497* | (2006.01) |
| *A61K 31/5355* | (2006.01) |
| *C07F 9/38* | (2006.01) |
| *A61P 35/04* | (2006.01) |
| *A61P 35/02* | (2006.01) |

(52) U.S. Cl. .................. 514/265.1; 544/280; 544/244; 544/117; 514/81; 514/252.16; 514/234.5

(58) Field of Classification Search ................ 544/280; 514/265.1

See application file for complete search history.

(56) References Cited

U.S. PATENT DOCUMENTS

| 5,593,997 | A | | 1/1997 | Dow et al. ............... 514/262.1 |
| 6,001,839 | A | * | 12/1999 | Calderwood et al. ...... 514/265.1 |
| 6,383,790 | B1 | | 5/2002 | Shokat ..................... 435/194 |
| 6,921,763 | B2 | | 7/2005 | Hirst et al. .................. 514/258 |
| 2006/0235031 | A1 | | 10/2006 | Arnold et al. ............. 514/263.2 |

FOREIGN PATENT DOCUMENTS

| GB | 812366 | | 4/1959 |
| WO | WO 93/22443 | | 11/1993 |
| WO | WO 97/28161 A1 | * | 8/1997 |
| WO | WO 98/41525 | * | 9/1998 |
| WO | WO 98/41525 A1 | * | 9/1998 |
| WO | WO 00/17202 A1 | * | 3/2000 |
| WO | 01/19829 A2 | | 3/2001 |
| WO | 03/020880 A2 | | 3/2003 |
| WO | WO 2005/097800 | | 10/2005 |

OTHER PUBLICATIONS

Widler, L.; Green, J.; Missbach, M.; Susa, M.; Altmann, E., Bioorganic & Medicinal Chemistry Letters, 11(6), 849-852 (English) 2001.*

(Continued)

*Primary Examiner*—Brenda Coleman
*Assistant Examiner*—Susanna Moore
(74) *Attorney, Agent, or Firm*—Townsend and Townsend and Crew

(57) ABSTRACT

This invention generally relates to pyrazolo pyrimidine derivatives useful as inhibitors of short chain dehydrogenase/reductase (SDR) family of NAD(P)(H) dependent oxido-reductases. The invention further relates to pharmaceutical compositions and methods of preventing or treating disease with 1H-Pyrrolo[2.3-d]pyrimidine derivatives. More specifically, the invention relates to a 1H-Pyrrolo[2.3-d]pyrimidine which is a compound of Formula I or II:

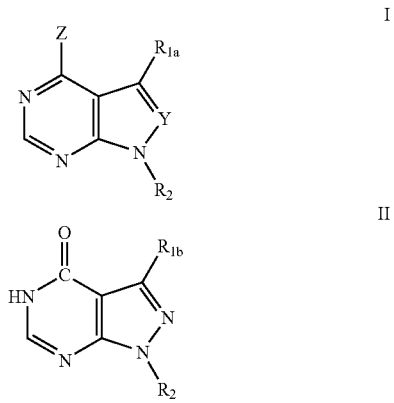

or a pharmaceutically-acceptable salt or prodrug thereof; wherein:

Y is N or $CR_5$;

Z is $NR_3R_4$, halo, H, OH, alkyl, alkyloxy, or haloalkyl; and $R_{1a}$ is indolyl, thiazolyl, benzyl, biphenylyl, thiophenyl, pyrrolyl, or phenyl, wherein said phenyl is substituted with at least one of OH, $-NR_3R_4$, $-C(=O)NR_6R_7$, $-CN$, $NO_2-C(=O)OH$, $-C(=O)O$-alkyl, $(C_1-C_4)$alkyl, halo, haloalkyl or haloaryl; and wherein said indolyl, thiazolyl, benzyl, biphenylyl, thiophenyl, or pyrrolyl is optionally substituted with OH, $-NR_3R_4$, $-C(=O)NR_6R_7$, $-CN$, $NO_2$, $-C(=O)O-R_3$, $(C_1-C_4)$alkyl, halo, haloalkyl or haloaryl.

14 Claims, 39 Drawing Sheets

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, p. 451 and 596.*
Norio Miyaura and Akira Suzuki, Chem. Rev. 95(7) 1995, pp. 2457-2483.*
Frazen, Robert, Can J. Chem., 78, 957-962 (2000).*
Arnold et. al. (Bioorg. & Med. Chem. Lett., 2000; 10; 2167-2170).*
Niswender, C. M. et al., "Protein Engineering of Protein Kinase A Catalytic Subunits Results in the Acquisition of Novel Inhibitor Sensitivity," *The Journal of Biological Chemistry*, Aug. 9, 2002, 277(32), 28916-28922.
Andrews, R.C. et al., "Effects of the 11β-Hydroxysteroid Dehydrogenase Inhibitor Carbenoxolone on Insulin Sensitivity in Men with Type 2 Diabetes," *J. Clin. Endocrinol. Metab.*, 2003, 88(1), 285-291.
Barf, T. et al., "Arylsulfonamidothiazoles as a New Class of Potential Antidiabetic Drugs. Discovery of Potent and Selective Inhibitors of the 11β-Hydroxysteroid Dehydrogenase Type 1," *J. Med. Chem.*, 2002, 45(18), 3813-3815.
Barnes, P.J. et al., "Efficacy and Safety of Inhaled Corticosteroids in Asthma," *Am. Rev. Respir. Dis.*, 1993, 148, S1-26.
Bell, G. et al., "Glucokinase Mutations Insulin Secretion, and Diabetes Mellitus," *Annu. Rev. Physiol.*, 1996, 58, 171-186.
Bohren, K.M., et al., "Expression, Crystallization and Preliminary Crystallographic Analysis of Human Carbonyl Reductase," *J. Mol. Biol.*, 1994, 244, 659-664.
Cox, B. et al., "Human Colorectal Cancer Cells Efficiently Conjugate the Cyclopentenone Prostaglandin, Prostaglandin $J_2$ to Glutathione," *Biochim. Biophys. Acta*, 2002, 1584, 37-45.
Diederich, S. et al., "In the Search for Specific Inhibitors of Human 11β-Hydroxysteroid-Dehydrogenases (11β-HSDs): Chenodeoxycholic Acid Selectively Inhibits 11β-HSD-I," *Eur. J. Endocrinol.*, 2000, 142, 200-207.
Ding, S., et al., "A Combinatorial Scaffold Approach toward Kinase-Directed Heterocycle Libraries," *J. Am. Chem. Soc.*, 2002, 124(8), 1594-1596.
Ding, S., et al., "Resin-Capture and Release Strategy toward Combinatorial Libraries of 2,6,9-Substituted Purines," *J. Comb. Chem.*, 2002, 4, 183-186.
Ding, S., et al., "A Concise and Traceless Linker Strategy toward Combinatorial Libraries of 2,6,9-Substituted Purines," *J. Org. Chem.*, 2001, 66, 8273-8276.
Fajans S. et al., "Maturity Onset Diabetes of the Young (MODY)," *Diabet. Med.*, 1996, 13, S90-S95.
Feinstein, M.B. et al., "Regulation of the Action of Hydrocotisone in Airway Epithelial Cells by 11β-Hydroxysteroid Dehydrogenase," *Am. J. Respir. Cell. Mol. Biol.*, 1999, 21, 403-408.
Fingl E. et al., "General Principles," *The Pharmacological Basis of Therapeutics, Fifth Edition*, 1975, Ch. 1, 1-46.
Forrest, G. L. et al., "Induction of a Human Carbonyl Reductase Gene Located on Chromosome 21," *Biochim. Biophys. Acta*, 1990, 1048, 149-155.
Forrest, G.L. et al., "Carbonyl Reductase," *Chem. Biol. Interact.*, 2000, 129, 21-40.
Funder, J.W., et al., "Mineralocorticoid Action: Target Tissue Specificity Is Enzyme, Not Receptor, Mediated," *Science*, 1988, 242, 583-585.
Garber, M.E. et al., "Diversity of Gene Expression in Adenocarcinoma of the Lung," *Proc. Nat. Acad. Sci. USA*, 2001, 98(24), 13784-13789.
Gonzalez, B. et al., "Protection against Daunorubicin Cytotoxicity by Expression of a Cloned Human Carbonyl Reductase cDNA in K562 Leukemia Cells," *Cancer Res.*, 1995, 55, 4646-4650.

Haase, A. et al., "Detection of Viral Nucleic Acids by in Situ Hybridization," *Methods in Virology*, 1984, vol. VII, 189-226.
Hanefeld, U. et al., "One-pot Synthesis of Tetrasubstituted Pyrazoles Proof of Regiochemistry," *J. Chem. Soc. Perkin Trans.*, 1996, 1, 1545-1552.
Ishiyama, T. et al., "Mild Iridium-Catalyzed Borylation of Arenes. High Turnover Numbers, Room Temperature Reactions, and Isolation of a Potential Intermediate," *J. Am. Chem. Soc.*, 2002, 124(3), 390-391.
Ishiyama, T. et al., "A Stoichiometric Aromatic C-H Borylation Catalyzed by Iridium(I)/2,2'-Bipyridine Complexes at Room Temperature," *Angew. Chem. Int. Ed.*, 2002, 41(16), 3056-3058.
Kallberg, Y. et al., "Short-Chain Dehydrogenases/Reductases (SDRs)" *Eur. J. Biochem.*, 2002, 269, 4409-4417.
Kallberg, Y. et al., "Short-Chain Dehydrogenase/Reductase (SDR) Relationships: a Large Family with Eight Clusters Common to Human, Animal, and Plant Genomes," *Protein Sci.*, 2002, 11, 636-641.
Kwok, B.H. et al., "The Anti-Inflammatory Natural Product Parthenolide from the Medicinal Herb Feverfew Directly Binds to and Inhibits IκB Kinase," *Chem. Biol.*, 2001, 8, 759-766.
Mayer, T.U. et al., "Small Molecule Inhibitor of Mitotic Spindle Bipolarity Identified in a Phenotype-Based Screen," *Science*, 1999, 286, 971-974.
Moon, H.S. et al., "A Novel Microtubule Destabilizing Entity from Orthogonal Synthesis of Triazine Library and Zebrafish Embryo Screening," *J. Am. Chem. Soc.*, 2002, 124, 11608-11609.
Nakanishi, M. et al., "Cloning and Sequence Analysis of a cDNA Encoding Tetrameric Carbonyl Reductase of Pig Lung," *Biochem. Biophys. Acta*, 1993, 194(3), 1311-1316.
Nobel, C.S.I. et al., "Purification of Full-Length Recombinant Human and Rat Type 1 11β-hydroxysteroid Dehydrogenases with Retained Oxidoreductase Activities," *Protein Expr. Purif.*, 2002, 26, 349-356.
Oppermann, U.C. et al., "Forms and Functions of Human SDR Enzymes," *Chem. Biol. Interact.*, 2001, 130-132(1-3), 699-705.
Persson, C.G., "Glucocorticoids for Asthma—Early Contributions," *Pulm. Pharmacol.*, 1989, 2, 163-166.
Pudlo, J.S. et al., "Synthesis, Antiproliferative, and Antiviral Activity of Certain 4-Substituted and 4,5 Disubstituted 7-[(1,3-Dihydroxy-2-propoxy)methyl]pyrrolo[2,3-d]pyrimidines," *J. Med. Chem.*, 1990, 33, 1984-1992.
Robertson, R.P., "Eicosanoids and Human Disease," *Harrison's Principles of Internal Medicine*, Isselbacher K. J. et al. (eds.), McGraw-Hill, New York City 1994, vol. 1, 431-435.
Romero, D.G. et al., "Cloning and Expression of the Bovine 11β-hydroxysteroid Dehydrogenase Type-2," *J. Steroid Biochem. Mol. Biol.*, 2000, 72, 231-237.
Singer, R.H. et al., "Optimization of in situ Hybridization Using Isotopic and Non-Isotopic Detection Methods," *Biotechniques*, 1986, 4(3), 230-250.
Soldan, M. et al., "Induction of Daunorubicin Carbonyl Reducing Enzymes by Daunorubicin in Sensitive and Resistant Pancreas Carcinoma Cells," *Biochem. Pharmacol.*, 1996, 51, 117-123.
Ugarkar, B.G. et al., "Adenosine Kinase Inhibitors. 2. Synthesis, Enzyme Inhibition, and Antiseizure Activity of Diaryltubercidin Analogues," *J. Med. Chem.*, 2000, 43, 2894-2905.
White, P.C. et al., "11β-Hydroxysteroid Dehydrogenase and the Syndrome of Apparent Mineralocorticoid Excess," *Endocr. Rev.*, 1997, 18(1), 135-156.
"Report of the Expert Committee on the Diagnosis and Classification of Diabetes Mellitus," *Diabetes Care*, 1999, 2 (Suppl 1), S5-S19.

* cited by examiner

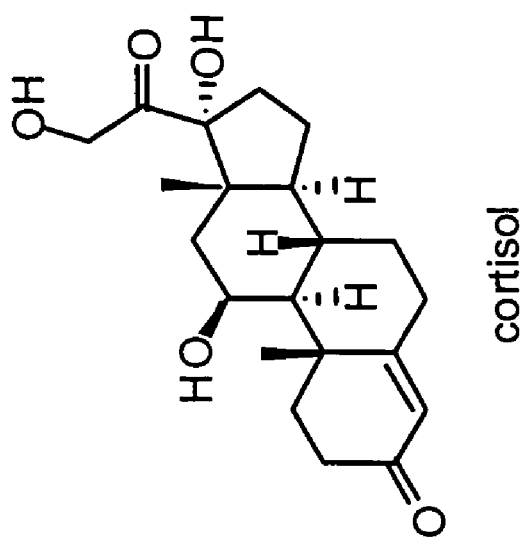
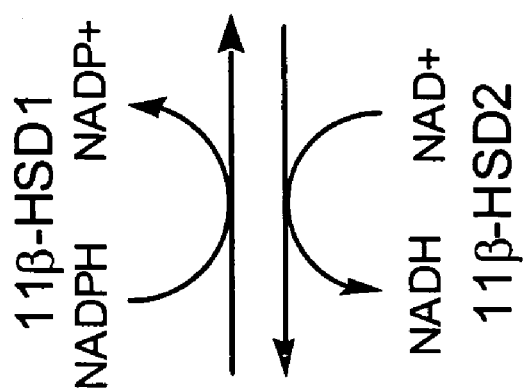
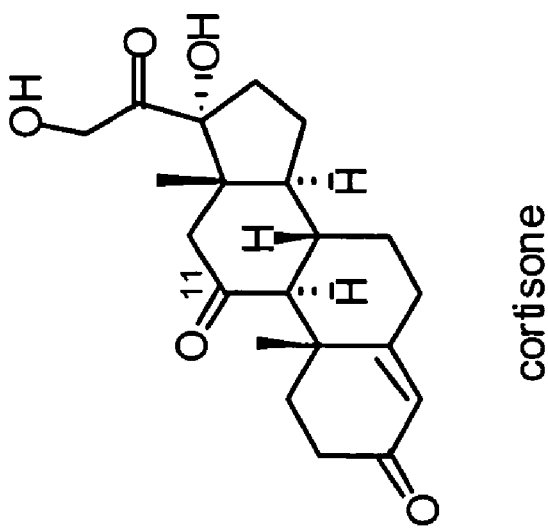
Figure 2

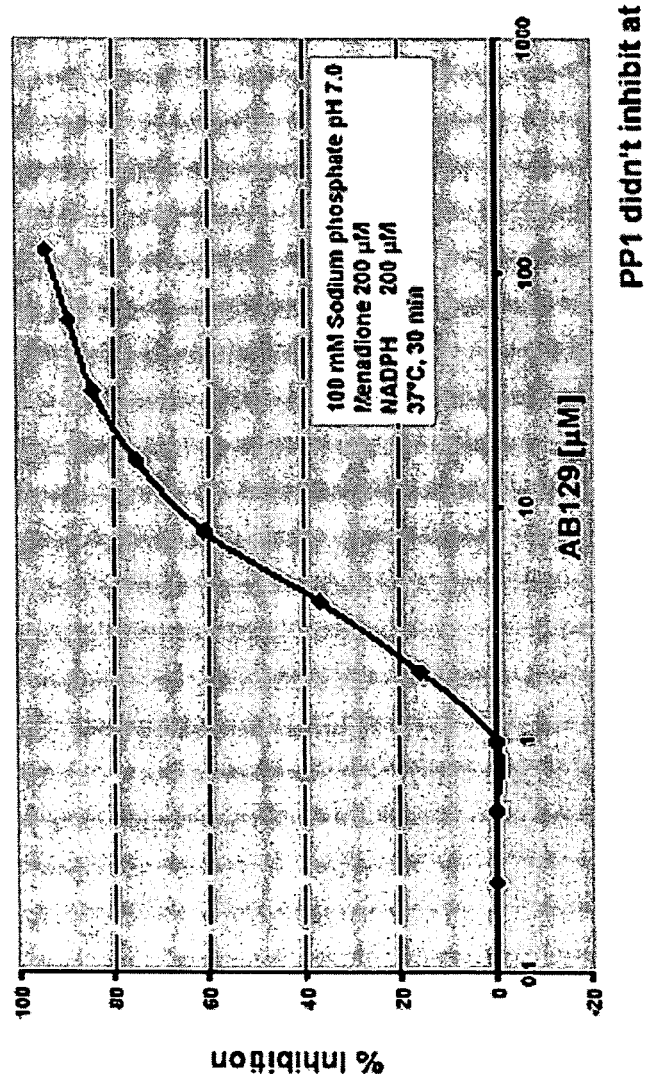
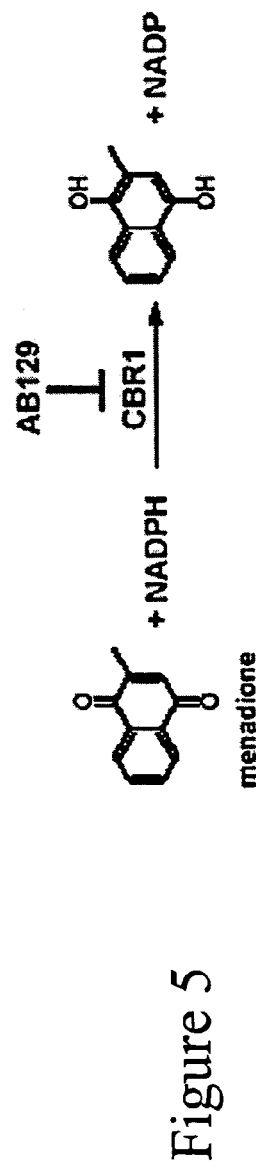
Figure 5

Kinetic analysis of wt CBR1

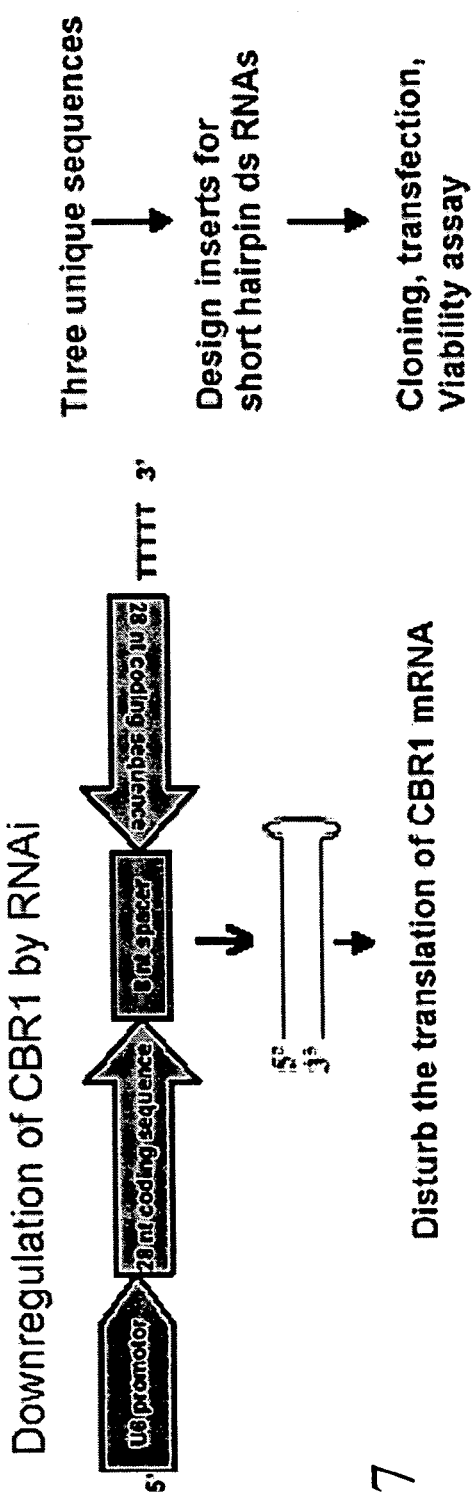

Figure 7

Carbonyl reductase 1 cDNA gi:4502598 cagactcgagcagtctgaacacgctgcggggtcccggctccaggcctgagccaggtgttcgtcgtgcgggcatccatgt
agcgctggtgadgaggcaacaaggcatoggcttggccatgtgcacaacctatctcaggggaacatggtgctcacgcgcgggagogtgacgcgg
ggccaggcggccglacagcgcglcagggaggcgcctgagccaggcctggcgctgagccgcgtccaccagctgcgacatcgcgcgatctggacatgcagcatcggcgcgcctgcgcgactcctgcgca
aggagtacgggggcctggcgtctggtgtcacacacgcgggcatcgggcatcccttcatattcaaggtgcctcaaggtgctgatcccacacccttcatattcaagctgaaagctcaggcgaattctttg
gtaccgagatgtgtgcacgaattactcctctaatnaaacccaaggagagttgtggagcatcatgaacaatgtttgtgaggatacaaanaacaatgatttgnatg
tgcagcagaagttccgcagtacgcgccatcactgaggagcgagcttgtcgtggggctcatcgttctgccaggatgagcgggaaactgagtgagcagagacccctgtgtactggcccctgtcaaagc
gccagcagcgcaatacggggtgacgaactgacatggccgggaccccaagcgcaccaagagcccagaaggtgcagagacccctgtactggcccctttgcccccagatgctg
ctgctgccaggggtgggtgagaactgtttgttcagaagaaggagttgaacagtggtggctggtgaacagtggagagttgaaagcgcccatcatcatgagccccattgtactctgcgagtgtccaaaggc
aggtcccatcalggacaattgttcagaagaaggagttgaaacagtggagagttgaacagtggctccatcatgtaactactaatgtactacatantgagcaactacgacaactgacactacgtaaaatg
attacaatgtcataaataacccctatatagaaanaaaatgatcttatacaattagcactcactaaaatgtaaatgaaaataacgatgaaatanacgatagaatanalggttcttataagtg
tcaggtcttttgattttctctgatgcaggagagagggaaaaattgtaatgatgaaaaaatgaaatgaaatcgaatgaaatgaaatggttcttataagtg

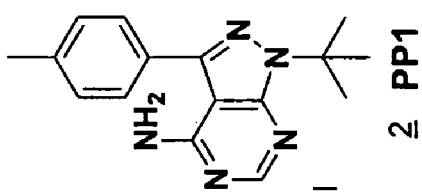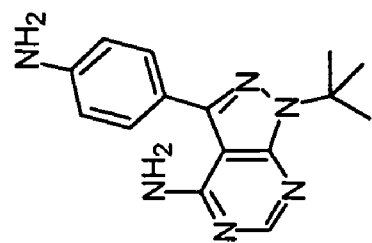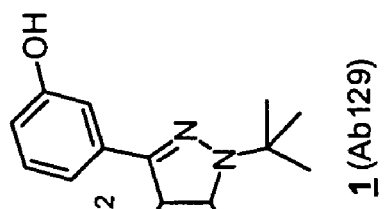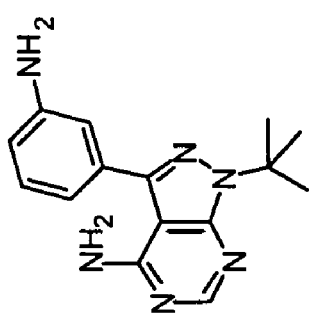
Figure 10

Figure 18

MS/MS Fragmentation of VLSIQSHVIR
Found in PDXK_HUMAN, (O00764) Pyridoxal kinase (EC 2.7.1.35) (Pyridox Match to Query 22 (384.57,3+) Elution from: 19.54 to 19.54 period: 0 experiment: 1 cycles: 1
From data file C:\DOCUME~1\ADMINI~1.MAS\LOCALS~1\Temp\mas28.tmp

Figure 19

Kinetic parameters

| | Substrate NADPH | | Inhibitor AB129 | |
|---|---|---|---|---|
| | $K_m$ [µM] | $k_{cat}$ [s$^{-1}$] | $K_i$ [µM] | IC$_{50}$ [µM] |
| Wild-type | 12 | 0.6 | 0.4 | 6.0 |
| N90V | 83 | 0.9 | 22 | 60 |

Figure 23

Docking of AB129 within porcine CBR

Gly11 and Asn89 are conserved.

| | Gly 11 | Asn 89 |
|---|---|---|
| CBR (Pig) | SSNTRVALVTGANKG-----IGFAIVRD- | LVNNAAIAFQLDNPTPFHIQA-ELTMKTNFMGT |
| CBR-1 (Human) | SSGIHVALVTGGNKG-----IGLAIVRD- | -LVNNAGIAFKVADPTPFHIQA-EVTMKTNFFGT |
| CBR-3 (Human) | SSCSRVALVTGANRG-----IGLAIARE- | -LVNNAAVAFKSDDPMPFDIKA-EMTLKTNFFAT |
| 17B-HSD-1 (Human) | ARTVVLITGCSSGIG----LHLAVRLASD- | -LVCNAGLGL-LGPLEALGEDAVASVLDVNVVGT |
| 11B-HSD-1 (Human) | YYSANEEFRPEMLQGK---KVIVTGASKG- | -LILNHITNTSL-NLFHDDIHHVRKSMEVNFLSY |
| 11B-HSD-2 (Human) | ARALLQLLRSDLRLGRPLLAALALLAALDW | GLVNNAGHNEVVADAELSPVATFRSCMEVNFFGA |

Figure 25

Sequence alignment of NADPH binding pocket in SDRs

```
              1
hCBR1         MSSGIHVALVTGGNKGIGLAIVRDLC...
17β-HSD1      ARTVLITGCSSGIGLHLAVRLA...
11β-HSD1   ...EMLQGKKVIVTGASKGIGREMAYHLA...
                 ::** .. :  *.

hCBR1      ...GGLDVLVNNAGI..
17β-HSD1   ...GRVDVLVCNAGL..
11β-HSD1   ...GGLDMILNHIT..
              *.::*:*: :

194
hCBR1      ...NVSSIMSVRA..AYGVTKI...
17β-HSD1   ...VTGSVGGLMG..VYCASKF...
11β-HSD1   ...VVSSLAGKVA..AYSASKF...
              ::*:  .    : :*

233
hCBR1      ...VRTDMAG...
17β-HSD1   ...DRTDIHT...
11β-HSD1   ...IDTETAM...
              . *. :
```

Figure 26

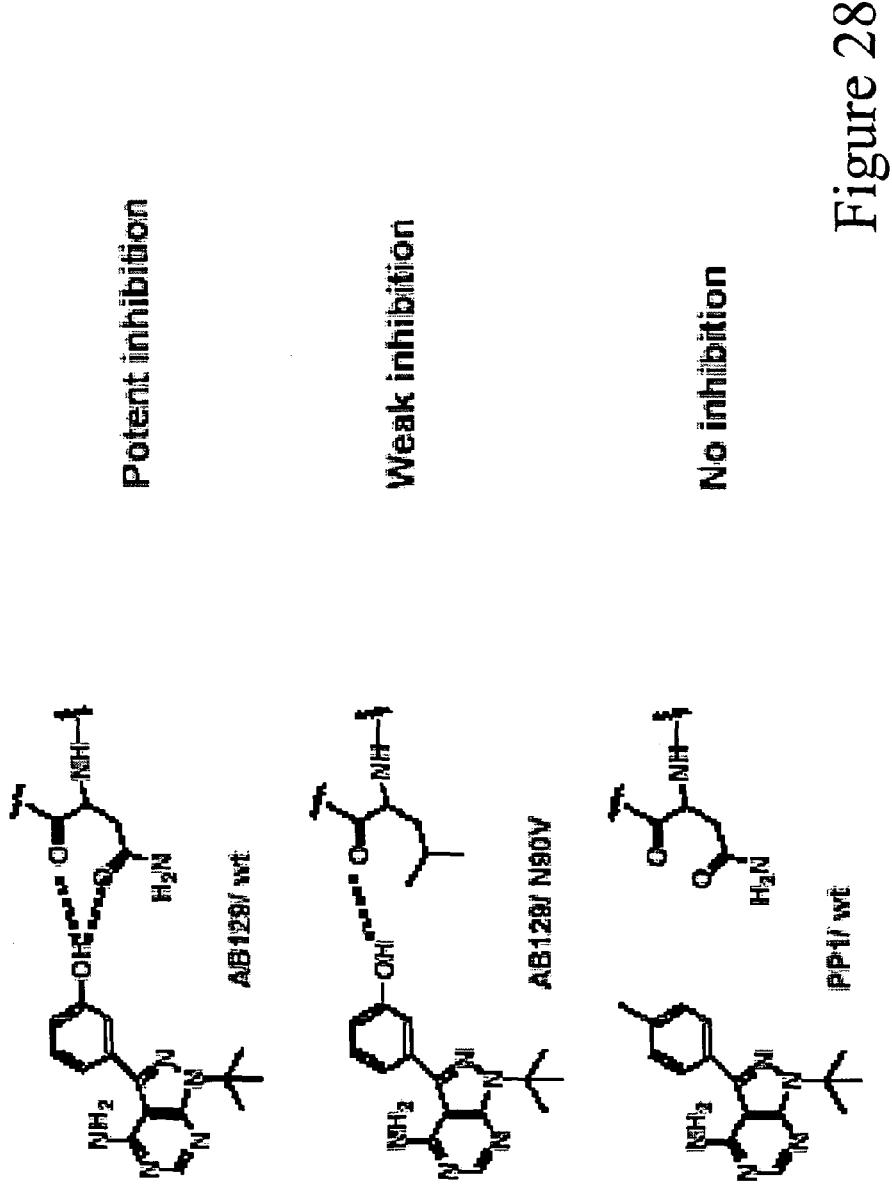
Figure 28. Effects on inhibition by mutation at Asn90

Asn90 is important for the binding of AB129

Expression vector

↓

Site directed mutagenesis

Expression in *E.

AB129 analogs display differing selectivities for CBR and kinases:
| | PP1 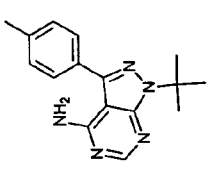 | AB129 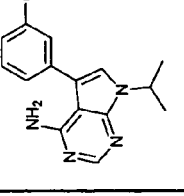 | RB2 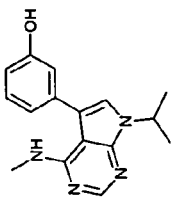 | RB5 | RB6 |
|---|---|---|---|---|---|
| Anti-CBR | - | 300 nM $K_I$ | ~300 nM $K_I$ | ~300 nM $K_I$ | ~300 nM $K_I$ |
| Anti-Kinase (Fyn) | 50 nM $IC_{50}$ | 6 nM $IC_{50}$ | 14 nM $IC_{50}$ | 7 nM $IC_{50}$ | ? |
| A549 morphology | - | + | + | + | - |
Figure 35

Pyrrolopyrimidine Scaffold Validation

Analogs of AB129 that posses an isopropyl group at R² were prepared.

Compounds possessing identical substituents with both a pyrazolopyrimidine (RB2) and a pyrrolopyrimidine scaffold were prepared.

1H-PYRROLO [2,3-D] PYRIMIDINE DERIVATIVES AND METHODS OF USE THEREOF

CROSS-REFERENCE TO RELATED APPLICATION

This application claims priority to U.S. Application No. 60/480,501, filed Jun. 20, 2003, the entire disclosure of which is incorporated herein by reference.

This invention was made with Government support by Grant Nos. AI44009 and NCRR RR01614 awarded by the National Institutes of Health. The Government has certain rights in this invention.

FIELD

This invention generally relates to pyrazolo pyrimidine derivatives, including derivatives and analogs of inhibitors of short chain dehydrogenase/reductase (SDR) family of NAD(P)(H) dependent oxido-reductases. More specifically, the invention relates to pyrazolo and pyrollo pyrimidine derivatives, including derivatives and analogs of SDR inhibitors, pharmaceutical compositions containing the pyrazolo pyrimidine derivatives, and methods of making and methods of use thereof.

BACKGROUND

Cancer of the lung and bronchus (lung cancer) is the second most common cancer among both men and women and is the leading cause of cancer death in both sexes. Among men, age-adjusted lung cancer incidence rates (per 100,000) range from a low of about 14 to a high of 117, an eight- fold difference, depending upon ethnicity. The rates among men are about two to three times greater than the rates among women in each of the racial/ethnic groups.

Leukemia and lymphoma are the most common fatal cancers in young men under age 39. Leukemia, Hodgkin and non-Hodgkin lymphoma and myeloma are cancers that originate in the bone marrow or lymphatic tissues. An estimated 106,300 people in the United States will be diagnosed with leukemia, lymphoma or myeloma in 2002. New cases of leukemia, Hodgkin and non-Hodgkin lymphoma and myeloma account for 8.3 percent of the 1,284,900 new cancer cases diagnosed in the United States this year. See Surveillance, Epidemiology and End Results (SEER) Program 1979-1998, National Cancer Institute; American Cancer Society.

An estimated 616,695 Americans are currently living with leukemia, Hodgkin and non-Hodgkin lymphoma and myeloma. Leukemia, lymphoma and myeloma will cause the deaths of an estimated 58,300 people in the United States this year. These blood cancers will account for nearly 10.5 percent of the deaths from cancer in 2002 based on the total of 555, 500 cancer-related deaths (all sites).

The short chain dehydrogenase/reductase (SDR) family of NAD(P)(H) dependent oxido-reductases are believed to have a role in disease, for example, cancer, inflammatory disease, and diabetes. The SDR family represents a diverse family of >63 human proteins (Oppermann, U. C., et al., *Chem Biol Interact*, 130-132: 699-705, 2001. Kallberg, Y., et al., *Eur J Biochem*, 269: 4409-17, 2002. Kallberg, Y., et al., *Protein Sci*, 11: 636-41, 2002). These enzymes are responsible for the oxidation or reduction of a wide range of endogenous (prostaglandins, steroid hormones, retinal, dihydropteridin, UDP, and trans 2-enoyl CoA) and exogenous chemicals (anthracyclin drugs, quininones, and others). The SDR family members thus control the cell specific production/destruction of potent hormones as well as the detoxification of important classes of drugs such as the anti-cancer agent adriamycin (Forrest, G. L. et al., *Chem Biol Interact*, 129: 21-40, 2000).

Carbonyl reductase (CBR) (NADPH: secondary-alcohol oxidoreductase) is part of a group of NADPH-dependent cytosolic enzymes called short chain dehydrogenase/reductase (SDR) that catalyze the reduction of various carbonyl compounds to their corresponding alcohols. The enzyme is ubiquitous in nature and acts on a large number of biologically and pharmacologically active compounds. Carbonyl reductase is believed to function physiologically as a dehydrogenase or reductase of prostaglandins or hydroxysteroids, as well as in drug metabolism.

Carbonyl reductase is primarily monomeric in structure, and has been characterized in humans from placenta, liver, and breast tissue. CBR bears a low overall degree of homology (24-36%) with other SDR enzymes from mammalian sources such as mouse and pig (Nakanishi, M. et al. *Biochem. Biophys. Acta* 194: 1311-16, 193). However, all of these enzymes are linked by two common consensus sequences; the sequence TGxxxGxG, found in the N-terminal portion of the molecule and responsible for binding the NADPH co-enzyme, and the sequence YxxxK, located close to the C-terminal end of the molecule, and active in carbonyl reduction. Differences in amino acid sequences between these enzymes can be responsible, in part, for differences in their respective substrate specificities for various carbonyl compounds.

The bioreduction of prostaglandin (PGE) by carbonyl reductase serves to regulate cellular levels of PGE. A wide variety of biological activities are ascribed to PGEs including smooth muscle contraction, platelet aggregation, inflammation, inhibition of insulin secretion, and lymphocyte function. Excessive PGE production is associated with inflammatory diseases, diabetes, and suppression of the immune response. Inhibitors of PGE biosynthesis, such as indomethacin and ibuprofen, are commonly used to treat inflammation and inflammatory diseases and depressed cellular immunity in patients with conditions such as Hodgkin's disease (Isselbacher K. J. et al. *Harrison's Principles of Internal Medicine*, Vol. 1: 431-435, 1994, McGraw-Hill, New York City).

In human liver, carbonyl reductase also reduces quinones, an important class of mutagens and carcinogens, and appears to be the principle mechanism for detoxification of these compounds. CBR production is stimulated by carcinogens such as butyl hydroxyanisole and beta-naphthoflavone that also induce other cancer-protective enzymes (Forrest, G. L. et al. *Biochim. Biophys. Acta* 1048: 149-55, 1990).

Human carbonyl reductase 1 (CBR1) has been characterized as having similarity to carbonyl reductases from porcine lung (GI 416425), mouse adipocytes (GI 50004), and human liver (GI 118519). Human CBR1 is 85% identical to porcine carbonyl reductase. The role of carbonyl reductase in cells is not understood.

Carbonyl reductase is also involved in the metabolism of anthracyclines, a widely used class of anticancer chemotherapeutic drugs. Daunorubicin (DNR) and Doxorubicin (DXR), the two principle anthracyclines used in cancer chemotherapy, are reduced to their respective alcohols by carbonyl reductase. The alcohol products are much less effective anti-tumor agents than the parent compounds. In fact, increased carbonyl reductase levels associated with some anthracycline resistant tumors suggest that increased carbonyl reductase activity may be responsible for drug resistance in these cells (Soldan, M. et al. *Biochem. Pharmacol.* 51: 116-23, 1996; Gonzalez, B. et al. *Cancer Res.* 55: 4646-50, 1995). Another problem of anthracyclines is cardiotoxicity, but the causative agents are suggested to be the alcohol products of carbonyl reductase catalyzed reaction. (Forrest, G. L. et al., *Chem Biol Interact*, 129: 21-40, 2000.)

Daunorubicin is one of the family of anthracycline antibiotic drugs that include daunorubicin, doxorubicin, epirubicin, and idarubicin. These drugs are used in the treatment of acute leukemia, lymphomas, and myeloma. Daunorubicin is used to treat acute myeloid leukemia, acute lymphocytic leukemia, chronic myelogenous leukemia, neuroblastoma. Liposomal daunorubicin belongs to the general group of medicines known as antineoplastics. It is used to treat advanced acquired immunodeficiency syndrome (AIDS)-associated Kaposi's sarcoma (KS), Molecules that inhibit short chain dehydrogenase/reductase (SDR) family of NAD(P)(H) dependent oxido-reductases, for example, carbonyl reductase, satisfy a need in the art by providing new diagnostic or therapeutic compositions useful in the prevention and treatment of inflammation, immunological disorders, cancer, and drug resistance in cancerous cells, and reducing toxicity associated with CBR catalyzed metabolites of known drugs.

SUMMARY

The invention is generally related to inhibitors of short chain dehydrogenase/reductase (SDR) family of NAD(P)(H) dependent oxido-reductases, and derivatives and analogs thereof. The invention further relates to pharmaceutical compositions containing the inhibitors of SDR family of NAD(P)(H) dependent oxido-reductases, and derivatives and analogs thereof, methods of making the inhibitors of SDR family of NAD(P)(H) dependent oxido-reductases and derivatives and analogs thereof, and methods of use thereof.

In one embodiment, the present invention is directed to a compound of Formula I or II:

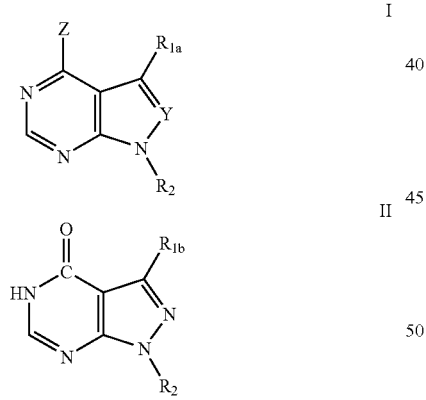

or a pharmaceutically-acceptable salt or prodrug thereof; wherein:

Y is N or $CR_5$;

Z is $NR_3R_4$, halo, H, ,OH, alkyl, alkyloxy, or haloalkyl;

$R_{1a}$ is indolyl, thiazolyl, benzyl, biphenylyl, thiophenyl, pyrrolyl, or phenyl, wherein said phenyl is substituted with at least one of OH, —$NR_3R_4$, —C(=O)$NR_6R_7$, —CN, $NO_2$—C(=O)OH, —C(=O)O-alkyl, ($C_1$-$C_4$)alkyl, halo, haloalkyl or haloaryl; and wherein said indolyl, thiazolyl, benzyl, biphenylyl, thiophenyl, or pyrrolyl is optionally substituted with OH, —$NR_3R_4$, —C(=O)$NR_6R_7$, —CN, $NO_2$, —C(=O)O—$R_3$, ($C_1$-$C_4$)alkyl, halo, haloalkyl or haloaryl;

$R_{1b}$ is indolyl, thiazolyl, benzyl, biphenylyl, thiophenyl, pyrrolyl, or phenyl wherein said indolyl, thiazolyl, benzyl, biphenylyl, thiophenyl, pyrrolyl, phenyl is optionally substituted with —OH, —$NR_3R_4$, —C(=O)$NR_6R_7$, —CN, $NO_2$, —C(=O)O—$R_3$, ($C_1$-$C_4$)alkyl, halo, haloalkyl, or haloaryl;

$R_2$ is $C_1$-$C_6$ alkyl or $C_4$-$C_7$ cycloalkyl, wherein said alkyl or said cycloalkyl is optionally substituted with mono- or di-alkoxy, mono- or di-halophenyl, mono- or di-($C_{1-4}$)alkoxy phenyl, mono- or di-($C_{1-4}$)alkyl phenyl, perhalo($C_{1-4}$)alkyl phenyl, carboxyl, tert-butyl carboxyl, phosphoryl, ($C_{1-6}$)alkyl, ($C_{4-7}$)cycloalkyl, indolyl, isoindolyl, pyridyl, naphthyl, pyrrolyl, imidazolyl, pyrazolyl, pyridyl, pyrimidinyl, pyrazinyl, pyridazinyl, furyl, thienyl, or alkylmorpholino;

$R_3$ and $R_4$ are independently H, $C_1$-$C_6$ alkyl, t-Boc, morpholino($C_1$-$C_4$)alkyl, carboxy($C_1$-$C_3$)alkyl, ($C_1$-$C_4$)alkoxycarbonyl($C_1$-$C_3$)alkyl, aryl, heteroaryl, aryloxy, heterocycle, cycloalkyl, alkenyl with the proviso that the double bond of the alkenyl is not present at the carbon atom that is directly linked to N, alkynyl with the proviso that the triple bond of the alkynyl is not present at the carbon atom that is directly linked to N, perfluoroalkyl, —S(O)$_2$alkyl, —S(O)$_2$aryl, —(C=O)heteroaryl, —(C=O)aryl, —(C=O)($C_1$-$C_6$) alkyl, —(C=O)cycloalkyl, —(C=O)heterocycle, alkyl-heterocycle, aralkyl, arylalkenyl, —CON$R_6R_7$, —SO$_2R_6R_7$, arylalkoxyalkyl, arylalkylalkoxy, heteroarylalkylalkoxy, aryloxyalkyl, heteroaryloxyalkyl, aryloxyaryl, aryloxyheteroaryl, alkylaryloxyaryl, alkylaryloxyheteroaryl, alkylaryloxyalkyamine, alkoxycarbonyl, aryloxycarbonyl, or heteroaryloxycarbonyl;

$R_5$ are independently H, —OH, halo, optionally monosubstituted ($C_1$-$C_6$)alkyl, optionally monosubstituted ($C_1$-$C_4$)alkoxycarbonyl, optionally monosubstituted ($C_1$-$C_4$)alkanoyl, carbamoyl, optionally monosubstituted ($C_1$-$C_4$)alkyl carbamoyl, phenyl, halophenyl, optionally monosubstituted ($C_1$-$C_4$)alkylphenyl, optionally monosubstituted ($C_1$-$C_4$)alkoxyphenyl, or optionally monosubstituted perhalo($C_1$-$C_4$)alkylphenyl, wherein said optional substitution is ($C_1$-$C_4$) alkyl, OH, or halogen;

$R_6$ and $R_7$ are independently H, alkyl, aryl, heteroaryl, alkylaryl, arylalkyl, heteroarylalkyl, or alkylheteroaryl;

provided the compound is not 1-tert-butyl-3-p-tolyl-1H-pyrazolo[3,4-d]pyrimidin-4-ylamine.

In another embodiment, the present invention is directed to a method for preventing or treating cancer in a mammal, comprising the step of administering to the mammal an effective amount of a compound of formula I or formula II, or a pharmaceutically acceptable salt thereof.

In yet another embodiment, the present invention is directed to a method for preventing or treating a disease or condition associated with carbonyl reductase 1 in a mammal in need thereof, comprising the steps of administering to the mammal a composition comprising an effective amount of a compound of formula I or formula II, or a pharmaceutically acceptable salt thereof.

In yet another embodiment, the present invention is directed to a method of preventing or treating a disease or condition associated with the synthesis of prostaglandin E in a mammal in need thereof comprising the steps of administering to the mammal a composition comprising an effective amount of a compound of formula I or formula II, or a pharmaceutically acceptable salt thereof, and inhibiting synthesis of prostaglandin E2.

In a further embodiment, the present invention is directed to a method for preventing or treating a disease or condition associated with short chain dehydrogenase/reductase (SDR) family of NAD(P)(H) dependent oxido-reductases in a mammal in need thereof, comprising the step of administering to the mammal an effective amount of a composition comprising an effective amount of a compound of formula I or formula II, or a pharmaceutically acceptable salt thereof.

In a further embodiment, the present invention is directed to a method for identifying a therapeutic cancer treatment, comprising the steps of contacting a tumor cell culture with an effective amount of a composition comprising an effective amount of a compound of formula I or formula II, or a pharmaceutically acceptable salt thereof, measuring growth inhibition of the tumor cells in culture; and identifying a therapeutic cancer treatment for a mammalian subject by inhibition of the tumor cell growth in culture.

BRIEF DESCRIPTION OF THE DRAWINGS

FIG. 2 shows enzymatic activity of 11β-hydroxysteroid dehydrogenase I and 11β-hydroxysteroid dehydrogenase II.

FIG. 5 shows AB129 inhibits menadione reducing activity of carbonyl reductase 1 (CBR1).

FIG. 7 shows selection of RNAi hairpins for targeting of carbonyl reductase 1 (CBR1).

FIG. 10 shows the structure of (1) AB129, (2) PP1, (3) AB60, and (4) AB61.

Figure 18:
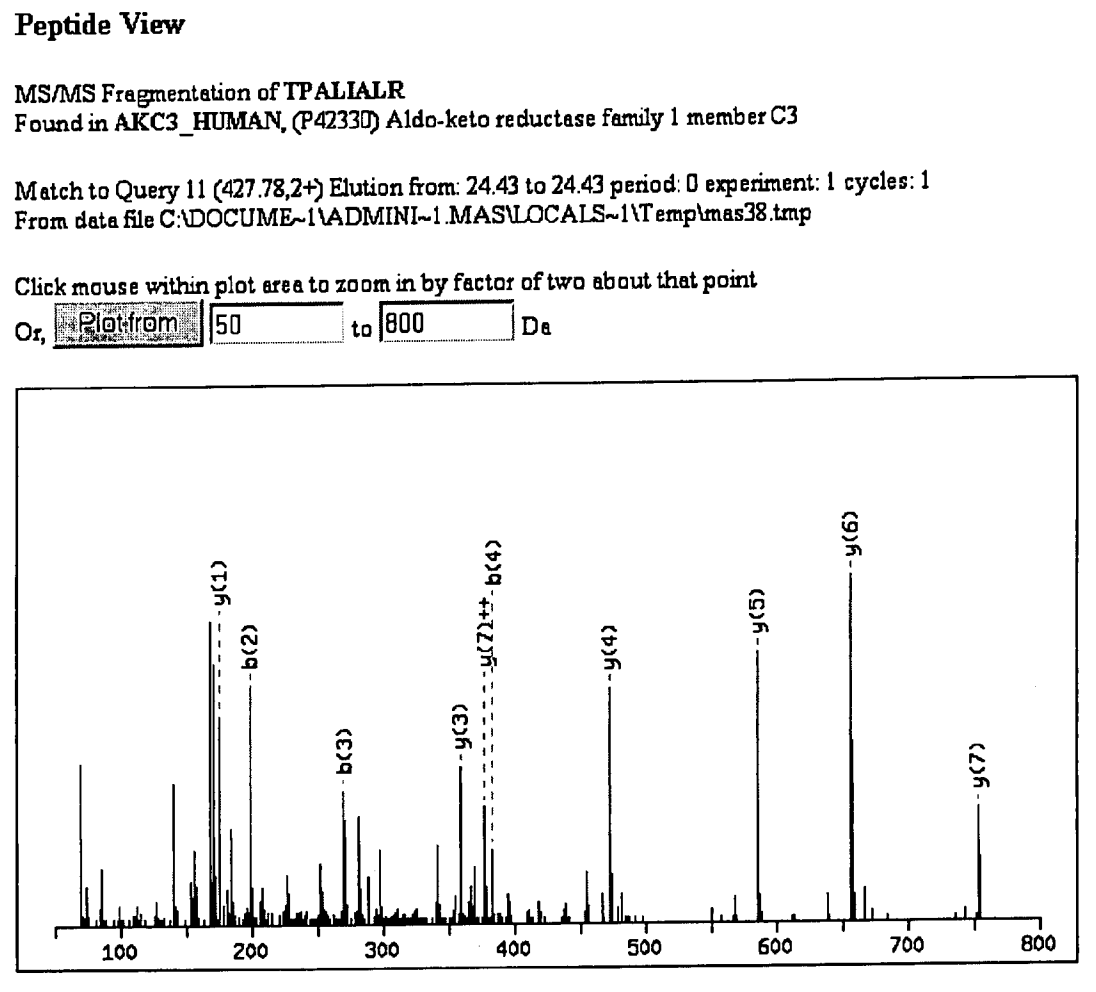

FIG. 18 shows mass spectrometric identification of protein fragments.

FIG. 19 shows mass spectrometric identification of protein fragments.

FIG. 23 kinetic parameters of AB129 inhibition of carbonyl reductase 1 (CBR1).

FIG. 25 shows conserved amino acid residues in short chain dehydrogenase/reductase (SDR) enzymes.

FIG. 26 shows sequence alignment of NADPH binding pocket in SDR enzymes.

FIG. 28 shows effects on inhibition by mutation at Asn90 of carbonyl reductase 1 (CBR1).

FIG. 29 shows Asn90 has a role for binding of AB129 to carbonyl reductase 1 (CBR1).

FIG. 35 shows AB129 analogs display differing selectivities for carbonyl reductase (CBR) and kinases.

DETAILED DESCRIPTION OF ILLUSTRATIVE EMBODIMENTS

Figure 1:
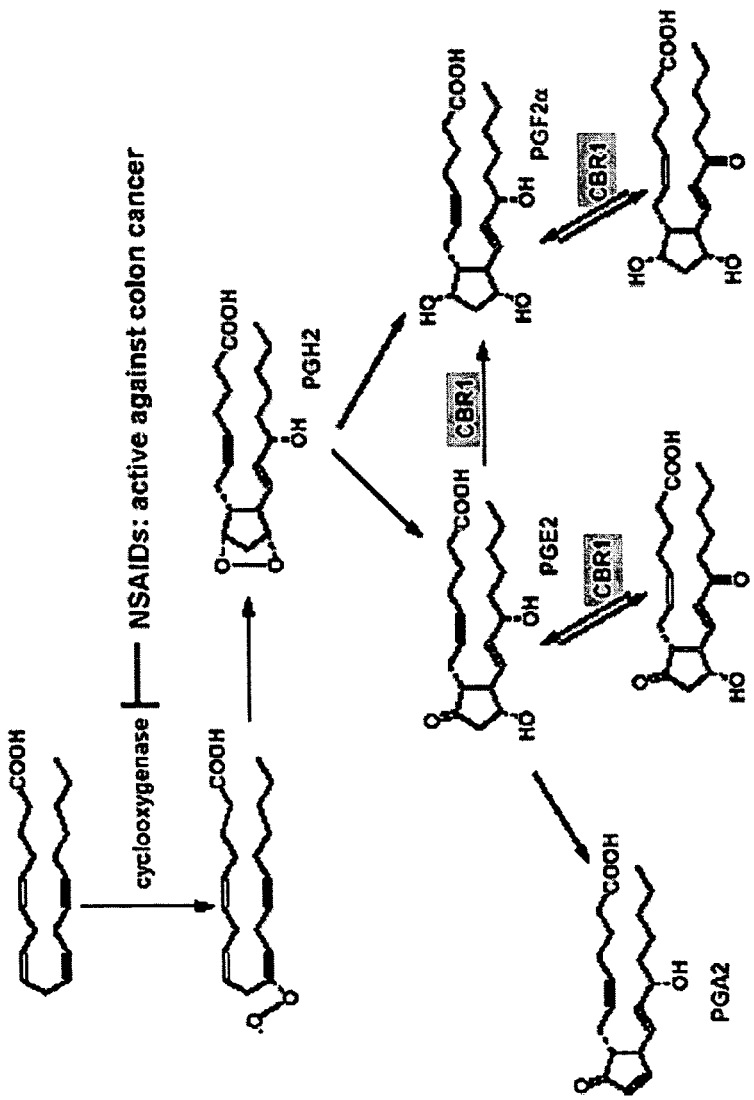
FIG. 1 shows the role of CBR in the biosynthesis of prostaglandins.

With respect to pyrazolo pyrimidine or, "derivative" refers to a compound of general formula I or II:

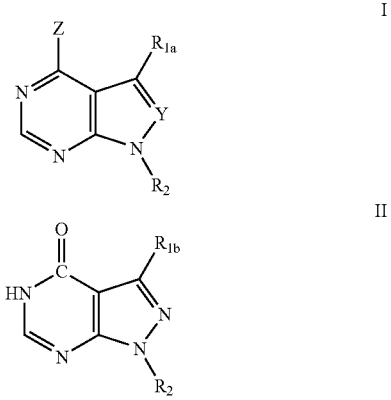

where the variables are as defined herein.

With respect to pyrazolo pyrimidine or AB-129 compound, "analog" or "functional analog" refers to a modified form of the respective pyrazolo pyrimidine or AB-129 compound derivative in which one or more chemically derivatized functional substituent ($R_{1a}$, $R_{1b}$, $R_2$, $R_3$, $R_4$ or Z) or a ring atom (Y) has been modified such that the analog retains substantially the same biological activity or improved biological activity as the unmodified pyrazolo pyrimidine or AB-129 compound derivative in vivo and/or in vitro.

The present invention is directed to pyrazolo pyrimidine derivatives, compositions containing these derivatives, and methods of their use for the prevention and treatment of, inter alia, cancer, metastatic cancer, inflammation, and diabetes.

The following definitions are provided for the full understanding of terms and abbreviations used in this specification.

As used herein and in the appended claims, the singular forms "a," "an," and "the" include the plural reference unless the context clearly indicates otherwise. Thus, for example, a reference to "an antagonist" or "an agonist" includes a plurality of such antagonists or a plurality of such agonists, and a reference to "a compound" is a reference to one or more compounds and equivalents thereof known to those skilled in the art, and so forth.

The abbreviations in the specification correspond to units of measure, techniques, properties, or compounds as follows: "min" means minutes, "h" means hour(s), "µL" means microliter(s), "mL" means milliliter(s), "mM" means millimolar, "M" means molar, "mmole" means millimole(s), "cm" means centimeters, "SEM" means standard error of the mean and "IU" means International Units, "° C." means degrees Celcius. "$\Delta ED_{50}$ value" means dose which results in 50% alleviation of the observed condition or effect (50% mean maximum endpoint), "$\Delta ID_{50}$" means dose which results in 50% inhibition of an observed condition or effect or biochemical process (50% mean maximum endpoint).

"Alkyl" refers to an optionally substituted, saturated straight, branched, or cyclic hydrocarbon having from about 1 to about 20 carbon atoms (and all combinations and subcombinations of ranges and specific numbers of carbon atoms therein), with from about 1 to about 8 carbon atoms, herein referred to as "lower alkyl", being preferred. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, cyclohexyl, cyclooctyl, adamantyl, 3-methylpentyl, 2,2-dimethylbutyl, and 2,3-dimethylbutyl.Lower alkyl refers to alkyl having 1 to 4 carbon atoms.

"Cycloalkyl" refers to an optionally substituted, alkyl group having one or more rings in their structures having from about 3 to about 20 carbon atoms (and all combinations and subcombinations of ranges and specific numbers of carbon atoms therein), with from about 3 to about 10 carbon atoms being preferred. Multi-ring structures can be bridged or fused ring structures. Groups include, but are not limited to, cyclopropyl, cyclobutyl, cyclopentyl, cyclohexyl, cyclooctyl, and adamantyl. Specifically included within the definition of "cyclic alkyl" are those aliphatic hydrocarbon chains that are optionally substituted.

"Perfluorinated alkyl" refers to an alkyl, as defined above, in which the hydrogens directly attached to the carbon atoms are completely replaced by fluorine.

"Alkenyl" refers to an alkyl group of at least two carbon atoms having one or more double bonds, wherein alkyl is as defined herein. Alkenyl groups can be optionally substituted.

"Alkynyl" refers to an alkyl group of at least two carbon atoms having one or more triple bonds, wherein alkyl is as defined herein. Alkynyl groups can be optionally substituted.

"Aryl" as used herein, refers to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred. Non-limiting examples include, for example, phenyl, naphthyl, anthracenyl, and phenanthrenyl.

"Heteroaryl" refers to an optionally substituted, mono-, di-, tri-, or other multicyclic aromatic ring system that includes at least one, and preferably from 1 to about 4 sulfur, oxygen, or nitrogen heteroatom ring members. Heteroaryl groups can have, for example, from about 3 to about 50 carbon atoms (and all combinations and subcombinations of ranges and specific numbers of carbon atoms therein), with from about 4 to about 10 carbons being preferred. Non-limiting examples of heteroaryl groups include, for example, pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl.

"Heterocyclic ring" refers to a stable 5- to 7-membered monocyclic or bicyclic or 7- to 10-membered bicyclic heterocyclic ring that is saturated, partially unsaturated or unsaturated (aromatic), and which contains carbon atoms and from 1 to 4 heteroatoms independently selected from the group consisting of N, O and S and including any bicyclic group in which any of the above defined heterocyclic rings is fused to a benzene ring. The nitrogen and sulfur heteroatoms may optionally be oxidized. The heterocyclic ring may be attached to its pendant group at any heteroatom or carbon atom that results in a stable structure. The heterocyclic rings described herein may be substituted on carbon or on a nitrogen atom if the resulting compound is stable. If specifically noted, a nitrogen atom in the heterocycle may optionally be quaternized. It is preferred that when the total number of S and O atoms in the heterocycle exceeds one, then these heteroatoms are not adjacent to one another. It is preferred that the total number of S and O atoms in the heterocycle is not more than one. Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4H-carbazolyl, α-, β-, or γ-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl., oxazolyl, oxazolidinylpyrimidinyl, phenanthridinyl, phenanthrolinyl, phenoxazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl. Also included are fused ring and spiro compounds containing, for example, the above heterocycles.

"Alkoxy" refers to the group R—O— where R is an alkyl group as defined herein.

"Aryloxy" refers to the group R—O— where R is an aryl group, as defined herein.

"Heteroaryloxy" refers to the group R—O— where R is a heteroaryl group, as defined herein.

"Alkanoyl" refers to the group R—C(=O) where R is an alkyl group of 1 to 5 carbon atoms.

"Alkanoyloxy" refers to the group R—C(=O)—O where R is an alkyl group of 1 to 5 carbon atoms.

"Halo," refers to chloro, bromo, fluoro, and iodo.

"Haloalkyl," or "haloaryl" refers to an alkyl or aryl, as defined above, in which one or more hydrogens directly attached to the carbon atoms are replaced by one or more halo substituents.

"Optional" or "optionally" means that the subsequently described event or circumstance may or may not occur, and that the description includes instances in which it does not. For example, optionally substituted phenyl indicates either unsubstituted phenyl, or phenyl mono-, di, or tri-substituted, independently, with OH, COOH, lower alkyl, lower alkoxy, halo, nitro, amino, alkylamino, dialkylamino, trifluoromethyl and/or cyano.

By "therapeutically effective dose" herein is meant a dose that produces effects for which it is administered. The exact dose will depend on the purpose of the treatment, and will be ascertainable by one skilled in the art using known techniques (see, e.g., Lieberman, *Pharmaceutical Dosage Forms* (Vols. 1-3, 1992); Lloyd, 1999, *The Art, Science And Technology Of Pharmaceutical Compounding;* and Pickar, 1999, *Dosage Calculations*). "Effective amount" refers to an amount of a compound that can be therapeutically effective to inhibit, prevent or treat the symptoms of particular disease, disorder or side effect.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/ risk ratio.

"In combination with", "combination therapy" and "combination products" refer, in certain embodiments, to the concurrent administration to a patient of a first therapeutic and the compounds as used herein. When administered in combination, each component can be administered at the same time or sequentially in any order at different points in time. Thus, each component can be administered separately but sufficiently closely in time so as to provide the desired therapeutic effect.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

"Stereoisomer, prodrug, pharmaceutically acceptable salt, hydrate, solvate, acid salt hydrate, N-oxide or isomorphic crystalline form thereof" refer to derivatives of the disclosed compounds wherein the parent compound is modified by making acid or base salts thereof. Examples of stereoisomer, prodrug, pharmaceutically acceptable salt, hydrate, solvate, acid salt hydrate, N-oxide or isomorphic crystalline form thereof include, but are not limited to, mineral or organic acid salts of basic residues such as amines; alkali or organic salts of acidic residues such as carboxylic acids; and the like. The stereoisomer, prodrug, pharmaceutically acceptable salt, hydrate, solvate, acid salt hydrate, N-oxide or isomorphic crystalline form thereof include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein throughout, can be used or prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present compositions and methods.

Certain acidic or basic compounds can exist as zwitterions. All forms of the compounds, including free acid, free base and zwitterions, are contemplated to be within the scope of the present compositions and methods. It is well known in the art that compounds containing both amino and carboxyl groups often exist in equilibrium with their zwitterionic forms. Thus, any of the compounds described herein throughout that contain, for example, both amino and carboxyl groups, also include reference to their corresponding zwitterions.

The term "treating" includes the administration of the compounds or agents of the present invention to prevent or delay the onset of the symptoms, complications, or biochemical indicia of a disease, alleviating the symptoms or arresting or inhibiting further development of the disease, condition, or disorder (e.g., cancer). Treatment may be prophylactic (to prevent or delay the onset of the disease, or to prevent the manifestation of clinical or subclinical symptoms thereof) or therapeutic suppression or alleviation of symptoms after the manifestation of the disease.

In general, the phrase "well tolerated" refers to the absence of adverse changes in health status that occur as a result of the treatment and would affect treatment decisions. Except when noted, the terms "patient" or "subject" are used interchangeably and refer to mammals such as human patients and non-human primates, as well as experimental animals such as rabbits, rats, and mice, and other animals.

"Prodrug" refers to compounds specifically designed to maximize the amount of active species that reaches the desired site of reaction which are of themselves typically inactive or minimally active for the activity desired, but through biotransformation are converted into biologically active metabolites.

"Stereoisomers" refers to compounds that have identical chemical constitution, but differ as regards the arrangement of the atoms or groups in space.

When any variable occurs more than one time in any constituent or in any formula, its definition in each occurrence is independent of its definition at every other occurrence. Combinations of substituents and/or variables are permissible only if such combinations result in stable compounds.

"Short chain dehydrogenase reductase (SDR)" refers to a family of NAD(P)(H) dependent oxido-reductases represent a diverse family of greater than 63 human proteins. These enzymes are responsible for the oxidation or reduction of a wide range of endogenous (prostaglandins, steroid hormones, retinal, dihydropteridin, UDP, and trans 2-enoyl CoA) and exogenous chemicals (e.g., anthracyclin drugs).

"Modulate" refers to the suppression, enhancement or induction of a function or condition. For example, the pyrazolo pyrimidine or AB-129 compounds, derivatives and analogs thereof of the invention can modulate cancer by inhibition of short chain dehydrogenase reductase (SDR) enzyme activity. For example, AB-129 compounds, derivatives and analogs thereof can inhibit carbonyl reductase 1 (CBR1) activity in lung carcinoma cells thereby alleviating lung cancer by inhibiting or reducing growth of lung carcinoma cells.

"Carbonyl reductase" refers to a family of enzymes, for example, carbonyl reductase 1 (NADPH: secondary-alcohol oxidoreductase) which is part of a group of NADPH-dependent cytosolic enzymes called short chain dehydrogenase/reductase (SDR) that catalyze the reduction of various carbonyl compounds to their corresponding alcohols. The enzyme is ubiquitous in nature and acts on a large number of biologically and pharmacologically active compounds. Carbonyl reductase is believed to function physiologically as dehydrogenases of prostaglandins or hydroxysteroids, as well as in drug metabolism.

"11β-hydroxysteroid dehydrogenase (11β-HSD)" refers to 11β-hydroxysteroid dehydrogenase I or 17β-hydroxysteroid dehydrogenase II, or an enzyme with a related activity.

"17β-hydroxysteroid dehydrogenase(17β-HSD)" refers to 17β-hydroxysteroid dehydrogenase I or 17β-hydroxysteroid dehydrogenase II, or an enzyme with a related activity.

"Anthracycline anti-cancer agent" refers to the family of anthracycline antibiotic drugs that include, for example daunorubicin, doxorubicin, epirubicin, and idarubicin.

"Cardiotoxic side effect" refers to acute or chronic cardiomyopathy that can lead to congestive heart failure. The development of chronic cardiotoxicity is clinically important. Chronic cardiotoxicity can develop many years after treatment with anthracyclines. Children and younger adults treated with anthracyclines are exposed to a lifetime risk of developing serious cardiomyopathy. Because cancer patients are not usually monitored for more than 5-7 years, the number of these patients developing late-onset cardiomyopathies can be expected to increase substantially in the future.

"Cancer" or "malignancy" are used as synonymous terms and refer to any of a number of diseases that are characterized by uncontrolled, abnormal proliferation of cells, the ability of affected cells to spread locally or through the bloodstream and lymphatic system to other parts of the body (i.e., metastasize) as well as any of a number of characteristic structural and/or molecular features. A "cancerous" or "malignant cell" is understood as a cell having specific structural properties, lacking differentiation and being capable of invasion and metastasis. Examples of cancers are kidney, colon, breast, prostate and liver cancer. (see DeVita, V. et al. (eds.), 2001, CANCER PRINCIPLES AND PRACTICE OF ONCOLOGY, 6th. Ed., Lippincott Williams & Wilkins, Philadelphia, Pa.; this reference is herein incorporated by reference in its entirety for all purposes).

"Cancer-associated" refers to the relationship of a nucleic acids and its expression, or lack thereof, or a protein and its level or activity, or lack thereof, to the onset of malignancy in a subject cell. For example, cancer can be associated with expression of a particular gene that is not expressed, or is expressed at a lower level, in a normal healthy cell. Conversely, a cancer-associated gene can be one that is not expressed in a malignant cell (or in a cell undergoing transformation), or is expressed at a lower level in the malignant cell than it is expressed in a normal healthy cell.

"Neoplastic cells" and "neoplasia" refer to cells which exhibit relatively autonomous growth, so that they exhibit an aberrant growth phenotype characterized by a significant loss of control of cell proliferation. Neoplastic cells comprise cells which can be actively replicating or in a temporary non-replicative resting state (G1 or G0); similarly, neoplastic cells can comprise cells which have a well-differentiated phenotype, a poorly-differentiated phenotype, or a mixture of both type of cells. Thus, not all neoplastic cells are necessarily replicating cells at a given timepoint. The set defined as neoplastic cells consists of cells in benign neoplasms and cells in malignant (or frank) neoplasms. Frankly neoplastic cells are frequently referred to as cancer (discussed supra), typically termed carcinoma if originating from cells of endodermal or ectodermal histological origin, or sarcoma if originating from cell types derived from mesoderm.

In the context of the invention, the term "transformation" refers to the change that a normal cell undergoes as it becomes malignant. In eukaryotes, the term "transformation" can be used to describe the conversion of normal cells to malignant cells in cell culture.

"Proliferating cells" are those which are actively undergoing cell division and growing exponentially.

"Loss of cell proliferation control" refers to the property of cells that have lost the cell cycle controls that normally ensure appropriate restriction of cell division. Cells that have lost such controls proliferate at a faster than normal rate, without stimulatory signals, and do not respond to inhibitory signals.

"Leukemia" refers to cancer of cells in the bloodstream or lymphatic system. Types of leukemia include but are not limited to, Acute Lymphoblastic Leukemia (Adult or Childhood), Acute Myeloid Leukemia (Adult or Childhood), Chronic Lymphocytic Leukemia, Chronic Myelogenous Leukemia, or Hairy Cell Leukemia.

"Kaposi's sarcoma (KS)" refers to a sarcoma that develops in connective tissues such as cartilage, bone, fat, muscle, blood vessels, or fibrous tissues (related to tendons or ligaments). The vast majority of KS cases have developed in association with human immunodeficiency virus (HIV) infection and the acquired immunodeficiency syndrome (AIDS). KS tumors develop in the tissues below the skin surface, or in the mucous membranes of the mouth, nose, or anus.

"Inflammation" or "inflammatory response" refers to an innate immune response that occurs when tissues are injured by bacteria, trauma, toxins, heat, or any other cause. The damaged tissue releases compounds including histamine, bradykinin, and serotonin. Inflammation refers to both acute responses (i.e., responses in which the inflammatory processes are active) and chronic responses (i.e., responses marked by slow progression and formation of new connective tissue). Acute and chronic inflammation can be distinguished by the cell types involved. Acute inflammation often involves polymorphonuclear neutrophils; whereas chronic inflammation is normally characterized by a lymphohistiocytic and/or granulomatous response. Inflammation includes reactions of both the specific and non-specific defense systems. A specific defense system reaction is a specific immune system reaction response to an antigen (possibly including an autoantigen). A non-specific defense system reaction is an inflammatory response mediated by leukocytes incapable of immunological memory. Such cells include granulocytes, macrophages, neutrophils and eosinophils. Examples of specific types of inflammation are diffuse inflammation, focal inflammation, croupous inflammation, interstitial inflammation, obliterative inflammation, parenchymatous inflammation, reactive inflammation, specific inflammation, toxic inflammation and traumatic inflammation.

"Diabetes mellitus" or "diabetes" refers to a disease or condition that is generally characterized by metabolic defects in production and utilization of glucose which result in the failure to maintain appropriate blood sugar levels in the body. The result of these defects is elevated blood glucose, referred to as "hyperglycemia." Two major forms of diabetes are Type 1 diabetes and Type 2 diabetes. As described above, Type 1 diabetes is generally the result of an absolute deficiency of insulin, the hormone which regulates glucose utilization. Type 2 diabetes often occurs in the face of normal, or even elevated levels of insulin and can result from the inability of tissues to respond appropriately to insulin. Most Type 2 diabetic patients are insulin resistant and have a relative deficiency of insulin, in that insulin secretion can not compensate for the resistance of peripheral tissues to respond to insulin. In addition, many Type 2 diabetics are obese. Other types of disorders of glucose homeostasis include Impaired Glucose Tolerance, which is a metabolic stage intermediate between normal glucose homeostasis and diabetes, and Gestational Diabetes Mellitus, which is glucose intolerance in pregnancy in women with no previous history of Type 1 or Type 2 diabetes.

"Secondary diabetes" is diabetes resulting from other identifiable etiologies which include: genetic defects of β cell function (e.g., maturity onset-type diabetes of youth, referred to as "MODY," which is an early-onset form of Type 2 diabetes with autosomal inheritance; see, e.g., Fajans S. et al., *Diabet. Med.* 9 Suppl 6: S90-5, 1996, and Bell, G. et al., *Annu. Rev. Physiol.* 58: 171-86, 1996); genetic defects in insulin action; diseases of the exocrine pancreas (e.g., hemochromatosis, pancreatitis, and cystic fibrosis); certain endocrine diseases in which excess hormones interfere with insulin action (e.g., growth hormone in acromegaly and cortisol in Cushing's syndrome); certain drugs that suppress insulin secretion (e.g., phenytoin) or inhibit insulin action (e.g., estrogens and glucocorticoids); and diabetes caused by infection (e.g., rubella, Coxsackie, and CMV); as well as other genetic syndromes.

The guidelines for diagnosis for Type 2 diabetes, impaired glucose tolerance, and gestational diabetes have been outlined by the American Diabetes Association (see, e.g., *The Expert Committee on the Diagnosis and Classification of Diabetes Mellitus, Diabetes Care*, 2 (Suppl 1): S5-19, 1999).

Methods of Treatment

Short chain dehydrogenases/reductases (SDRs), for example, carbonyl reductase 1 (CBR1) have a role in metabolism and disease. AB129-type compounds and analogs thereof are inhibitors of the SDR enzyme family. AB129-type compounds and analogs are useful for medical treatment, for example, cancer therapy, and have been shown to have biological activity.

(1) Human carbonyl reductase 1 (CBR1) is within the family of short chain dehydrogenases/reductases (SDRs).

(2) The SDR enzyme family has more than 1600 members. Greater than 63 SDR enzymes are found in human.

(3) SDR enzymes catalyze an NAD(P)(H)-dependent oxidoreduction or dehydrogenation.

(4) The catalytic active site of the SDR enzyme comprises an S/YxxxK catalytic triad.

(5) The function of SDR enzymes include intermediary metabolism, lipid hormone metabolism (e.g., steroids, prostaglandins, retinols/retinals) and enzymes of unknown function.

(6) SDR enzymes are correlated with many genetic and metabolic disorders.

(7) SDR enzymes can regulate the nuclear hormone switch (e.g., cortisone, estradiol, prostaglandin) as an important regulatory target by AB129-type compounds.

(8) AB129-type compounds and analogs thereof that inhibit carbonyl reductase 1 (CBR1) activity are useful for treatment of lung cancer, colon cancer, metastatic cancer, or cancer drug resistance.

(9) AB129-type compounds and analogs thereof that inhibit 11β-hydroxysteroid dehydrogenase activity and result in decreased levels of cortisone are useful for treatment of diabetes or obesity.

(10) AB129-type compounds and analogs thereof that inhibit 17β-hydroxysteroid dehydrogenase activity are useful for treatment of inflammatory disease, ovarian cancer or breast cancer.

In one embodiment, the present invention is directed to a compound of Formula I or II:

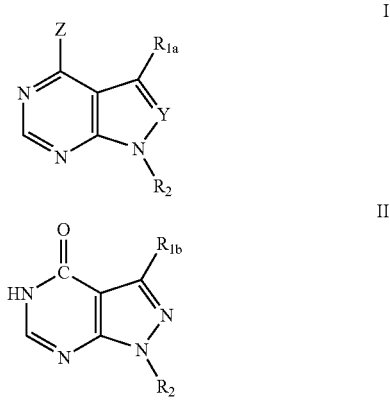

or a pharmaceutically-acceptable salt or prodrug thereof; wherein:

Y is N or $CR_5$;

Z is $NR_3R_4$, halo, H, ,OH, alkyl, alkyloxy, or haloalkyl;

$R_{1a}$ is indolyl, thiazolyl, benzyl, biphenylyl, thiophenyl, pyrrolyl, or phenyl, wherein said phenyl is substituted with at least one of OH, —$NR_3R_4$, —C(=O)$NR_6R_7$, —CN, $NO_2$, —C(=O)OH, —C(=O)O-alkyl, ($C_1$-$C_4$)alkyl, halo, haloalkyl or haloaryl; and wherein said indolyl, thiazolyl, benzyl, biphenylyl, thiophenyl, or pyrrolyl is optionally substituted with OH, —$NR_3R_4$, —C(=O)$NR_6R_7$, —CN, $NO_2$, —C(=O)O—$R_3$, ($C_1$-$C_4$)alkyl, halo, haloalkyl or haloaryl;

$R_{1b}$ is indolyl, thiazolyl, benzyl, biphenylyl, thiophenyl, pyrrolyl, or phenyl wherein said indolyl, thiazolyl, benzyl, biphenylyl, thiophenyl, pyrrolyl, phenyl is optionally substituted with —OH, —$NR_3R_4$, —C(=O)$NR_6R_7$, —CN, $NO_2$, —C(=O)O—$R_3$, ($C_1$-$C_4$)alkyl, halo, haloalkyl, or haloaryl;

$R_2$ is $C_1$-$C_6$ alkyl or $C_4$-$C_7$ cycloalkyl, wherein said alkyl or said cycloalkyl is optionally substituted with mono- or di-alkoxy, mono- or di-halophenyl, mono- or di-($C_{1-4}$)alkoxy phenyl, mono- or di-($C_{1-4}$)alkyl phenyl, perhalo($C_{1-4}$)alkyl phenyl, carboxyl, tert-butyl carboxyl, phosphoryl, ($C_{1-6}$)alkyl, ($C_{4-7}$)cycloalkyl, indolyl, isoindolyl, pyridyl, naphthyl, pyrrolyl, imidazolyl, pyrazolyl, pyridyl, pyrimidinyl, pyrazinyl, pyridazinyl, furyl, thienyl, or alkylmorpholino;

$R_3$ and $R_4$ are independently H, $C_1$-$C_6$ alkyl, t-Boc, morpholino($C_1$-$C_4$)alkyl, carboxy($C_1$-$C_3$)alkyl, ($C_1$-$C_4$)

alkoxycarbonyl($C_1$-$C_3$)alkyl, aryl, heteroaryl, aryloxy, heterocycle, cycloalkyl, alkenyl with the proviso that the double bond of the alkenyl is not present at the carbon atom that is directly linked to N, alkynyl with the proviso that the triple bond of the alkynyl is not present at the carbon atom that is directly linked to N, perfluoroalkyl, —S(O)$_2$alkyl, —S(O)$_2$aryl, —(C═O)heteroaryl, —(C═O)aryl, —(C═O)($C_1$-$C_6$)alkyl, —(C═O)cycloalkyl, —(C═O)heterocycle, alkyl-heterocycle, aralkyl, arylalkenyl, —CON$R_6R_7$, —SO$_2$$R_6R_7$, arylalkoxyalkyl, arylalkylalkoxy, heteroarylalkylalkoxy, aryloxyalkyl, heteroaryloxyalkyl, aryloxyaryl, aryloxyheteroaryl, alkylaryloxyaryl, alkylaryloxyheteroaryl, alkylaryloxyalkyamine, alkoxycarbonyl, aryloxycarbonyl, or heteroaryloxycarbonyl;

$R_5$ are independently H, —OH, halo, optionally monosubstituted ($C_1$-$C_6$)alkyl, optionally monosubstituted ($C_1$-$C_4$)alkoxycarbonyl, optionally monosubstituted ($C_1$-$C_4$)alkanoyl, carbamoyl, optionally monosubstituted ($C_1$-$C_4$)alkyl carbamoyl, phenyl, halophenyl, optionally monosubstituted ($C_1$-$C_4$)alkylphenyl, optionally monosubstituted ($C_1$-$C_4$)alkoxyphenyl, or optionally monosubstituted perhalo($C_1$-$C_4$)alkylphenyl, wherein said optional substitution is ($C_1$-$C_4$) alkyl, OH, or halogen;

$R_6$ and $R_7$ are independently H, alkyl, aryl, heteroaryl, alkylaryl, arylalkyl, heteroarylalkyl, or alkylheteroaryl;

provided the compound is not 1-tert-butyl-3-p-tolyl-1H-pyrazolo[3,4-d]pyrimidin-4-ylamine.

In certain embodiments, Y is N.

In a detailed embodiment, $R_{1a}$ or $R_{1b}$ is phenyl substituted with mono, di or tri-OH. In a further detailed embodiment, the phenyl is further substituted with a halo. In a further detailed embodiment, the halo is F.

In a detailed embodiment, $R_2$ is 2-methyl-propane. In a detailed embodiment, $R_3$ and $R_4$ are H. In a detailed embodiment, $R_5$ is H. In a detailed embodiment, $R_6$ is H and $R_7$ is methyl.

In certain embodiments, $R_{1a}$ is, independently, phenyl substituted at a meta position with —CH$_3$, tert-butyl, —CF$_3$ or halo. In a detailed embodiment, $R_{1a}$ is, independently, phenyl substituted at a meta position with halo, alkyl, haloalkyl, haloaryl, aryl, O-alkyl, CN, NO$_2$, CO—O—$R_3$, CO—N($R_3$)$_2$. In a detailed embodiment, Z is F, Br Cl, or I In a detailed embodiment, the compounds of formula I or formula II include:
3-(4-amino-7-isopropyl-7H-pyrrolo[2,3-d]pyrimidin-5-yl)-phenol;
3-(7-isopropyl-4-methylamino-7H-pyrrolo[2,3-d]pyrimidin-5-yl)-phenol;
[5-(3-amino-phenyl)-7-isopropyl-7H-pyrrolo[2,3-d]pyrimidin-4-yl]-methyl-amine;
3-(4-benzylamino-7-isopropyl-7H-pyrrolo[2,3-d]pyrimidin-5-yl)-phenol;
3-(4-dibenzylamino-7-isopropyl-7H-pyrrolo[2,3-d]pyrimidin-5-yl)-phenol;
3-[5-(3-hydroxy-phenyl)-4-methylamino-pyrrolo[2,3-d]pyrinidin-7-yl]-propionic acid tert-butyl ester;
3-[5-(3-hydroxy-phenyl)-4-methylamino-pyrrolo[2,3-d]pyrimidin-7-yl]-propionic acid;
3-bromo-5-(7-isopropyl-4-methylamino-7H-pyrrolo[2,3-d]pyrimidin-5-yl)-phenol;
3-(7-isopropyl-4-methylamino-7H-pyrrolo[2,3-d]pyrimidin-5-yl)-5-methyl-phenol;
3-tert-Butyl-5-(7-isopropyl-4-methylamino-7H-pyrrolo[2,3-d]pyrimidin-5-yl)-phenol;
3-(7-Isopropyl-4-methylamino-7H-pyrrolo[2,3-d]pyrimidin-5-yl)-5-trifluoromethyl-phenol;
3-bromo-5-(4-chloro-7-isopropyl-7H-pyrrolo[2,3-d]pyrimidin-5-yl)-phenol;
3-(4-chloro-7-isopropyl-7H-pyrrolo[2,3-d]pyrimidin-5-yl)-5-methyl-phenol;
3-tert-butyl-5-(4-chloro-7-isopropyl-7H-pyrrolo[2,3-d]pyrimidin-5-yl)-phenol;
3-(4-Chloro-7-isopropyl-7H-pyrrolo[2,3-d]pyrimidin-5-yl)-5-trifluoromethyl-phenol or a pharmaceutically-acceptable salt or prodrug thereof.

In a further detailed embodiment, the compound has the formula:

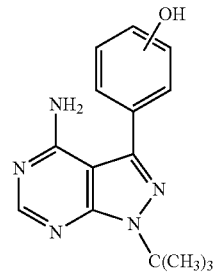

In a further detailed embodiment, the compound has the formula:

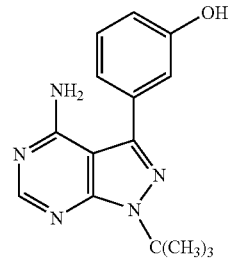

In a further detailed embodiment, the compound has the formula:

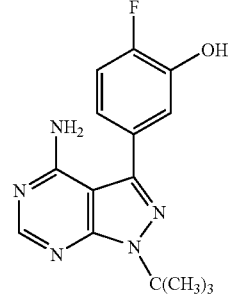

In a further detailed embodiment, the compound has the formula:

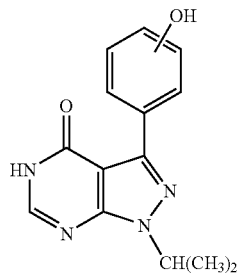

In a further detailed embodiment, the compound has the formula:

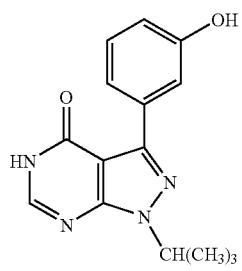

In another embodiment, the pharmaceutical composition, comprises a pharmaceutically acceptable carrier, and the compound. In a detailed embodiment the pharmaceutical composition further comprises at least one anthracycline compound, including but not limited to, daunorubicin doxorubicin, epirubicin, idarubicin, or a mixture thereof.

In another embodiment, methods for preventing or treating a disease or condition associated with carbonyl reductase I in a mammalian are provided, comprising the step of administering to the mammal a composition comprising an effective amount of the compound.

In a further embodiment, the disease state is cancer. In a detailed embodiment, the cancer is lung cancer.

In another embodiment, methods for identifying a therapeutic cancer treatment are provided, comprising contacting a tumor cell culture with an effective amount of the compound.

In another embodiment, methods for alleviating a disease state in a mammal believed to be responsive to treatment with an inhibitor of carbonyl reductase 1 are provided, comprising administering to the mammal an effective amount of the compound, in combination with an effective amount of an anthracycline anti-cancer agent, wherein the disease state of the mammal is alleviated. In a detailed embodiment, the anthracycline anti-cancer agent includes, but is not limited to, daunorubicin, doxorubicin, epirubicin, or idarubicin. In a further detailed embodiment, the potency of the anthracycline anti-cancer agent is maintained in the absence of a cardiotoxic side effect. In a detailed embodiment, the disease state is cancer. In a further detailed embodiment, the disease state is selected from cancer, metastatic cancer, colon cancer, ovarian cancer, leukemia, lymphoma, myeloma, acute myeloid leukemia, acute lymphocytic leukemia, chronic myelogenous leukemia, neuroblastoma, lung cancer, breast cancer, acquired immunodeficiency syndrome (AIDS)associated Kaposi's sarcoma (KS),inflammation, obesity, or diabetes.

In another embodiment, methods of preventing or treating a disease or condition associated with the synthesis of prostaglandin E in a mammal comprises administering to the mammal a effective amount of the compound wherein the disease state of the mammal is alleviated. In a detailed embodiment, the disease state is metastatic cancer. In a detailed embodiment, the disease state is colon cancer.

In another embodiment, methods for alleviating a disease state in a mammal believed to be responsive to treatment with an inhibitor of short chain dehydrogenase/reductase (SDR) family of NAD(P)(H) dependent oxido-reductases, comprise administering to the mammal a effective amount of the compound wherein the disease state of the mammal is alleviated. In a detailed embodiment, the therapeutic amount of the compound inhibits 11β-hydroxysteroid dehydrogenase I. In a detailed embodiment, the therapeutic amount of the compound inhibits 11β-hydroxysteroid dehydrogenase II.

In a detailed embodiment, the therapeutic amount of the compound stimulates synthesis of cortisol. In a further detailed embodiment, the disease state is inflammation.

In a detailed embodiment, the therapeutic amount of the compound stimulates degradation of cortisone. In a further detailed embodiment, the therapeutic amount of the compound alleviates the disease state selected from obesity or diabetes.

In a detailed embodiment, the therapeutic amount of the compound inhibits 17β-hydroxysteroid dehydrogenases. In a further detailed embodiment, the therapeutic amount of the compound alleviates the disease state selected from inflammation, ovarian cancer or breast cancer.

In another embodiment, methods for identifying a therapeutic cancer treatment are provided comprising the steps of: contacting a tumor cell culture with an effective amount of a according to claim 1; measuring growth inhibition of the tumor cells in culture; and identifying a therapeutic cancer treatment for a mammalian subject by inhibition of the tumor cell growth in culture In another embodiment, methods for preventing or treating cancer in a mammal are provided comprising the step of administering to the mammal an effective amount of the compound. In a detailed embodiment, the cancer is lung cancer, metastatic cancer, colon cancer, ovarian cancer, leukemia, lymphoma, myeloma, acute myeloid leukemia, acute lymphocytic leukemia, chronic myelogenous leukemia, neuroblastoma, breast cancer, acquired immunodeficiency syndrome (AIDS)-associated Kaposi's sarcoma (KS).

Pharmaceutical Compositions

Inhibitors and modulators of SDR type enzymes, for example, AB129-type compounds and analogs thereof, are useful in the present compositions and methods and can be administered to a human patient per se, in the form of a stereoisomer, prodrug, pharmaceutically acceptable salt, hydrate, solvate, acid salt hydrate, N-oxide, prodrug ester, or isomorphic crystalline form thereof, or in the form of a pharmaceutical composition where the compound is mixed with suitable carriers or excipient(s) in a therapeutically effective amount, for example, lung cancer or colon cancer. "Prodrug esters" as employed herein includes prodrug esters which are known in the art for carboxylic and phosphorus acid esters such as methyl, ethyl, benzyl and the like.

Routes of Administration

Pharmaceutical compositions of inhibitors and modulators of SDR type enzymes, for example, AB129-type compounds and analogs thereof, described herein can be administered by a variety of routes. Suitable routes of administration can, for example, include oral, rectal, transmucosal, or intestinal administration; parenteral delivery, including intramuscular, subcutaneous, intramedullary injections, as well as intrathecal, direct intraventricular, intravenous, intraperitoneal, spinal, epidural, intranasal, or intraocular injections. Alternatively, one can administer the compound in a local rather than systemic manner, for example via injection of the compound directly into the subject, often in a depot or sustained release formulation. Furthermore, one can administer the compound in a targeted drug delivery system, for example, in a liposome coated vesicle. The liposomes can be targeted to and taken up selectively by the tissue of choice. In a further embodiment, the pharmaceutical compositions of AB129-type compounds and analogs described herein are administered orally.

Composition/Formulation

The pharmaceutical compositions described herein can be manufactured in a manner that is itself known, e.g., by means of conventional mixing, dissolving, granulating, dragee-making, levigating, emulsifying, encapsulating, entrapping or lyophilizing processes. Pharmaceutical compositions for use as described herein can be formulated in conventional manner using one or more physiologically acceptable carriers comprising excipients and auxiliaries which facilitate processing of the active compounds into preparations which can be used pharmaceutically. Proper formulation is dependent upon the route of administration chosen. For injection, the agents can be formulated in aqueous solutions, e.g., in physiologically compatible buffers such as Hanks' solution, Ringer's solution, or physiological saline buffer. For transmucosal administration, penetrants appropriate to the barrier to be permeated are used in the formulation. Such penetrants are generally known in the art. For oral administration, the compounds can be formulated readily by combining with pharmaceutically acceptable carriers that are well known in the art. Such carriers enable the compounds to be formulated as tablets, pills, dragees, capsules, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores.

Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate. Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration. For buccal administration, the compositions can take the form of tablets or lozenges formulated in conventional manner. For administration by inhalation, the compounds for use are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g. gelatin for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents. Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The compounds can also be formulated in rectal compositions such as suppositories or retention enemas, e.g., containing conventional suppository bases such as cocoa butter or other glycerides. In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

A suitable pharmaceutical carrier for hydrophobic compounds is a cosolvent system comprising benzyl alcohol, a nonpolar surfactant, a water-miscible organic polymer, and an aqueous phase. The cosolvent system can be the VPD co-solvent system. VPD is a solution of 3% (w/v) benzyl alcohol, 8% (w/v) of the nonpolar surfactant polysorbate 80, and 65% (w/v) polyethylene glycol 300, made up to volume in absolute ethanol. The VPD co-solvent system (VPD:5W) consists of VPD diluted 1:1 with a 5% (w/v) dextrose in water solution. This co-solvent system dissolves hydrophobic compounds well, and itself produces low toxicity upon systemic administration. Naturally, the proportions of a co-solvent system can be varied considerably without destroying its solubility and toxicity characteristics. Furthermore, the identity of the co-solvent components can be varied: for example, other low-toxicity nonpolar surfactants can be used instead of polysorbate 80; the fraction size of polyethylene glycol can be varied; other biocompatible polymers can replace polyethylene glycol, e.g. polyvinyl pyrrolidone; and other sugars or polysaccharides can substitute for dextrose. Alternatively, other delivery systems for hydrophobic pharmaceutical compounds can be employed. Liposomes and emulsions are well known examples of delivery vehicles or carriers for hydrophobic drugs. Certain organic solvents such as dimethylsulfoxide also can be employed, although usually at the cost of greater toxicity.

Additionally, the compounds can be delivered using a sustained-release system, such as semipermeable matrices of solid hydrophobic polymers containing the therapeutic agent. Various types of sustained-release materials have been established and are well known by those skilled in the art. Sustained-release capsules can, depending on their chemical nature, release the compounds for a few weeks up to over 100 days. The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutically acceptable carriers are determined in part by the particular composition being administered, as well as by the particular method used to administer the composition. Accordingly, there is a wide variety of suitable formulations of pharmaceutical compositions for administering the AB129 (see, e.g., *Remington's Pharmaceutical Sciences*, Mack Publishing Co., Easton, Pa. 18$^{th}$ ed., 1990, incorporated herein by reference). The pharmaceutical compositions generally comprise a differentially expressed protein, agonist or antagonist in a form suitable for administration to a patient. The pharmaceutical compositions are generally formulated as sterile, substantially isotonic and in full compliance with all Good Manufacturing Practice (GMP) regulations of the U.S. Food and Drug Administration.

Effective Dosages

Pharmaceutical compositions suitable for use include compositions wherein the AB129-type compounds and analogs are contained in a therapeutically effective amount. Determination of an effective amount is well within the capability of those skilled in the art, especially in light of the detailed disclosure provided herein. For any compound used in the present method, a therapeutically effective dose can be estimated initially from cell culture assays. For example, a dose can be formulated in animal models to achieve a circulating concentration range that includes the $IC_{50}$ as determined in cell culture (i.e., the concentration of test compound that is lethal to 50% of a cell culture) or the $IC_{50}$ as determined in cell culture (i.e., the concentration of compound that is lethal to 100% of a cell culture). Such information can be used to more accurately determine useful doses in humans. Initial dosages can also be formulated by comparing the effectiveness of the AB129-type compounds and analogs described herein in cell culture assays with the effectiveness of known cancer treatments. In this method an initial dosage can be obtained by multiplying the ratio of effective concentrations obtained in cell culture assay for the AB129-type compounds and analogs and a known cancer treatment by the effective dosage of the known cancer treatment. For example, if an AB129-type compound or analog is twice as effective in cell culture assay than the cancer treatment (i.e., the $IC_{50}$ of AB129 is equal to one half times the $IC_{50}$ cancer treatment in the same assay), an initial effective dosage of the AB129-type compound or analog would be one-half the known dosage for the cancer treatment. Using these initial guidelines one having ordinary skill in the art could determine an effective dosage in humans. Initial dosages can also be estimated from in vivo data. One having ordinary skill in the art could readily optimize administration to humans based on this data. Dosage amount and interval can be adjusted individually to provide plasma levels of the active compound which are sufficient to maintain therapeutic effect. Usual patient dosages for oral administration range from about 50-2000 mg/kg/day, typically from about 250-1000 mg/kg/day, from about 500-700 mg/kg/day or from about 350-550 mg/kg/day. Therapeutically effective serum levels will be achieved by administering multiple doses each day. In cases of local administration or selective uptake, the effective local concentration of the drug can not be related to plasma concentration. One having skill in the art will be able to optimize therapeutically effective local dosages without undue experimentation. The amount of composition administered will, of course, be dependent on the subject being treated, on the subject's weight, the severity of the affliction, the manner of administration and the judgment of the prescribing physician. The therapy can be repeated intermittently while lung cancer or colon cancer is detectable or even when they are not detectable. Moreover, due to its apparent nontoxicity, the therapy can be provided alone or in combination with other drugs, such as for example, anti-inflammatories, antibiotics, corticosteroids, vitamins and the like. Possible synergism between the AB129-type compounds or analogs described herein and other drugs can occur. In addition, possible synergism between a plurality of AB129-type compounds or analogs can occur.

The typical daily dose of a pharmaceutical composition of inhibitors and modulators of SDR type enzymes, for example, AB129-type compounds and analogs thereof, varies according to individual needs, the condition to be treated and with the route of administration. Suitable doses are in the general range of from 0.001 to 10 mg/kg bodyweight of the recipient per day. Within this general dosage range, doses can be chosen at which the pharmaceutical composition of AB129-type compounds and analogs has a positive effect on cancer treatment efficacy. In general, but not exclusively, such doses will be in the range of from 0.5 to 10 mg/kg.

In addition, within the general dose range, doses can be chosen at which the compounds pharmaceutical composition of AB129-type compounds and analogs has a positive effect on cancer treatment efficacy. In general, but not exclusively, such doses will be in the range of from 0.001 to 0.5 mg/kg. It is to be understood that the 2 sub ranges noted above are not mutually exclusive and that the particular activity encountered at a particular dose will depend on the nature of the pharmaceutical composition of AB129-type compounds and analogs used.

The pharmaceutical composition of AB129-type compounds and analogs can be in unit dosage form, for example, a tablet or a capsule so that the patient can self-administer a single dose. In general, unit doses contain in the range of from 0.05-100 mg of a compound of the pharmaceutical composition of AB129-type compounds and analogs. Unit doses contain from 0.05 to 10 mg of the pharmaceutical composition. The active ingredient can be administered from 1 to 6 times a day. Thus daily doses are in general in the range of from 0.05 to 600 mg per day. In an embodiment, daily doses are in the range of from 0.05 to 100 mg per day or from 0.05 to 5 mg per day.

Toxicity

Toxicity and therapeutic efficacy of inhibitors and modulators of SDR type enzymes, for example, AB129-type compounds and analogs thereof, described herein can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio between toxic and therapeutic effect is the therapeutic index and can be expressed as the ratio between $LD_{50}$ and $ED_{50}$. Compounds which exhibit high therapeutic indices are chosen. The data obtained from these cell culture assays and animal studies can be used in formulating a dosage range that is not toxic for use in human. The dosage of such compounds lies within a range of circulating concentrations that include the $ED_{50}$ with little or no toxicity. The dosage can vary within this range depending upon the dosage form employed and the route of administration utilized. The exact formulation, route of administration and dosage can be chosen by the individual physician in view of the patient's condition. (See, e.g., Fingl et al., 1975, In: *The Pharmacological Basis of Therapeutics*, Ch. 1, p. 1). One of the advantages, among others, of using the AB129-type compounds and analogs described herein to treat disease, e.g., lung cancer or colon cancer is their lack of toxicity. For example, it has been found that repeated intraperitoneal doses of 75 mg/kg produced no ill effects in mice (see Example 5). Since the i.v. serum half-life ($t_{1/2}$) of AB129 is about 2-2.5 hours, repeated daily dosages of the AB129 described herein without ill effects is predictable.

Diagnostic Methods

In addition to assays, the creation of animal models, and nucleic acid based therapeutics, identification of important differentially expressed genes allows the use of these genes in diagnosis (e.g., diagnosis of cell states and abnormal epithelial cell conditions). Disorders based on mutant or variant differentially expressed genes can be determined. Methods for identifying cells containing variant differentially expressed genes comprising determining all or part of the sequence of at least one endogenous differentially expressed genes in a cell are provided. As will be appreciated by those in the art, this can be done using any number of sequencing techniques. Methods of identifying the differentially expressed genotype of an individual comprising determining all or part of the sequence of at least one differentially expressed gene of the individual are also provided. This is generally done in at least one tissue of the individual, and can include the evaluation of a number of tissues or different samples of the same tissue. The method can include comparing the sequence of the sequenced differentially expressed gene to a known differentially expressed gene, i.e., a wild-type gene.

The sequence of all or part of the differentially expressed gene can then be compared to the sequence of a known differentially expressed gene to determine if any differences exist. This can be done using any number of known sequence identity programs, such as Bestfit, and others outlined herein. In some methods, the presence of a difference in the sequence between the differentially expressed gene of the patient and the known differentially expressed gene is indicative of a disease state or a propensity for a disease state, as outlined herein.

Similarly, diagnosis of epithelial cell states can be done using the methods and compositions herein. By evaluating the gene expression profile of epithelial cells from a patient, the epithelial cell state can be determined. This is particularly useful to verify the action of a drug, for example an immunosuppressive drug. Other methods comprise administering the drug to a patient and removing a cell sample, particularly of epithelial cells, from the patient. The gene expression profile of the cell is then evaluated, as outlined herein, for example by comparing it to the expression profile from an equivalent sample from a healthy individual. In this manner, both the efficacy (i.e., whether the correct expression profile is being generated from the drug) and the dose (is the dosage correct to result in the correct expression profile) can be verified.

The present discovery relating to the role of differentially expressed in epithelial cells thus provides methods for inducing or maintaining differing epithelial cell states. In one method, the differentially expressed proteins, and particularly differentially expressed fragments, are useful in the study or treatment of conditions which are mediated by epithelial cell activity, i.e., to diagnose, treat or prevent epithelial cell-mediated disorders. Thus, "epithelial cell mediated disorders" or "disease states" can include conditions involving, for example, arthritis, diabetes, or multiple sclerosis.

Methods of modulating epithelial cell activity in cells or organisms are provided. Some methods comprise administering to a cell an anti-differentially expressed antibody or other agent identified herein or by the methods provided herein, that reduces or eliminates the biological activity of the endogenous differentially expressed protein. Alternatively, the methods comprise administering to a cell or organism a recombinant nucleic acid encoding a differentially expressed protein or modulator including anti-sense nucleic acids. As will be appreciated by those in the art, this can be accomplished in any number of ways. In some methods, the activity of differentially expressed is increased by increasing the amount of differentially expressed in the cell, for example by overexpressing the endogeneous differentially expressed or by administering a differentially expressed gene, using known gene therapy techniques, for example. In one method, the gene therapy techniques include the incorporation of the exogenous gene using enhanced homologous recombination (EHR), for example as described in PCT/US93/03868, hereby incorporated by reference in its entirety.

Methods for diagnosing an epithelial cell activity related condition in an individual are provided. The methods comprise measuring the activity of differentially expressed protein in a tissue from the individual or patient, which can include a measurement of the amount or specific activity of the protein. This activity is compared to the activity of differentially expressed from either an unaffected second individual or from an unaffected tissue from the first individual. When these activities are different, the first individual can be at risk for an epithelial cell activity mediated disorder.

Furthermore, nucleotide sequences encoding a differentially expressed protein can also be used to construct hybridization probes for mapping the gene which encodes that differentially expressed protein and for the genetic analysis of individuals with genetic disorders. The nucleotide sequences provided herein can be mapped to a chromosome and specific regions of a chromosome using known techniques, such as in situ hybridization, linkage analysis against known chromosomal markers, and hybridization screening with libraries.

Kits

The differentially expressed protein, agonist or antagonist or their homologs are useful tools for examining expression and regulation of signaling in epithelial cells via the PAR1 pathway. Reagents that specifically hybridize to nucleic acids encoding differentially expressed proteins (including probes and primers of the differentially expressed proteins), and reagents that specifically bind to the differentially expressed proteins, e.g., antibodies, are used to examine expression and regulation.

Nucleic acid assays for the presence of differentially expressed proteins in a sample include numerous techniques are known to those skilled in the art, such as Southern analysis, northern analysis, dot blots, RNase protection, S1 analysis, amplification techniques such as PCR and LCR, high density oligonucleotide array analysis, and in situ hybridization. In in situ hybridization, for example, the target nucleic acid is liberated from its cellular surroundings in such as to be available for hybridization within the cell while preserving the cellular morphology for subsequent interpretation and analysis. The following articles provide an overview of the art of in situ hybridization: Singer et al., *Biotechniques* 4: 230-250, 1986; Haase et al., *Methods in Virology*, vol. VII, pp. 189-226, 1984; and *Nucleic Acid Hybridization: A Practical Approach* (Hames et al., eds. 1987), each incorporated herein by reference. In addition, a differentially expressed protein can be detected with the various immunoassay techniques described above. The test sample is typically compared to both a positive control (e.g., a sample expressing recombinant differentially expressed protein) and a negative control.

Kits for screening epithelial cell activity modulators. Such kits can be prepared from readily available materials and reagents are provided. For example, such kits can comprise any one or more of the following materials: the differentially expressed proteins, agonists, or antagonists, reaction tubes, and instructions for testing the activities of differentially expressed genes. A wide variety of kits and components can be prepared depending upon the intended user of the kit and the particular needs of the user. For example, the kit can be tailored for in vitro or in vivo assays for measuring the activity of a differentially expressed proteins or epithelial cell activity modulators.

Kits comprising probe arrays as described above are provided. Optional additional components of the kit include, for example, other restriction enzymes, reverse-transcriptase or polymerase, the substrate nucleoside triphosphates, means used to label (for example, an avidin-enzyme conjugate and enzyme substrate and chromogen if the label is biotin), and the appropriate buffers for reverse transcription, PCR, or hybridization reactions.

Usually, the kits also contain instructions for carrying out the methods.

Method of Preparation

The compounds of Formula I and II can be prepared in a number of ways well known to those skilled in the art, including both solid phase and solution techniques. The compounds can be synthesized, for example, by the methods described below, or variations thereof as appreciated by the skilled artisan. All processes disclosed in association with the present invention are contemplated to be practiced on any scale, including milligram, gram, multigram, kilogram, multikilogram or commercial industrial scale.

As discussed in detail above, compounds of Formula I or II can contain one or more asymmetrically substituted carbon atoms, and can be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers can be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

As will be readily understood, functional groups present can contain protecting groups during the course of synthesis. Protecting groups are known per se as chemical functional groups that can be selectively appended to and removed from functionalities, such as hydroxyl groups and carboxy groups. These groups are present in a chemical compound to render such functionality inert to chemical reaction conditions to which the compound is exposed. Any of a variety of protecting groups can be employed with the present invention. Preferred protecting groups include the benzyloxycarbonyl group and the tert-butyloxycarbonyl group. Other preferred protecting groups that can be employed in accordance with the present invention are described in Greene, T. W. and Wuts, P. G. M., *Protective Groups in Organic Synthesis* 3d. Ed., Wiley & Sons, 1991.

The compounds of Formula I, where Y is $CR^5$, can be prepared as shown in Scheme 1.

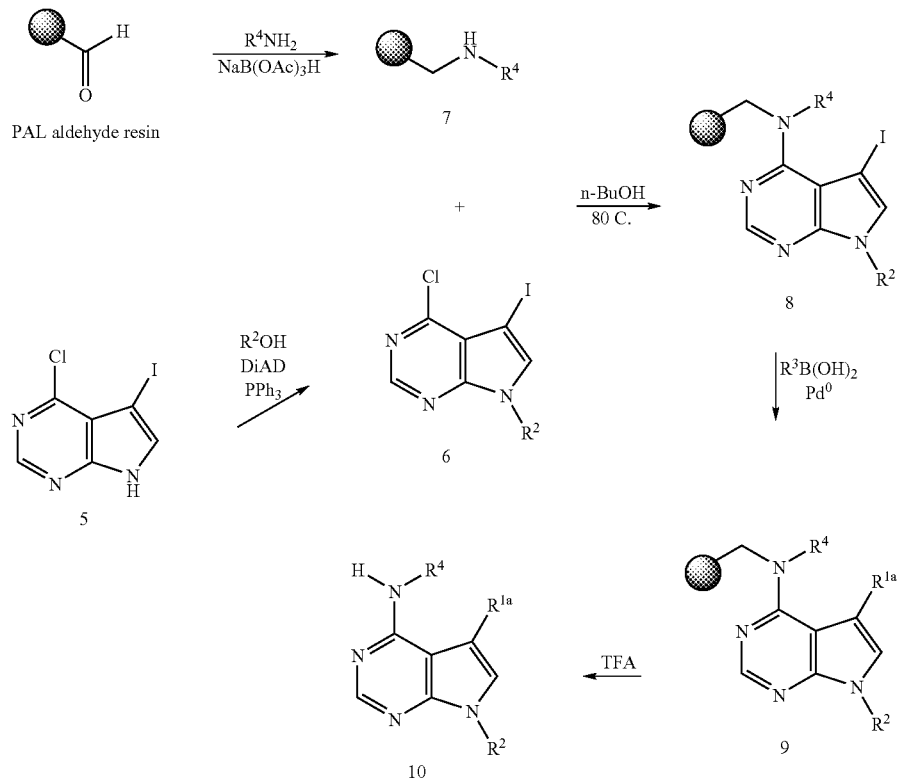

Scheme 1

In Scheme 1, the pyrrolopyrimidine scaffold 4-chloro-5-iodo-7H-pyrrolo[2,3-d]pyrimidine, compound 5, can prepared from ethyl cyanoacetate and bromoacetaldehyde diethyl acetal in six steps (10% yield). $R^2$ is introduced by Mitsunobu alkylation of compound 5, using either solid-phase or solution-phase chemistry, to form compound 6. $R^2$ substituents can also be introduced by anion alkylation or Michael addition. A 4-formyl-3,5-dimethoxyphenoxymethyl-functionalized (PAL) resin is loaded with an $R^4$ appended amine by reductive amination to form compound 7, employing, for example, methylamine, ethylamine, benzylamine or 2,4,6-trimethoxybenzylamine or a suitable salt thereof (such as the hydrogen chloride salt). Compounds 6 and 7 are contacted and heated to allow the SNAR capture of the alkylated scaffold to form compound 8. Using a solid-phase Suzuki coupling employing the appropriate boronic acid and catalyst (such as palladium), $R_{1a}$ is introduced to form compound 2. Alternatively, a solution-phase Suzuki coupling can be employed. Compound 2 is then cleaved from the solid support with trifluoroacetic acid. Scheme 1 can be carried out under similar reaction conditions as a solution-phase synthesis.

When a primary amine at $R^4$ is required, a protecting strategy can be employed. An acid-labile protecting group, such as, for example, 2,4,6-trimethoxybenzylamine, is preferred. Acid labile protecting groups for $R^1$ or $R^2$ substituents can also be employed. Other suitable acid labile-protecting groups commonly used in the art can be found in Greene and Wuts, *Protective Groups in Organic Synthesis,* 2d ed, John Wiley & Sons, New York, 1991, the disclosure of which is hereby incorporated by reference in its entirety.

The compounds of Formula I and the compounds of Formula II of the invention can be prepared as shown in Scheme 2. The compounds of Formula I, where Y is N, can be prepared as generally described in Hanefeld, U., Rees, C. W., White, A. J. P., Williams, D. J., "One-pot Synthesis of Tetrasubstituted Pyrazoles Proof of Regiochemistry," *J. Chem. Soc. Perkin Trans* 1: 1545-1522, 1996, the disclosure of which is incorporated herein by reference in its entirety. Scheme 2 is also applicable where Z=halo or Z=NR$_3$R$_4$, (wherein R$_3$ and R$_4$ are not hydrogen) as demonstrated in Bishop, A. C. *Chemical Genetic Approaches To Highly Selective Protein Kinase Inhibitors,* Ph. D. Doctoral dissertation, Princeton University, 2000, the disclosure of which is incorporated herein by reference in its entirety.

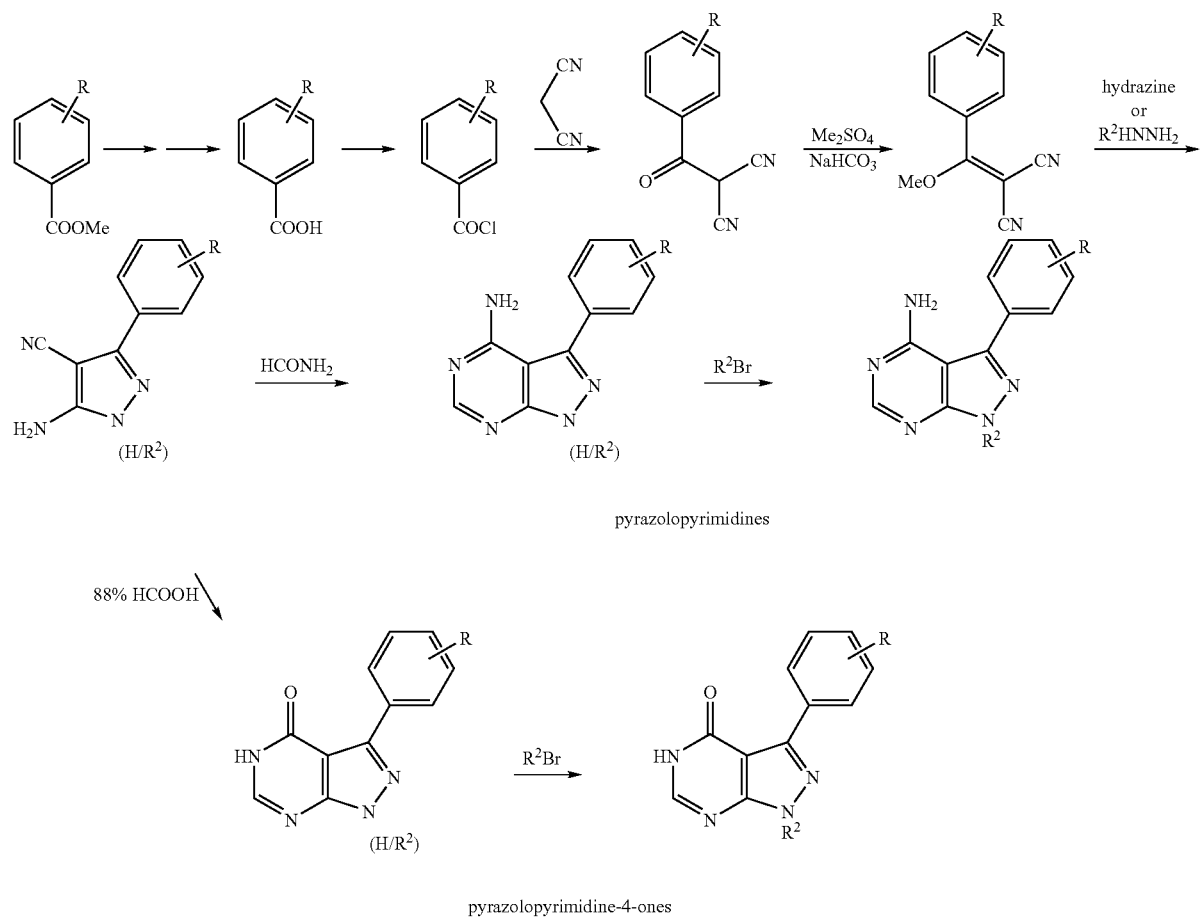

Scheme 2
General scheme for pyrazolopyrimidine and pyrazolopyrimidine-4-one derivatives General scheme for solution phase synthesis of pyrrolopyrimidine inhibitors

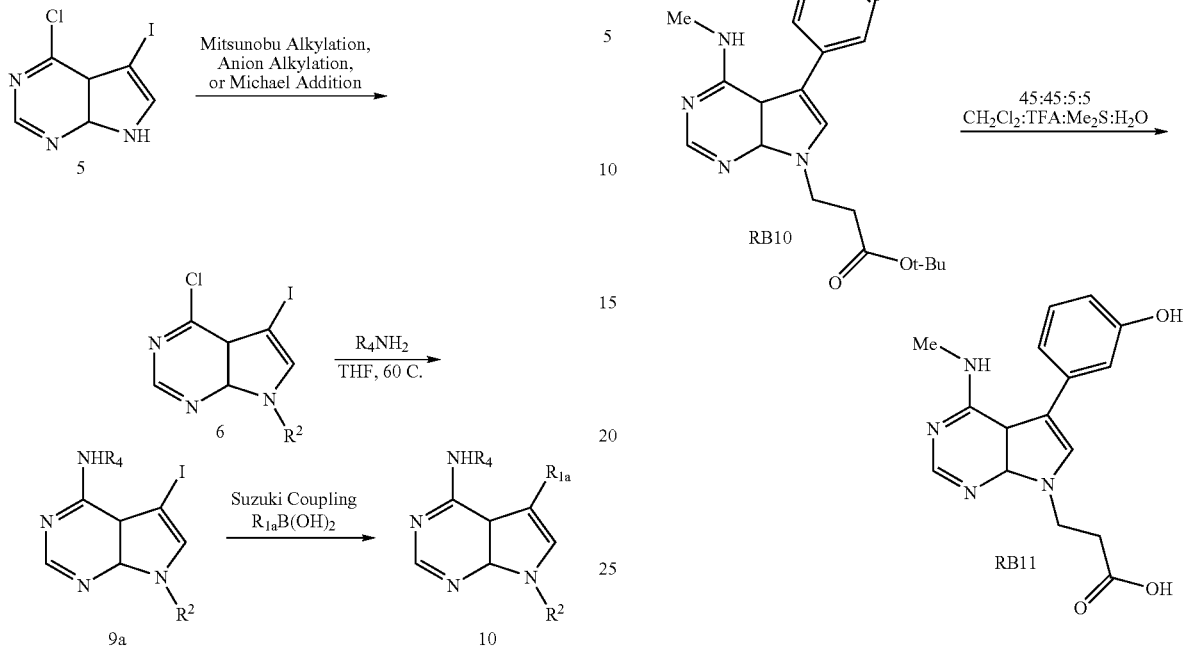

Solution phase synthesis of pyrrolopyrimidine derivatives is carried out using the general scheme above. Reactions are analogous to those employed during solid-phase synthesis. Mitsunobu alkylation, anion alkylation or Michael addition type reactions can be used to introduce $R_2$ substituents in the production of 6. SNaryl reaction of 6 with primary amines, secondary amines or ammonia ($R_4$=H), yields 9a. Suzuki coupling of an aryl boronic acid or boronic ester yields 10. A subsequent deprotection step is required when there are protecting groups as in the case for RB11 synthesis.

General scheme for solution phase synthesis of RB10 and RB11

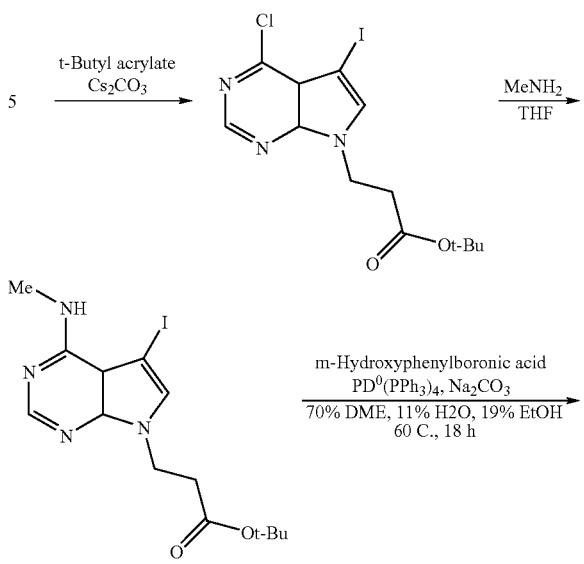

tert-Butyl 3-(4-chloro-5-iodo-4aH-pyrrolo[2,3-d]pyrimidin-7(7aH)-yl)propanoate: The Michael addition was performed as follows: 4-Chloro-7,7a-dihydro-5-iodo-4aH-pyrrolo[2,3-d]pyrimidine (5. 3 g, 0.11 mol) and $Cs_2CO_3$ (5.25 g, 0.016 mol) were p within a 250 ml round bottom flask, and the contents were subject to high vacuum for 20 min. The flask was purged with argon, t-Butylacrylate (30 ml) was added and the reaction was left to stir at room temperature overnight. The reaction was quenched with 100 ml 10% aqueous monosodium citrate, and the organic materials were extracted into ethyl acetate (3×100 ml). The combined organics were dried with sodium sulfate, and evaporated in vacuo to yield a viscous oil. Silica gel chromatography (ethyl acetate:hexanes) and evaporation of the requisite fractions yielded 0.7 g (17.2% yield) of the desired product as a white solid. $^1$H NMR (399.6 MHz, $CDCl_3$) δ 1.38 (9H, s), 2.76 (2H, t, J=6.4 Hz), 4.50 (2H, t, J=6.4 Hz), 7.47 (1H, s), 8.59 (1H, s).

tert-butyl 3-(5-iodo-4-(methylamino)-4aH-pyrrolo[2,3-d]pyrimidin-7(7aH)-yl) propanoate: t-Butyl 3-(4-chloro-5-iodo-4aH-pyrrolo[2,3-d]pyrimidin-7(7aH)-yl)propanoate from above (0.05 g, 0.12 mmol) was placed in a 15 ml pressure tube. 2M methylamine in THF (7 ml) was added and the vessel was sealed and left to stir overnight. The volatiles were evaporated in vacuo, the resultant material was quenched with 20 ml 10% monosodium citrate, and the solution was extracted with ethyl acetate (3×20 ml). The combined organic extracts were dried with sodium sulfate and evaporated in vacuo. The resultant product (0.069 g, 140% yield) was used without further purification. $^1$H NMR (399.6 MHz, $CDCl_3$) δ 1.38 (s), 2.71 (2H, t, J=6.4 Hz), 3.15 (3H, d, J=4.8 Hz), 4.38 (2H, t, J=6.4 Hz), 6.04 (3H, app s), 7.04 (s), 8.33 (s).

tert-Butyl 3-(5-(3-hydroxyphenyl)-4-(methylamino)-4aH-pyrrolo[2,3-d]pyrimidin-7(7aH)-yl)propanoate (RB10): t-butyl 3-(5-iodo-4-(methylamino)-4aH-pyrrolo[2, 3-d]pyrimidin-7(7aH)-yl)propanoate (123 mmol) from above was placed in a 25 ml round bottom flask, whereupon 3.1 ml dimethoxy ethyleneglycol was added. 3-Hydroxyphenylboronic acid (492 mmol pre-dissolved in 0.66 ml ethanol) was added at once, and was followed by 0.5 ml saturated aqueous sodium carbonate. Pd$^0$(PPh$_3$)$_4$ (14 mg, 12 umol) was added to the reaction, the vessel was purged with argon, and set to stir at 80 C overnight. The reaction was subsequently cooled, and filtered through a bed of celite. The filtrate was evaporated in vacuo, and the residual material was adhered to silica gel using ethyl acetate as solvent. Silica gel chromatography (ethyl acetate:hexanes) and evaporation in vacuo of the requisite fractions yielded the desired product. MS m/z=369.22.

3-(5-(3-hydroxyphenyl)-4-(methylamino)-4aH-pyrrolo[2,3-d]pyrimidin-7(7aH)-yl)propanoic acid (RB11): RB10 (9.6 mg, 26 umol) was treated with 2 ml deprotection solution (45% TFA, 45% CH$_2$Cl$_2$, 5% Me$_2$S, 5% H$_2$O) for 1 hr at room temperature. The volatiles were evaporated in vacuo, and 1 ml acetonitrile:water:TFA (1:1:0.002) was added. The resultant solution was purified by reverse-phase HPLC using a linear gradient of water to acetonitrile both containing 0.1% TFA. The requisite fractions were pooled and lyophilized to give the desired product 4.1 mg (79% yield) as a white powder. $^1$H NMR (399.6 MHz, d$^6$-DMSO) δ 2.85 (2H, t, J=6.4 Hz), 3.0 (3H, d, J=4.4 Hz), 4.3, t, J=6.4 Hz), 6.8 (3H, m), 7.27 (1H, app t, J=7.6 Hz), 9.55 (1H, b s) The amino proton resonance was presumably hidden due to the presence of water in the NMR sample.

General scheme for solution phase synthesis of RB6:

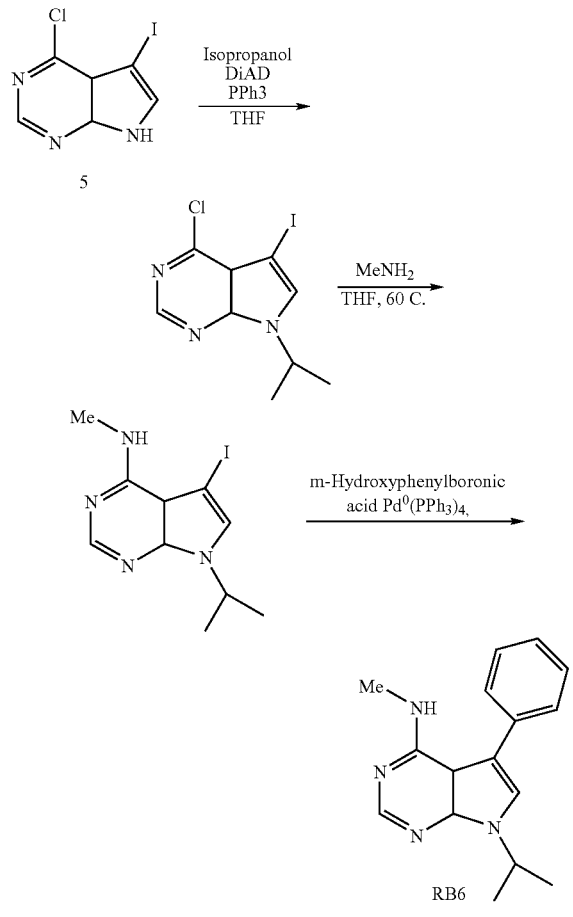

The general solution phase synthetic strategy was used to synthesize RB6 in 3 steps from compound 5. RB8 and RB9 were produced in a similar manner, except benzyamine and dibenzyl amine respectively were used during the S$_N$aryl reaction.

Mitsunobu alkylation of 5 with isopropanol: To a dry 50 ml round bottom flask was added 5 (0.5 g, 1.78 mmol) and PPh$_3$ (0.84 g, 3.2 mmol). The materials were dried under high vacuum for 20 m, and the flask was purged with argon. THF (30 ml) and isopropanol (0.3 ml, 3.9 mmol) were added and the flask was cooled in an ethylene glycol/dry ice bath whereupon DiAD (0.47 g, 2.3 mmol) was added dropwise to the stirred solution. After 18 h, the volatiles were evaporated in vacuo and the resultant oil was dissolved in ethyl acetate (50 ml) and 50% saturated sodium bicarbonate (50 ml). The organics were extracted with ethyl acetate (3×50 ml), dried with sodium sulfate and evaporated in vacuo to yield an orange oil. Silica gel chromatography (ethyl acetate:hexanes) afforded the desired product as a yellow solid (480 mg, 84% yield). $^1$H NMR (399.6 MHz, CDCl$_3$) δ 1.5 (6H, d, J=6.4 Hz), 5.1 (1H, sp, J=6.8 Hz), 7.4 (1H, s), 8.6 (1H, s).

7,7a-Dihydro-5-iodo-7-isopropyl-N-methyl-4aH-pyrrolo[2,3-d]pyrimidin-4-amine: 4-Chloro-7,7a-dihydro-5-iodo-7-isopropyl-4aH-pyrrolo[2,3-d]pyrimidine (0.3 g, 0.93 mmol) from above was placed within a 15 ml pressure tube. 2 M methylamine in THF (15 ml) was added, and the reaction was left to stir overnight. The volatiles were removed in vacuo, and the residue was dissolved in methanol, 5 ml silica gel were added, and the volatiles were removed in vacuo. The adhered product was purified by silica gel chromatography (ethyl acetate:hexanes), and the requisite fractions were pooled and evaporated in vacuo to yield the desired product (0.25 g, 85% yield). $^1$H NMR (399.6 MHz, CDCl$_3$) δ 1.43 (6H, d, J=6.8 Hz), 3.13 (3H, d, J=4.8 Hz), 5.0 (1H, sp, J=6.8 Hz), 7.02 (1H, s), 8.35 (1H, s).

7,7a-Dihydro-7-isopropyl-N-methyl-5-phenyl-4aH-pyrrolo[2,3-d]pyrimidin-4-amine (RB6): 7,7a-Dihydro-5-iodo-7-isopropyl-N-methyl-4aH-pyrrolo[2,3-d]pyrimidin-4-amine (0.15 g, 0.475 mmol) from above was placed in a 50 ml round bottom flask, whereupon 12 ml dimethoxy ethyleneglycol was added. 3-Hydroxyphenylboronic acid (0.262 g, 1.9 mmol pre-dissolved in 3.3 ml ethanol) was added at once, and was followed by 1.9 ml saturated aqueous sodium carbonate. Pd$^0$(PPh$_3$)$_4$ (55 mg, 47 umol) was added to the reaction, the vessel was purged with argon, and set to stir at 80 C for 48 h. The reaction was subsequently cooled, and filtered through a bed of celite. The filtrate was evaporated in vacuo, and the residual material was adhered to silica gel using ethyl acetate as solvent. Silica gel chromatography (ethyl acetate:hexanes) and evaporation in vacuo of the requisite fractions yielded the desired product (94.8 mg, 70.7% yield). $^1$H NMR (399.6 MHz, d$^6$-DMSO) δ 1.76 (6H, d, J=6.8 Hz), 5.03 (3H, d, J=4.8 Hz), 5.34 (1H, sp, J=6.4 Hz), 5.53 (1H, q, J=4.8 Hz), 6.73 (1H, m), 6.85 (1H, m), 7.25 (1H, app t, J=7.6 Hz), 7.37 (1H, s), 7.59 (1H, s).

Anion alkylation of 5 with methyl iodide: To a dry 50 ml round bottom flask was added 5 (0.2 g, 0.7 mmol) and 15 ml dry acetonitrile. The reaction was cooled on ice, and NaH (0.026 g, 1.1 mmol) was added at once. After stirring for 5 m, MeI (0.152 g, 1.07 mmol) was added dropwise. The reaction was allowed to warm to room temperature overnight. The volatiles were evaporated, the residue was dissolved in ethyl acetate:water, and the organics were extracted with ethyl acetate (3×50 ml). The organics were dried with sodium sulfate and evaporated in vacuo. The residue was subject to silica gel chromatography (ethyl acetate:hexanes). The requisite fractions were pooled and evaporated to yield a granular solid (0.12 g, 56% yield). $^1$H NMR (399.6 MHz, CDCl$_3$) δ 3.87 (1H, s), 7.35 (1H, s), 8.62 (1H, s).

33

General scheme for solution phase synthesis of pyrrolopyrimidine inhibitors SD1 through SD8

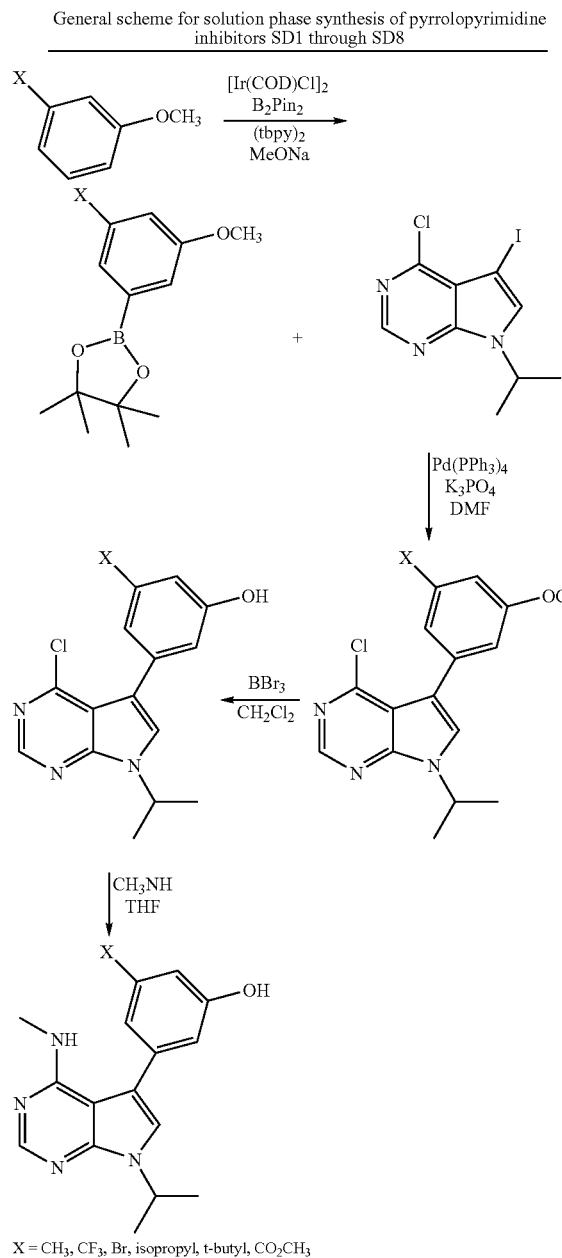

X = CH₃, CF₃, Br, isopropyl, t-butyl, CO₂CH₃

Preparation of 3,5-disubstituted aryl borates.

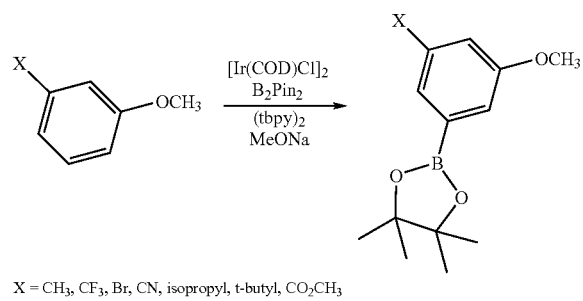

X = CH₃, CF₃, Br, CN, isopropyl, t-butyl, CO₂CH₃

34

3-Substituted anisoles were either purchased from Aldrich (X=CH₃, CF₃, Br) or synthesized from the corresponding phenols (X=isopropyl, t-butyl). Direct borylation was performed according to the general procedures described by Miyaura and Hartwig. Ishiyama, T.; et al., *J. Am. Chem. Soc.*, 124: 390-391, 2002; Ishiyama, T.; et al., *Angew. Chem. Int. Ed.*, 41: 3056-3058, 2002. A typical experimental procedure is given below.

3-Trifluoromethyl- 5-(4,4,5,5-Tetramethyl-1,3,2-dioxaborolan-2-yl)anisole. A flame-dried 100 mL Schlenk tube was charged with bis(pinacolato)diboron (350 mg, 1.38 mmol), [Ir(COD)Cl]₂ (12 mg, 0.018 mmol), sodium methoxide ( 5 mg, 0.09 mmol), and 4,4'-di-tert-butyl-2,2'-dipyridyl (8 mg, 0.03 mmol). The flask was evacuated, placed under argon, and 3-trifluoromethylanisole (2.5 mL) was added. The flask was restoppered and evacuated (full vacuum, 2 minutes). The flask was sealed under vacuum and maintained at 90° C. (oil bath) for 96 h. Thereafter, the contents were transferred to a round bottom flask with the aid of ethyl acetate and purified by Kugelrohr distillation. The product, a viscous oil, distills at 120° C. @10 μm. Isolated yield 497 mg (1.65 mmol, 60%). ¹H NMR (400 MHz, CDCl₃) δ 7.62 (s, 1 H); 7.43 (s, 1 H); 7.18 (s, 1 H); 3.82 (s, 1 H); 1.32 (s, 1 H).

General expeimental procedure for coupling of 3,5-disubstituted aryl borates to scaffolds

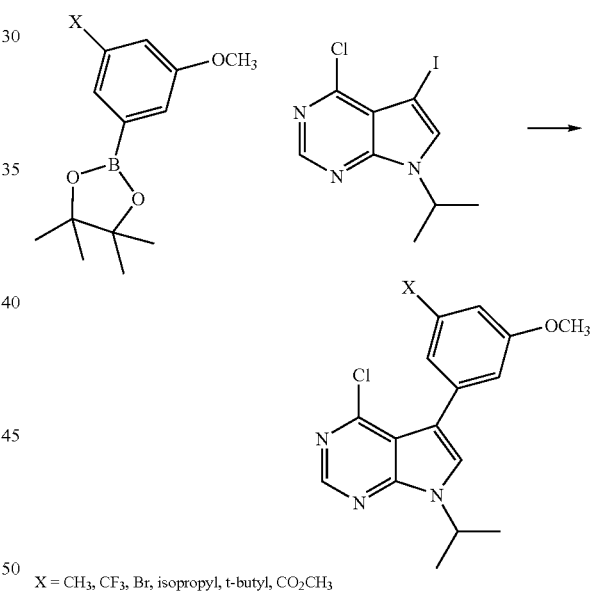

X = CH₃, CF₃, Br, isopropyl, t-butyl, CO₂CH₃

The appropriate aryl pinacol borate (0.1 mmol) and iodinated substrate (0.1 mmol) were dissolved in acetone and transferred to a Schlenk flask. The solvent was evaporated and the flask was charged with Pd(PPh₃)₄ (3 mg) and K₃PO₄ (100 mg). The flask was evacuated, placed under argon, and charged with 5 mL of degassed anhydrous DMF. The resulting solution was heated at 60° C. for 24 h under argon. Water was added and the mixture was extracted (3×10 mL) with ethyl acetate. The combined organic fractions were washed with water and saturated aqueous NaCl, dried over Na₂SO₄, and evaporated. The remaining material was loaded unto a small (0.5 cm×8 cm) silica gel column and eluted with 1:4 ethyl acetate:hexane solution. Isolated yields ranged from 50% to 90%.

X=CH₃ ¹H NMR (400 MHz, CDCl₃) δ 8.62 (s, 1 H); 7.32 (s, 1 H); 6.91 (s, 1 H); 6.87 (s, 1 H); 6.73 (s, 1 H); 5.18 (septet, 1 H, J=6.8 Hz); 3.82 (s, 3 H); 2.37 (s, 3 H); 1.54 (d, 6 H, J=6.8 Hz).

X=CF₃ ¹H NMR (400 MHz, CDCl₃) δ 8.64 (s, 1 H); 7.37 (s, 1 H); 7.34 (s, 1 H); 7.23 (s, 1 H); 7.11 (s, 1 H); 5.19 (septet, 1 H, J=6.7 Hz); 3.88 (s, 3 H); 1.56 (d, 6 H J=6.7 Hz).

X=Br ¹H NMR (400 MHz, CDCl₃) δ 8.63 (s, 1 H); 7.33 (s, 1 H); 7.23 (s, 1 H); 7.04 (s, 1 H); 6.99 (s, 1 H); 5.18 (septet, 1 H, J=6.8 Hz); 3.83 (s, 3 H); 1.55 (d, 6 H, J=6.8 Hz);

X=tert-butyl ¹H NMR (400 MHz, CDCl₃) δ 8.61 (s, 1 H); 7.33 (s, 1 H); 7.15 (s, 1H); 6.91 (s, 1 H); 6.82 (s, 1 H); 5.18 (septet, 1 H, J=6.8 Hz); 3.81 (s, 3 H); 1.56 (d, 6 H, J=6.8 Hz); 1.35 (s, 9 H).

X=CO₂CH₃ ¹H NMR (400 MHz, CDCl₃) δ 8.63 (s, 1 H); 7.76 (t, 1 H, J=1.4 Hz); 7.54 (dd, 1 H, J₁=2.4 Hz, J₁=1.4 Hz); 7.36 (s, 1 H); 7.26 (dd, 1 H, J₁=2.4 Hz, J₁=1.4 Hz); 5.18 (septet, 1 H, J=6.8 Hz); 3.91 (s, 3 H); 3.88 (s, 3 H); 1.55 (d, 6 H, J=6.8 Hz).

General experimental procedure for demethylation of inhibitors

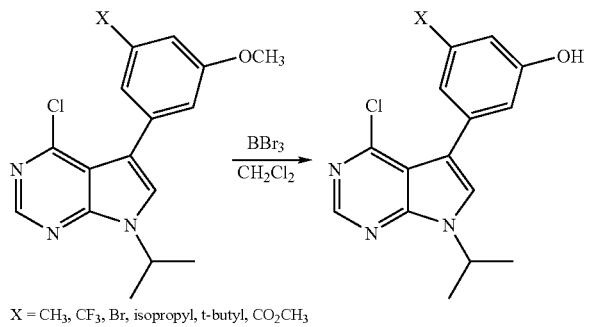

X = CH₃, CF₃, Br, isopropyl, t-butyl, CO₂CH₃

General Procedure: The anisole derivative (20 mg) was dissolved in methylene chloride (5 mL) and transferred to an argon flushed Schlenk tube. The solution was chilled to 0° C. before 1 mL of a BBr3 solution (1 M in CH2Cl2) was added. The mixture was stirred at 0° C. for 2 h. Saturated aqueous NaHCO₃ was added, the biphasic mixture was stirred for 15 min, extracted with CH₂Cl₂, and the organic extracts were dried over Na2SO4. The solvent was evaporated and the organic residue was purified by flash chromatography on silica gel (1:1 hexane:ethyl acetate eluant). Isolated yields were in excess of 80%.

X=CH3; 1H NMR (400 MHz, CDCl3) δ 8.62 (s, 1 H); 7.31 (s, 1 H); 6.87 (s, 1 H); 6.81 (s, 1 H); 6.69 (s, 1 H); 5.77 (broad singlet, 1 H); 5.17 (septet, 1 H, J=6.7 Hz); 2.34 (s, 3 H); 1.54 (d, 6 H, J=6.7 Hz).

X=CF3; 1H NMR (400 MHz, CDCl3) δ 8.66 (s, 1 H); 7.40 (s, 1 H); 7.28 (s, 1 H); 7.20 (s, 1 H); 7.11 (s, 1 H); 5.19 (septet, 1 H, J=6.8 Hz); 1.56 (d, 6 H J=6.8 Hz).

X=Br; 1H NMR (400 MHz, CDCl3) δ 8.32 (s, 1 H); 7.09 (s, 1 H); 7.09 (s, 1 H); 7.00 (s, 1 H); 6.65 (s, 1 H); 5.27 (broad quart., 1 H, J=4.6); 5.03 (septet, 1 H, J=6.8 Hz); 3.12 (d, 3 H, J=4.6 Hz); 1.48 (d, 6 H, J=6.8 Hz).

X=tert-butyl; 1H NMR (400 MHz, CDCl3) δ 8.64 (s, 1 H); 7.35 (s, 1 H); 7.08 (s, 1 H); 6.88 (s, 1 H); 6.80 (s, 1 H); 5.19 (septet, 1 H, J=6.7 Hz); 3.19 (d, 3 H, J=4.6 Hz) 1.52 (d, 6 H, J=6.7 Hz); 1.34 (s, 9 H).

General experiment procedure for methylamination

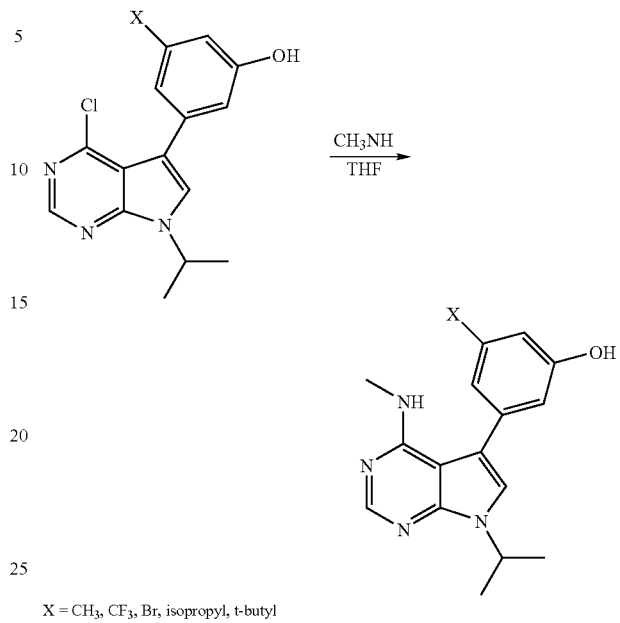

X = CH₃, CF₃, Br, isopropyl, t-butyl

General Procedure: Each compound (20 mg) was dissolved in 5 mL of a THF solution containing methyl amine (1 M) and transferred to an argon flushed 50 mL Schlenk storage tube. The vessel was sealed and heated at 60° C. for 24 h. The THF was evaporated and the remainder was partitioned between ethyl acetate and aqueous bicarbonate solution. The biphasic mixture was extracted with ethyl acetate and the combined organic extracts were dried over Na₂SO₄. The solvent was evaporated and the organic residue was purified by flash chromatography on silica gel (1:3 hexane:ethyl acetate eluant). Isolated yields were in excess of 80%.

X=CH₃ ¹H NMR (400 MHz, CDCl₃) δ 8.38 (s, 1 H); 7.02 (s, 1 H); 6.75 (s, 1 H); 6.75 (s, 1 H); 6.71 (s, 1 H); 5.67 (broad s, 1 H); 5.07 (septet, 1 H, J=6.7 Hz); 3.16 (broad d, 3 H, J=4.7 Hz); 2.34 (s, 3 H) 1.48 (d, 6 H, J=6.7 Hz).

X=CF₃ ¹H NMR (400 MHz, CDCl₃) δ 8.38 (s, 1 H); 7.19 (s, 1 H); 7.15 (s, 1 H); 7.10 (s, 1 H); 7.10 (s, 1 H); 5.50 (broad s, 1 H); 5.09 (septet, 1 H, J=6.7 Hz); 3.20 (d, 3 H, 4.9 Hz) 1.52 (d, 6 H J=6.7 Hz).

X=Br ¹H NMR (400 MHz, CDCl₃) δ 8.64 (s, 1 H); 7.35 (s, 1 H); 7.19 (t, 1 H, J=1.5 Hz); 7.04 (t, 1 H, J=2.0 Hz); 6.95 (dd, 1 H, J₁=2.0 Hz, J₂=1.5 Hz); 5.17 (septet, 1 H, J=6.8 Hz); 1.54 (d, 6 H, J=6.8 Hz).

X=t-butyl ¹H NMR (400 MHz, CDCl₃) δ 8.42 (s, 1 H); 7.06 (s, 1 H); 6.96 (s, 1 H); 6.94 (s, 1 H); 6.82 (s, 1 H); 5.25 (broad s, 1 H) 5.10 (septet, 1 H, J=6.7 Hz); 3.81 (s, 3 H); 1.55 (d, 6 H, J=6.8Hz); 1.32 (s, 9 H).

Other embodiments and uses will be apparent to one skilled in the art in light of the present disclosures.

Exemplary Embodiments

Figure 3:
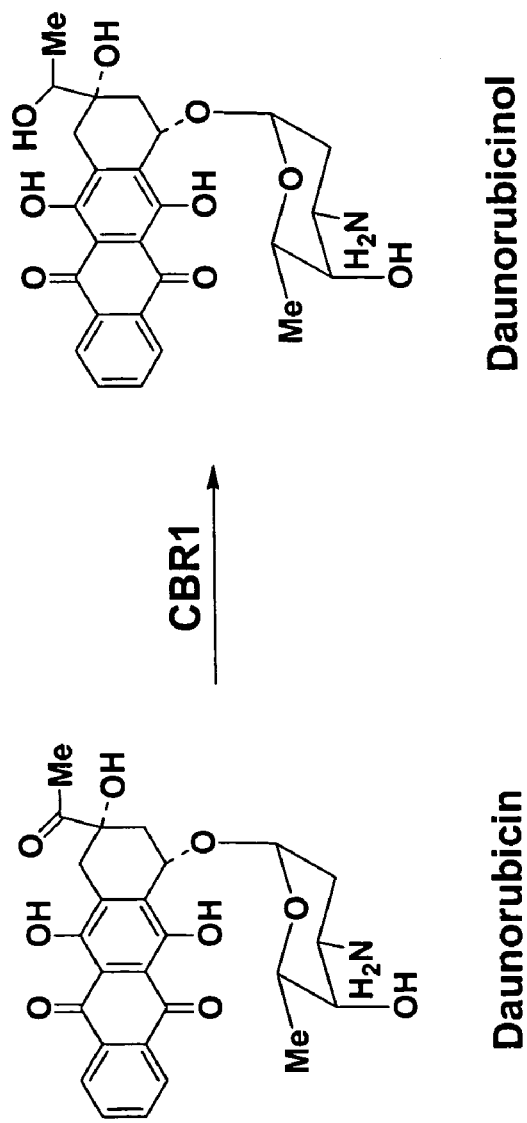
FIG. 3 shows enzymatic activity of carbonyl reductase 1 (CBR1) on daunorubicin.

Development of potent and selective inhibitors of individual SDR family members have the potential to increase the local concentration of endogenous hormones with important therapeutic benefits such as cortisol as an anti-inflammatory agent (11β-hydroxysteroid dehydrogenase II), or to block production of potent chemoattractants such as prostaglandin E2 for blocking colon cancer or metastatic cancer (Carbonyl reductase 1; FIG. 1) (Forrest, G. L. et al., *Chem Biol Interact*, 129: 21-40, 2000), or for degradation of agents that cause obesity or glucose intolerance leading to insulin resistant diabetes such as cortisone (11β-hydroxysteroid dehydrogenase I; FIG. 2) (Oppermann, U. C., et al., *Chem Biol Interact*, 130-132(1-3): 699-705, 2001). Of particular focus here is the potential for blocking the action of Carbonyl Reductase 1, which is responsible for the reduction of the C-13 keto group of the anthracycline anti-cancer agents (daunorubicin: Cerubidin®, DaunoXome®; doxorubicin: Adriamycin®) (FIG. 3). The reduction of C-13 keto of adriamycin, inactivates the anti-cancer activity of daunorubicin and produces a product (daunorubicinol) which is known to be cardiotoxic. Thus, blocking the action of CBR1 in patients treated with adriamycin, would be predicted to enhance the potency of adriamycin's anti-cancer activity and also to reduce the harmful cardiotoxic effects of the adriamycin metabolite (daunorubicinol). Thus, the SDR family members represent an important class of enzymes critical for control of the biological activity of a wide variety of endogenous and xenobiotics compounds. By designing inhibitors of individual members of this family of enzymes new therapies for lung cancer, breast cancer, obesity, diabetes, and for improving the activity and decreasing the toxicity of existing anti-cancer drugs should be possible.

Figure 4:
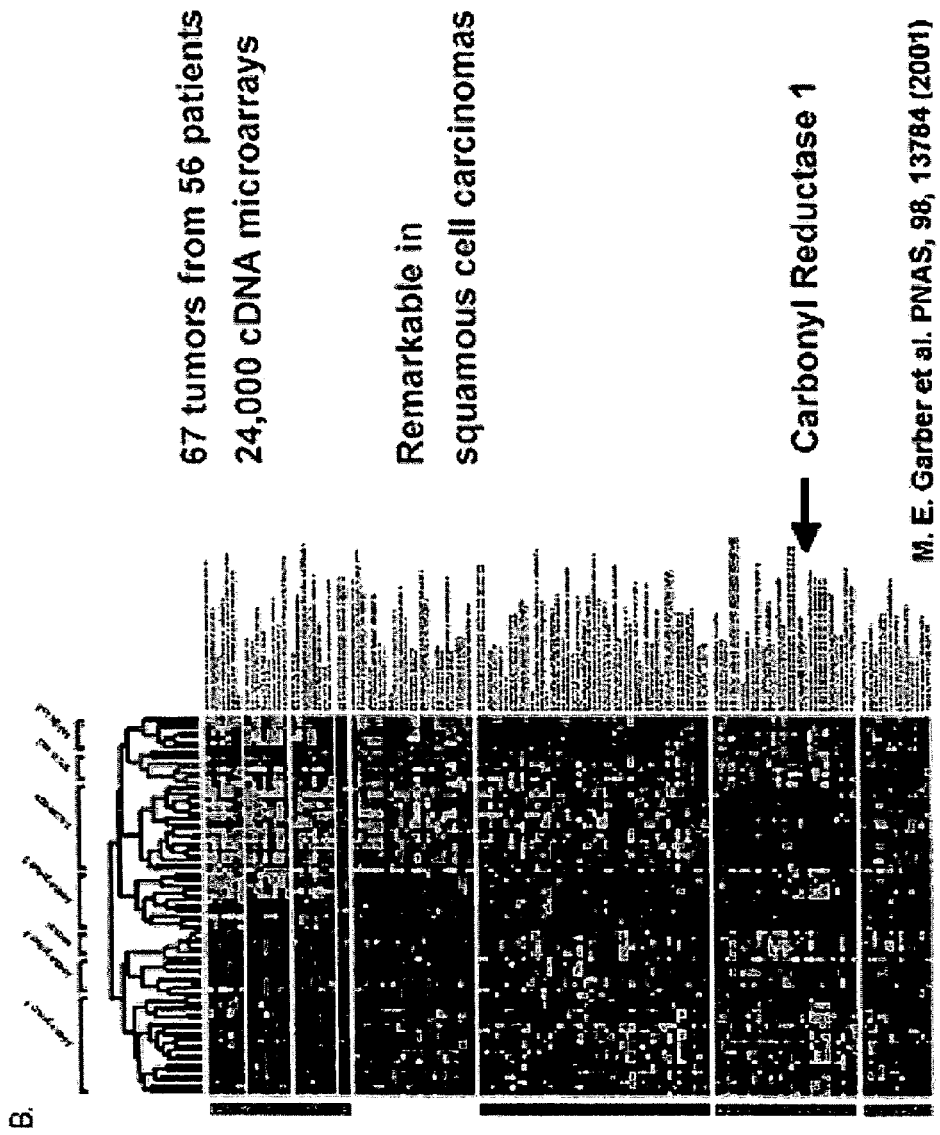
FIG. 4 shows carbonyl reductase 1 (CBR1) is up-regulated in some classes of lung tumors.

Microarray studies (67 tumors from 56 patients) show that CBR1 is upregulated in squamous cell lung carcinoma, but not in small cell lung carcinoma, (FIG. 4; M. E. Garber et al., *Proc. Nat. Acad. Sci USA*, 98: 13784, 2001) leading to the hypothesis that AB129 kills such cells by inhibiting CBR1.

Figure 6:
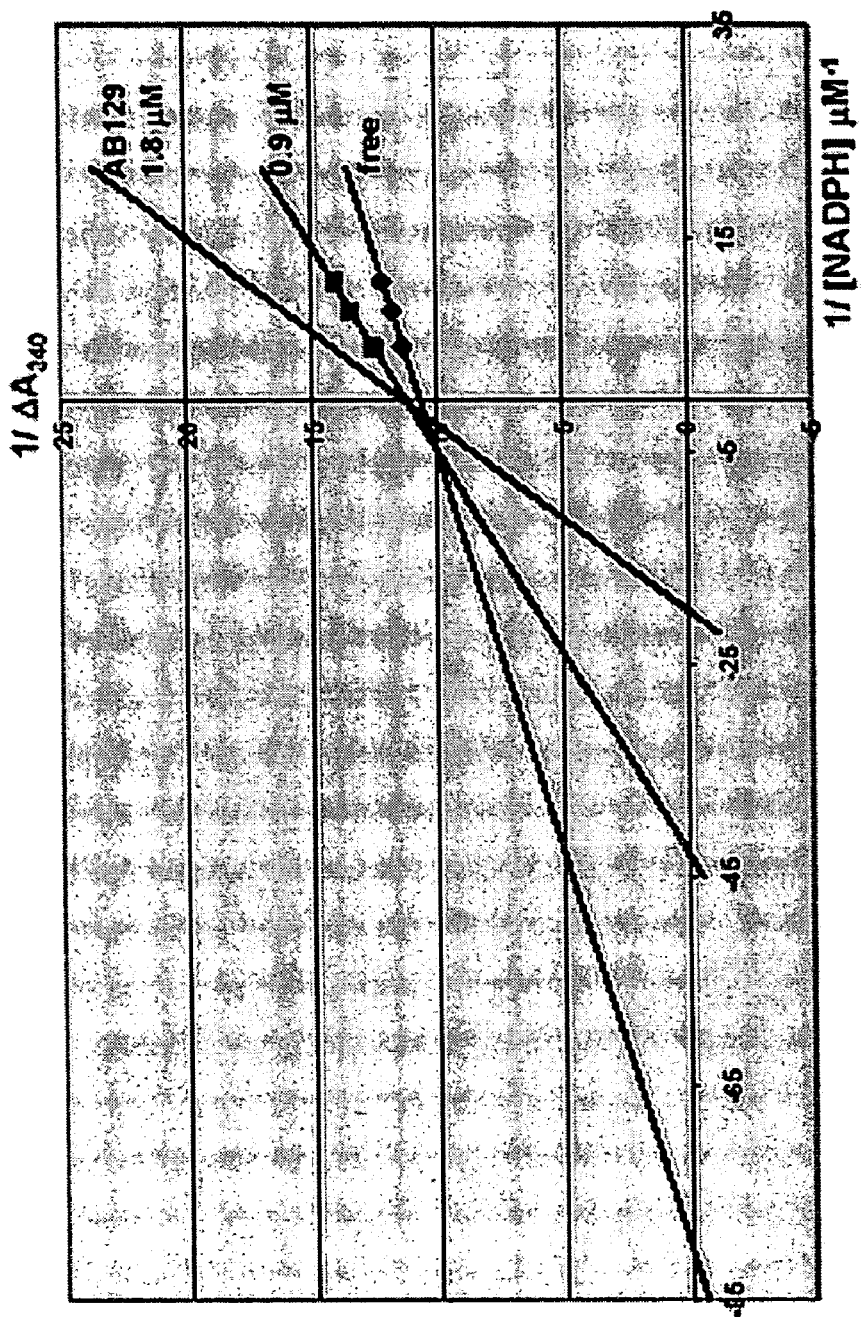
FIG. 6 shows kinetic analysis of carbonyl reductase 1 (CBR1).

Inhibitory activity of AB129 has been demonstrated by measuring reduction of menadione to mendadiol by carbonyl reductase 1 (CBR1). AB129 inhibits the CBR1 catalyzed reduction of menadione by NADPH. The $IC_{50}$ for AB129 was approximately 5 μM. PP1 did not inhibit CBR1. (FIG. 5) At a concentration as high as 16 μM. AB129 is a competitive inhibitor of CBR1, with respect to NADPH (FIG. 6).

Figure 8:
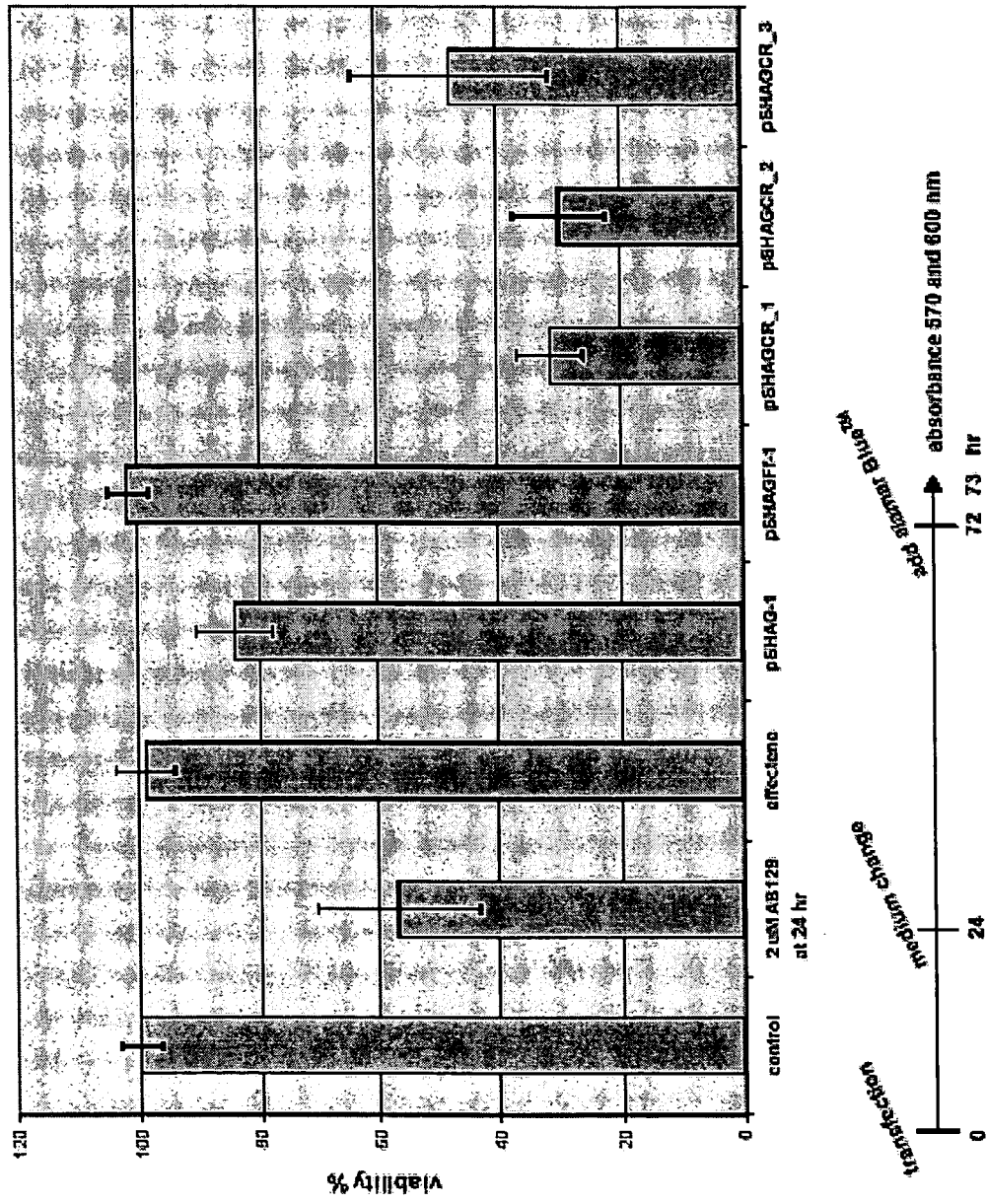
FIG. 8 shows carbonyl reductase 1 (CBR1) is required for A549 lung carcinoma cell viability.

Experiments using interfering RNA (RNAi) downregulate CBR1 by inhibiting translation of mRNA in A549 lung carcinoma cells and demonstrate that CBR1 has a role in development of lung cancer. RNAi inhibition of CBR1 translation demonstrates a 60 to 70% decrease in viability of A549 lung carcinoma cells compared to an approximately 50% decrease in viability of A549 cells in the presence of AB129. (FIGS. 7 and 8) This suggests that inhibition of CBR1 expression in A549 cells decreases cell viability.

EXAMPLE 1

The SDR Family Member 11β-Hydroxysteroid Dehydrogenase 2 (11β-HSD2) Controls the Local Metabolism of Glucocorticoids and Directly Regulates Tissue Specific Nuclear Hormone Signaling Classical small molecule ligand/receptor pairs in biology interact when both are present in the same tissue and are structurally complementary to one another. An important exception to this paradigm is that of the mineralcorticoid receptor which binds both cortisol and aldosterone (Funder, J. W., et al., *Science*, 242: 583-5, 1988). In the kidney, the mineralcorticoid receptor regulates $K^+$ uptake and water absorption, in response to the rennin-angiotensin-aldosterone signaling cascade. However, since blood concentrations of cortisol are 100-1000 fold greater than aldosterone, the mineralcorticoid receptor must be "protected" from activation by cortisol in order to allow proper regulation by aldosterone. This "protective" function is carried out by 11β-HSD2 co-localized with the mineralcorticoid receptor, which converts cortisol to cortisone, a steroid hormone which has no binding affinity for the mineralcorticoid receptor (FIG. 2) (Funder, J. W., et al., *Science*, 242: 583-5, 1988). Congenital loss of this enzyme causes apparent mineralcorticoid receptor excess, due to overstimulation of the mineralcorticoid receptor by cortisol, bypassing its normal regulation by aldosterone (White, P. C., et al., *Endocr Rev*, 18: 135-56, 1997). This unusual mechanism of nuclear receptor ligand regulation suggests a potentially new therapeutic approach to treat asthma.

EXAMPLE 2

Targeting 11β-Hydroxysteroid Dehydrogenase 2 (11β-HSD2) as a Potential Alternative to Synthetic Corticosteroid Treatment of Asthma Tissue specific metabolism of steroids is an important factor in regulating the properties of endogenous steroids, perhaps drugs which inhibit these enzymes could effectively regulate the local concentrations of beneficial endogenous hormones. In asthma, local administration of an inhibitor of 11β-HSD2 in the lung would block conversion of the anti-inflammatory steroid, cortisol to inactive cortisone, thus providing a larger concentration of the body's own anti-inflammatory agent to reduce bronchial swelling in this tissue. One potential benefit is that cortisol in the lung would remain regulatable by tissue specific metabolizing enzymes outside of the lung. Synthetic glucocorticoids currently used in asthma therapy are not metabolized by these enzymes, and thus can show pleiotropic effects in other tissues if dosages are not controlled (Barnes, P. J. et al., *Am Rev Respir Dis*, 148: S1-26, 1993). Thus, the strategy proposed here, can avoid the complications of administration of synthetic corticosteroids to patients which can cause high blood pressure, swelling, changes of mood and weight gain, all of which are known functions of cortisol in the body, but which are unwanted side-effects for asthma patients.

The strategy of regulating the metabolism of cortisol through 11β-HSD2 inhibition in the lung is less prone to unwanted side-effects than synthetic glucocorticoid therapy, even though both act through glucocorticoid receptors which are present throughout the body. Vastly different levels of 11β-HSD2 are expressed in the lung compared to other organs, providing an avenue for potent inhibition in the lung without significant inhibition systemically. 11β-HSD2 is expressed at significantly lower levels in the lung compared to the kidney, adrenal and colon (Romero, D. G., et al., *J Steroid Biochem Mol Biol*, 72: 231-7, 2000). One caveat is that only the mRNA levels have been reported which may not directly correspond to a difference in 11β-HSD2 protein levels. By administering a relatively low dose of an 11β-HSD2 inhibitor directly in the lung (intratracheal in the mouse, or with a nebulizer in patients), a significant inhibition of 11β-HSD2 is achieved in the lung, resulting in a significant increase of cortisol concentration. Any of the inhibitor which is absorbed systemically will encounter much larger concentrations of 11β-HSD2, and thus will be unable to significantly perturb 11β-HSD2 function in these tissues, resulting in less severe side-effects compared to synthetic glucocorticoid therapy. Thus, the different levels of 11β-HSD2 expression in the lung can provide additional control over unwanted systemic glucocorticoid stimulation in asthma patients.

EXAMPLE 3

Figure 9:
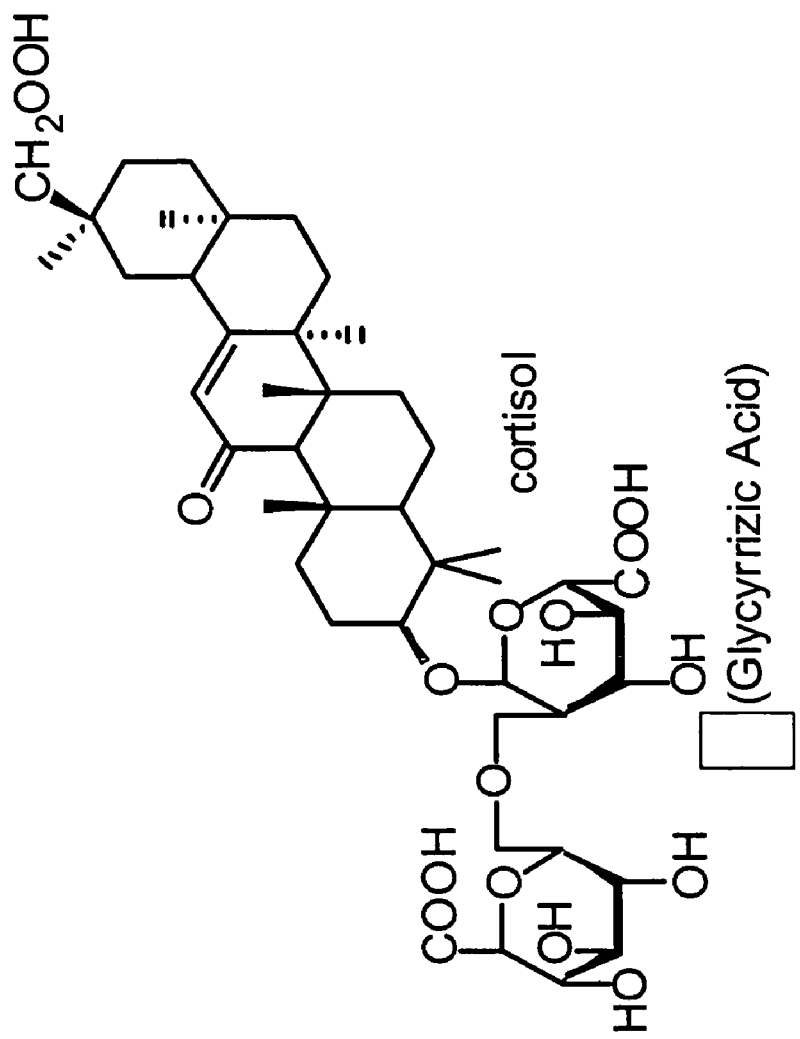
FIG. 9 shows the structure of glycyrrizic acid.

Evidence Linking 11β-Hydroxysteroid Dehydrogenase 2 (11β-HSD2) Inhibition as a Therapy for Asthma Schleimer and coworkers have suggested 11β-HSD2 is an attractive target for treatment of asthma (Feinstein, M. B. et al., *Am J Respir Cell Mol Biol*, 21: 403-8, 1999). They point out that a natural product isolated from licorice is an ancient therapy for asthma and many other inflammatory diseases such as eczema and Addison's disease (Persson, C. G., *Pulm Pharmacol*, 2: 163-6, 1989). The major bioactive component of licorice, glycyrrhizic acid, is in fact an inhibitor of 11β-HSD2 ($IC_{50}$=8 nM) (FIG. 9) (Diederich, S., e al., *Eur J Endocrinol*, 142: 200-7, 2000). Schleimer and coworkers first confirmed that 11β-HSD2 is present in lung epithelial cells, and that cortisol is rapidly oxidized to cortisone in this tissue. Next, they confirmed that glycyrrhizic acid's anti-inflammatory activity in cells is dependent on the presence of 11β-HSD2, further supporting the link between this natural product and 11β-HSD2. Unfortunately, glycyrrhizic acid is not likely to be a very good asthma therapy because of its non-selective nature. It inhibits 11β-HSD1, which blocks production of cortisol from cortisone, resulting in a reduction of anti-inflammatory cortisol concentration, at almost equivalent potency to its inhibition of 11β-HSD1 ($IC_{50}$=40 nM) (Diederich, S., e al., *Eur J Endocrinol*, 142: 200-7, 2000). In fact, recent studies with a derivative of glycyrrhizic acid, carbenoxolone, with similar potency and specificity for 11β-HSD1 and 2 (FIG. 2), has shown potent inhibition of 11β-HSD2 in men with type 2 diabetes (11β-HSD2 inhibition was not measured) (Andrews, R. C., et al., *J Clin Endocrinol Metab*, 88: 285-91, 2003).

Glycyrrhizic acid's non-selective nature is due to its interaction with the glucocorticoid binding pocket of 11β-HSD 1 & 2 which is conserved between the two enzymes. In fact, both enzymes can operate as a reductase or an oxidase, catalyzing both formation and degradation of cortisol. In the body, the directionality of each enzyme is controlled by regulation of re-dox cofactor concentration with NADPH preferred by 11β-HSD1 and $NAD^+$ preferred by 11β-HSD2 (Diederich, S., e al., *Eur J Endocrinol*, 142: 200-7, 2000). A highly selective 11β-HSD2 inhibitor is developed by targeting the $NAD^+$ binding pocket of 11β-HSD2 which is differentiated from that of 11β-HSD 1 by the preference of 11β-HSD2 for $NAD^+$ as a cofactor and preference of 11β-HSD 1 for NADPH. In fact, a similar approach has been successfully used to design selective inhibitors of 11β-HSD 1, which is an attractive drug target for treatment of obesity and insulin resistant diabetes (Barf, T., et al., *J Med Chem*, 45: 3813-5, 2002). The same strategy is applied for treatment of asthma by targeting 11β-HSD2.

EXAMPLE 4

Discovery of an Inhibitor of the SDR Family Member, Carbonyl Reductase 1 (CBR1)

Figure 11:
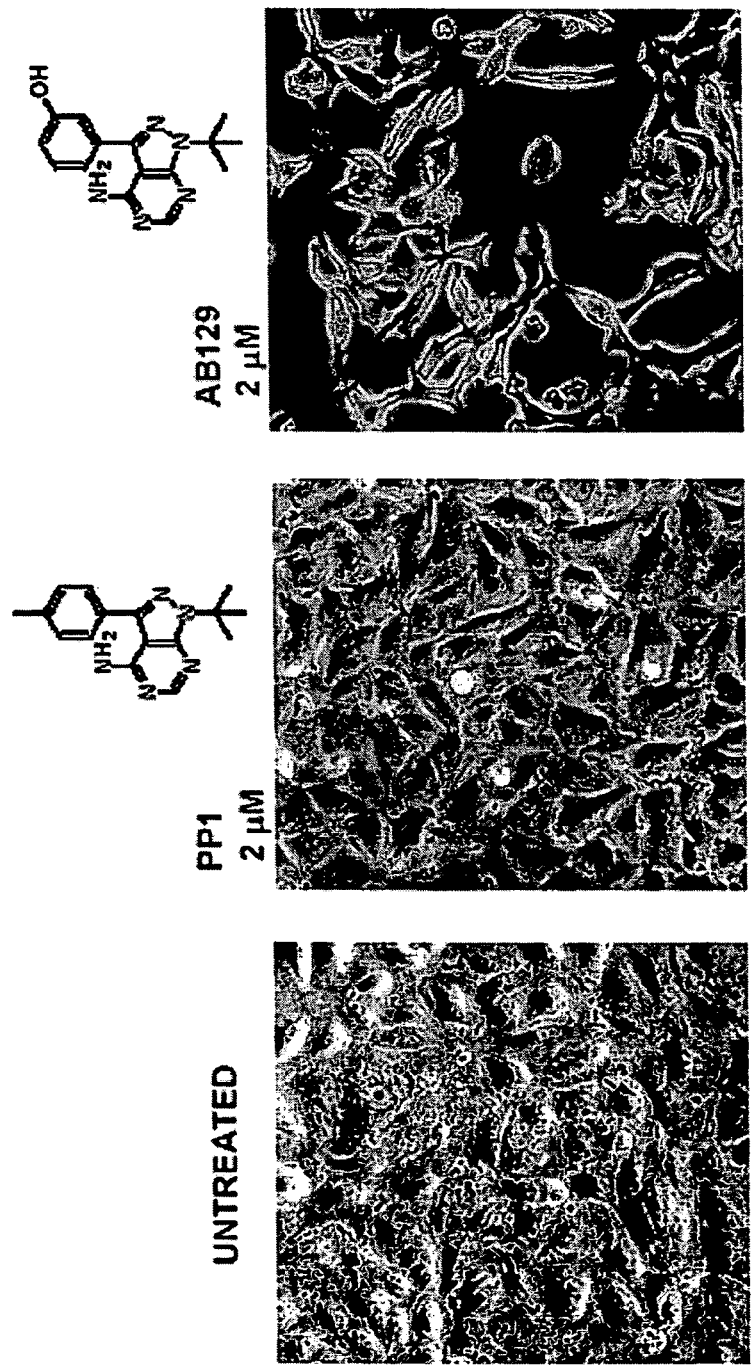
FIG. 11 shows that AB129 causes a morphological change in human lung carcinoma cells.
Figure 12:
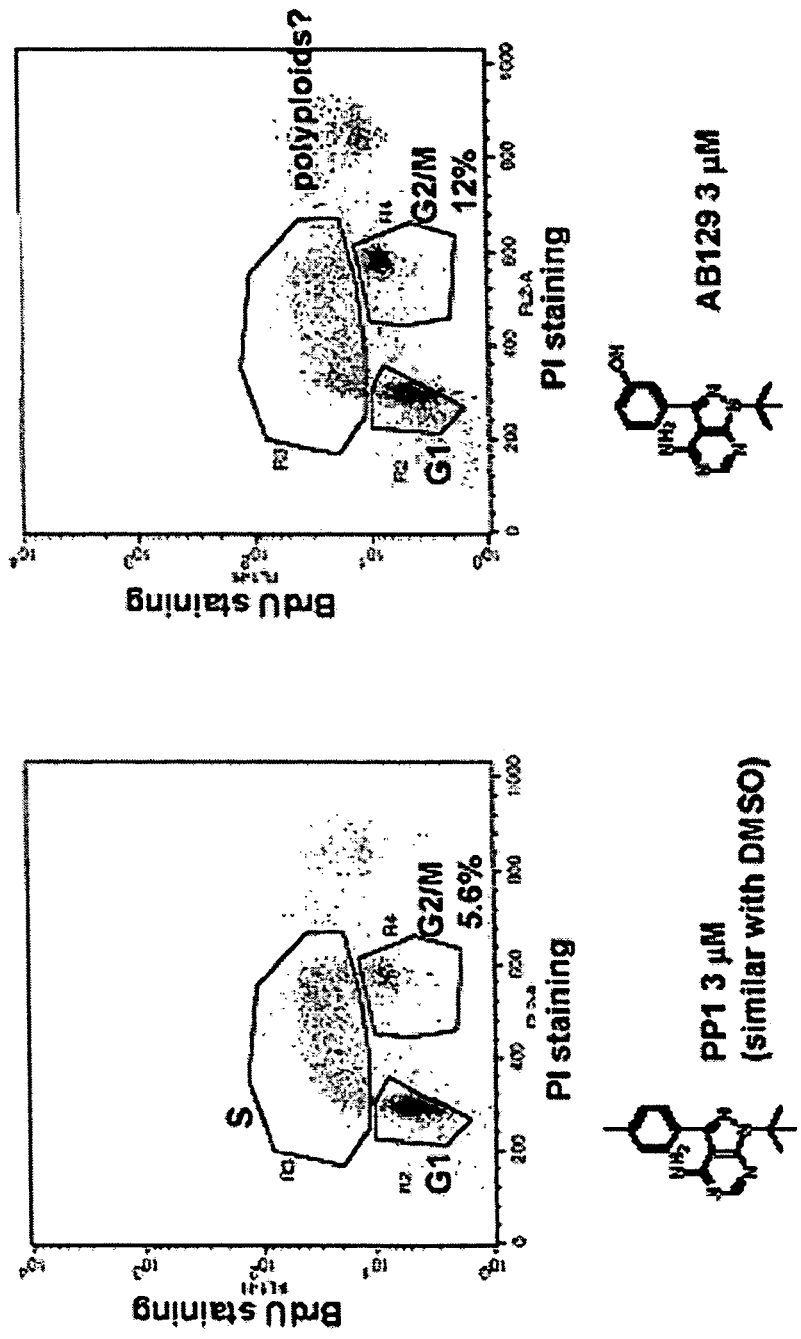
FIG. 12 shows effects of AB129 on cell cycle of A549 lung carcinoma cells.

Three structurally similar compounds (AB129, 1, AB60, 3, and AB61, 4), but not PP1, 2 (FIG. 10) were found to cause mild to severe cell killing in the human lung cancer cell line, A549. (FIG. 11) AB129 affects the cell cycle in A549 cells with approximately 12% of A549 cells in G2/M phase, whereas PP1-treated A549 cells have approximately 5.6% of cells in G2/M phase. AB129 treated cells show a proportion of cells that may be polyploid. (FIG. 12). Many small molecules with cell killing activity on cancer cell lines have been described to date (REFs) yet often the targets of the small molecules cannot be identified because the compounds bind poorly (>1 μM Kd) to the targets, or the targets are expressed at very low abundance (<100,000 copies/cell), or derivatization of the small molecule necessary for attachment of an affinity tag (biotin) or attachment to a bead (for affinity purification of the target protein) reduces the cellular activity and thus ability to bind the target. A strategy was pursued to identify the target or targets of the AB129, AB60, and AB61 compounds based on affinity chromatography.

Figure 13:
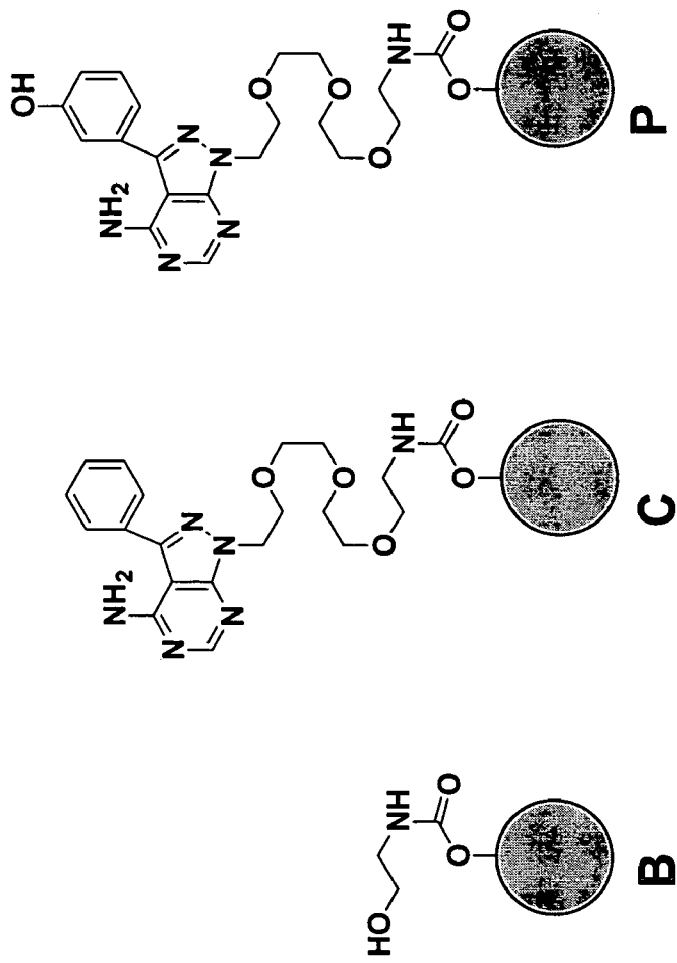
FIG. 13 shows probes for an affinity experiment to identify AB129 target.
Figure 14:
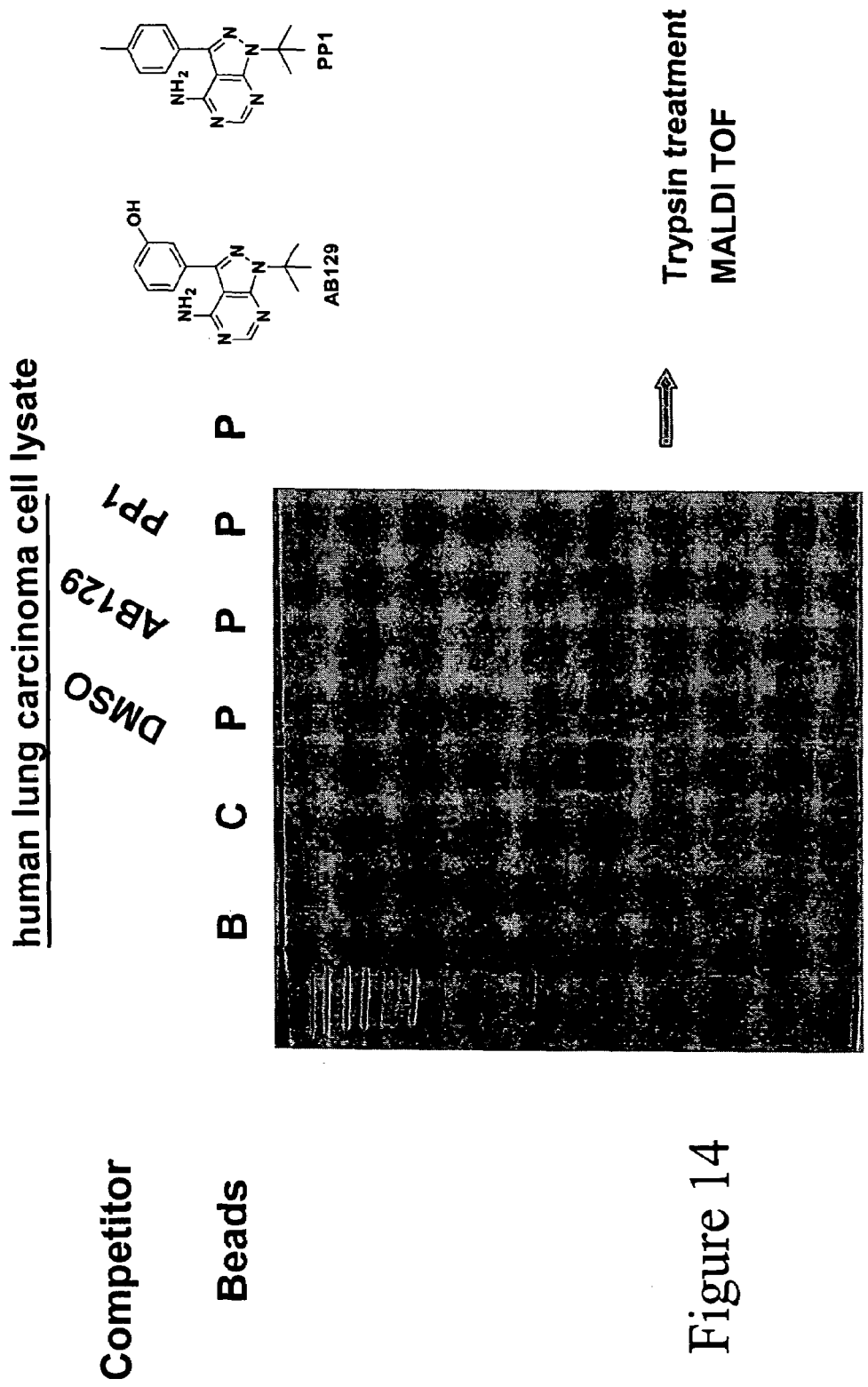
FIG. 14 shows an affinity experiment using A549 lung carcinoma cell lysate.
Figure 15:
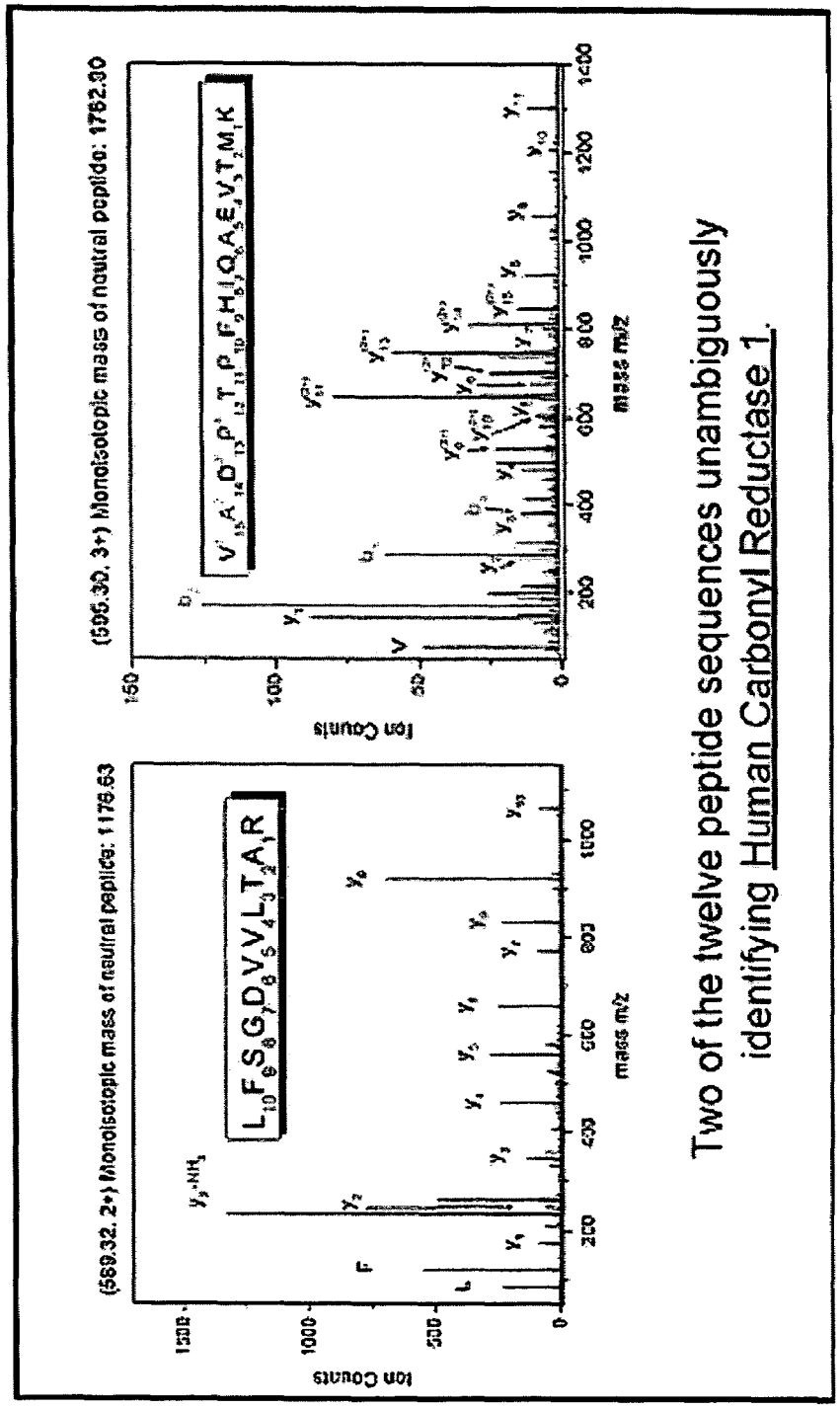
FIG. 15 shows protein identification by collision induced dissociation mass spectrometry (LC/MS/MS).
Figure 16:
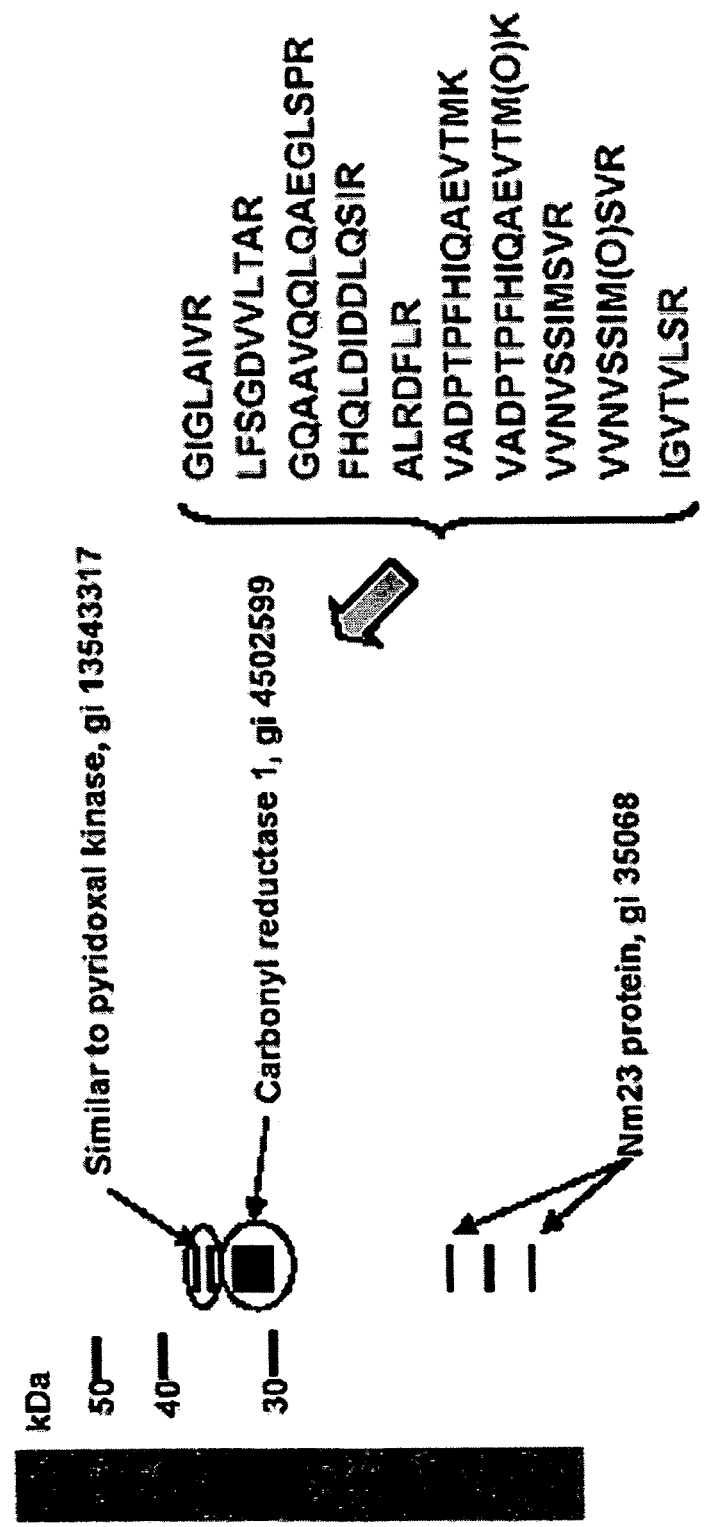
FIG. 16 shows amino acid sequence identification of trypsin digest by mass spectrometry.
Figure 17:
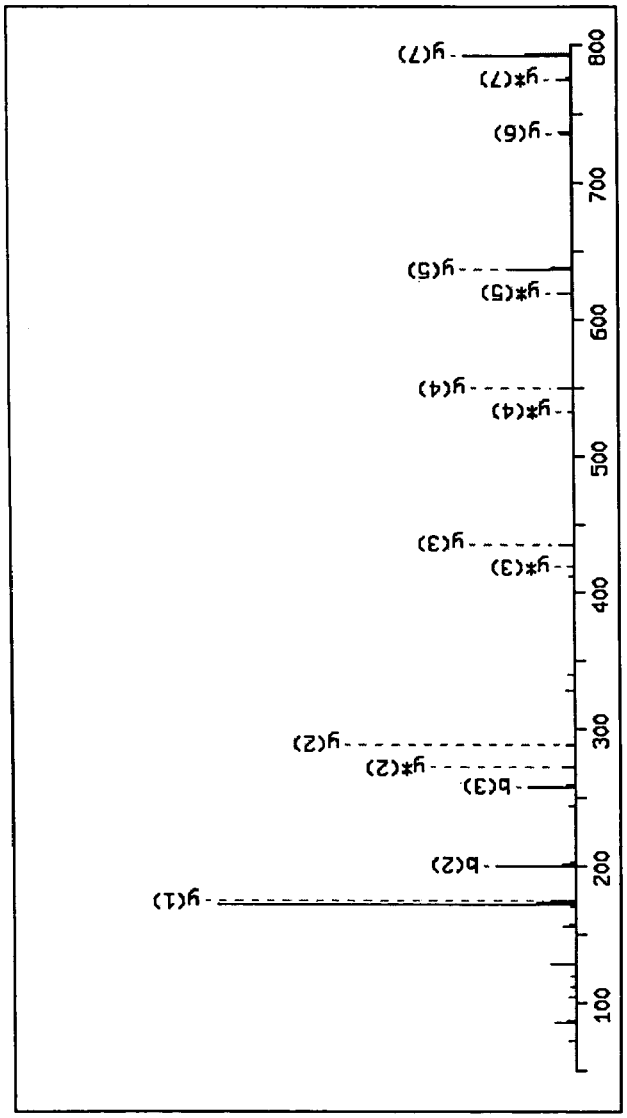
FIG. 17 shows mass spectrometric identification of protein fragments.
Figure 20:
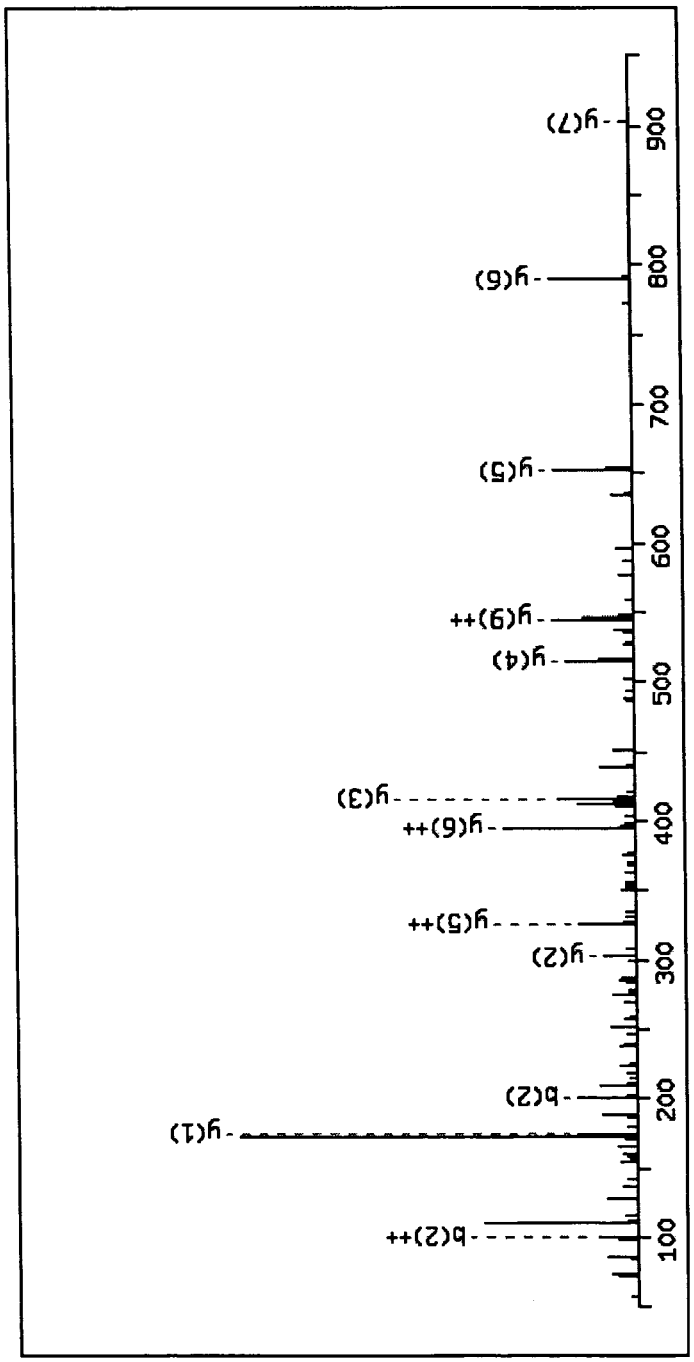
FIG. 20 shows mass spectrometric identification of protein fragments.
Figure 21:
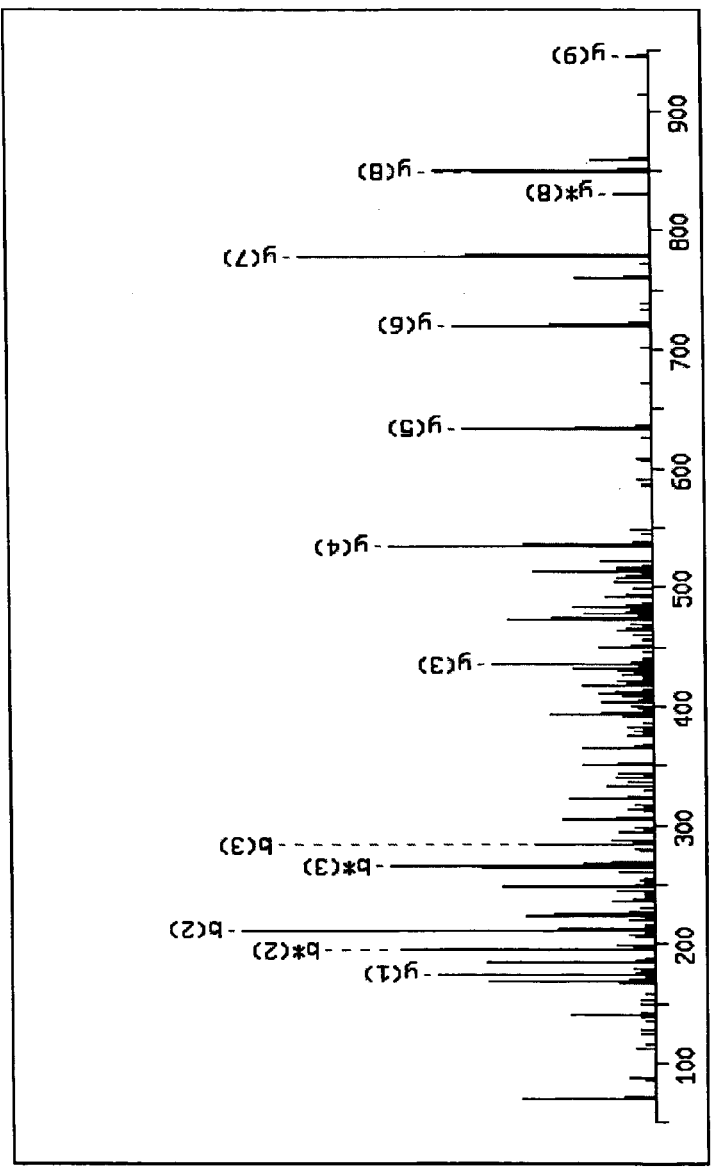
FIG. 21 shows mass spectrometric identification of protein fragments.
Figure 22:
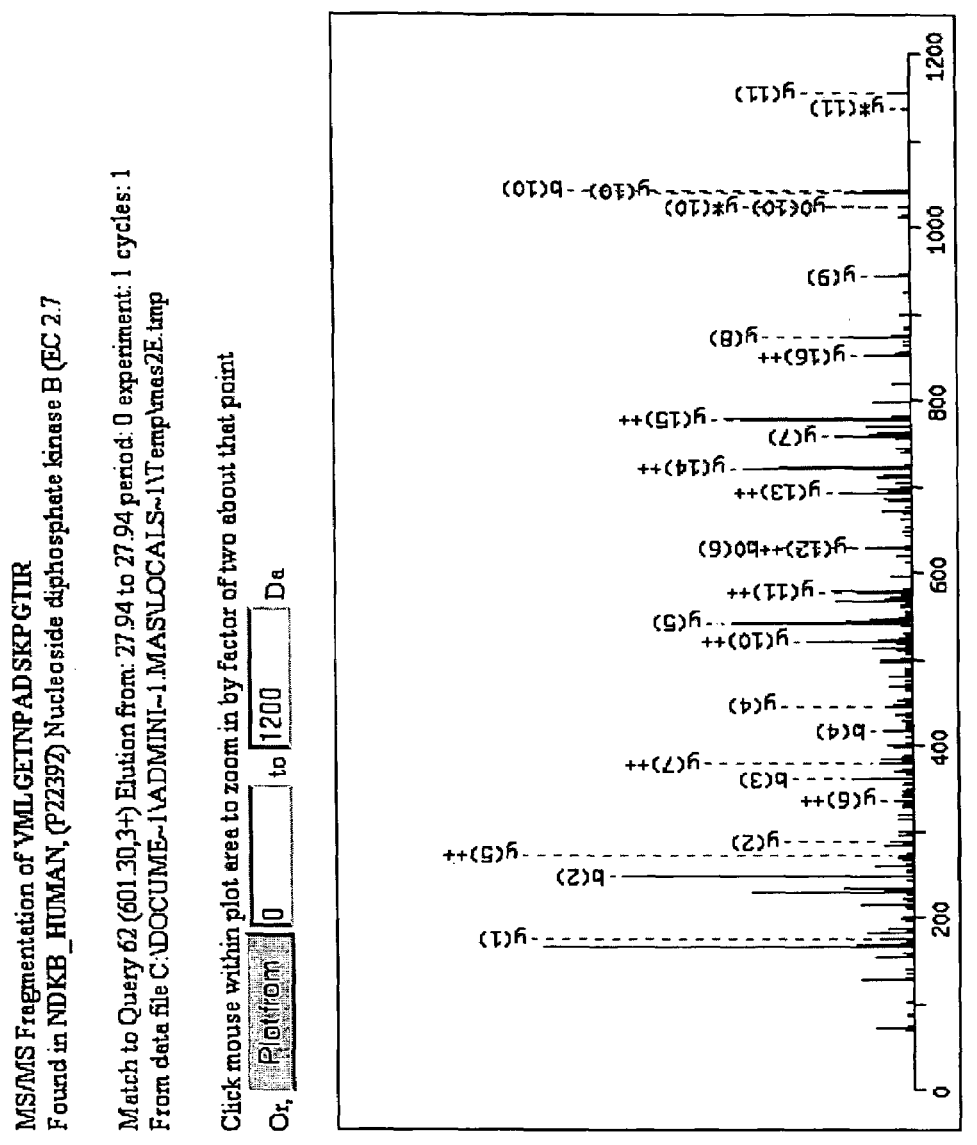
FIG. 22 shows mass spectrometric identification of protein fragments.

A derivatized form of AB129 was synthesized. The AB129 compound produced the most potent A549 cell killing response. The derivatized compound was bound to an agarose bead (P in FIG. 13) and cell lysates were passed over the beads, hoping to retain the true target of AB129 and eliminate all non-interacting proteins. Importantly, a control resin (C in FIG. 13) was used to determine if any interacting proteins were truly specific for AB129, or were common binders of the pyrazolopyrimidine scaffold. The results of the affinity purification (pull-down) experiment are shown in FIG. 14. This type of approach is successful in cases when the target affinity is high (<1 μM) and when the site of attachment to the bead does not perturb the binding to the cellular target (Mayer, T. U., et al., *Science*, 286: 9714, 1999; Kwok, B. H., et al., *Chem Biol*, 8: 759-66, 2001). Typically, hits from forward chemical genetic screens are of poor potency (>20 μM), and thus the affinity capture strategy is unsuccessful.

Using mass spectrometry the proteins retained on the AB129 beads were analyzed and three proteins identified, including carbonyl reductase 1 (CBR1) (FIGS. 15-22). To confirm that CBR1 is inhibited by AB129 CBR1 was expressed in bacteria. It was shown that AB129 is a pure NADPH competitive inhibitor of CBR1, with a Ki of 400 nM (FIG. 23). This is a very potent compound for an initial hit in a broad based screen. Importantly, the known kinase inhibitor, PP1, (FIG. 5) does not inhibit CBR1, in this in vitro assay, nor does CBR1 bind to control PP1-agarose beads, used as a control for affinity purification of the targets of AB129 (FIG. 14).

Figure 24:
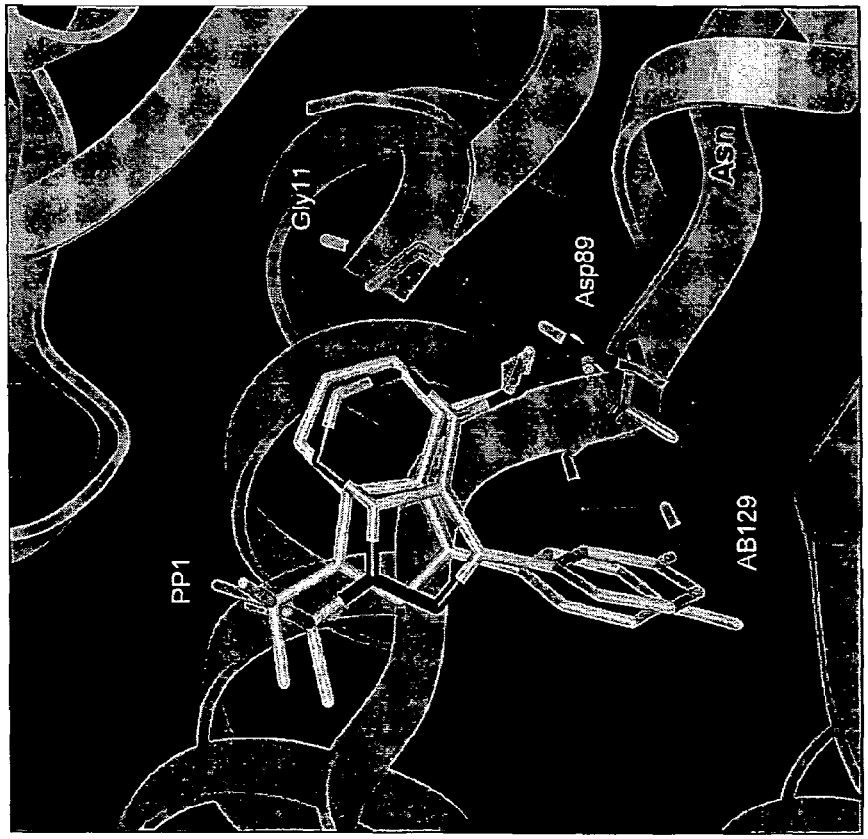
FIG. 24 shows a molecular model for docking of AB129 within porcine carbonyl reductase 1 (CBR1).
Figure 27:
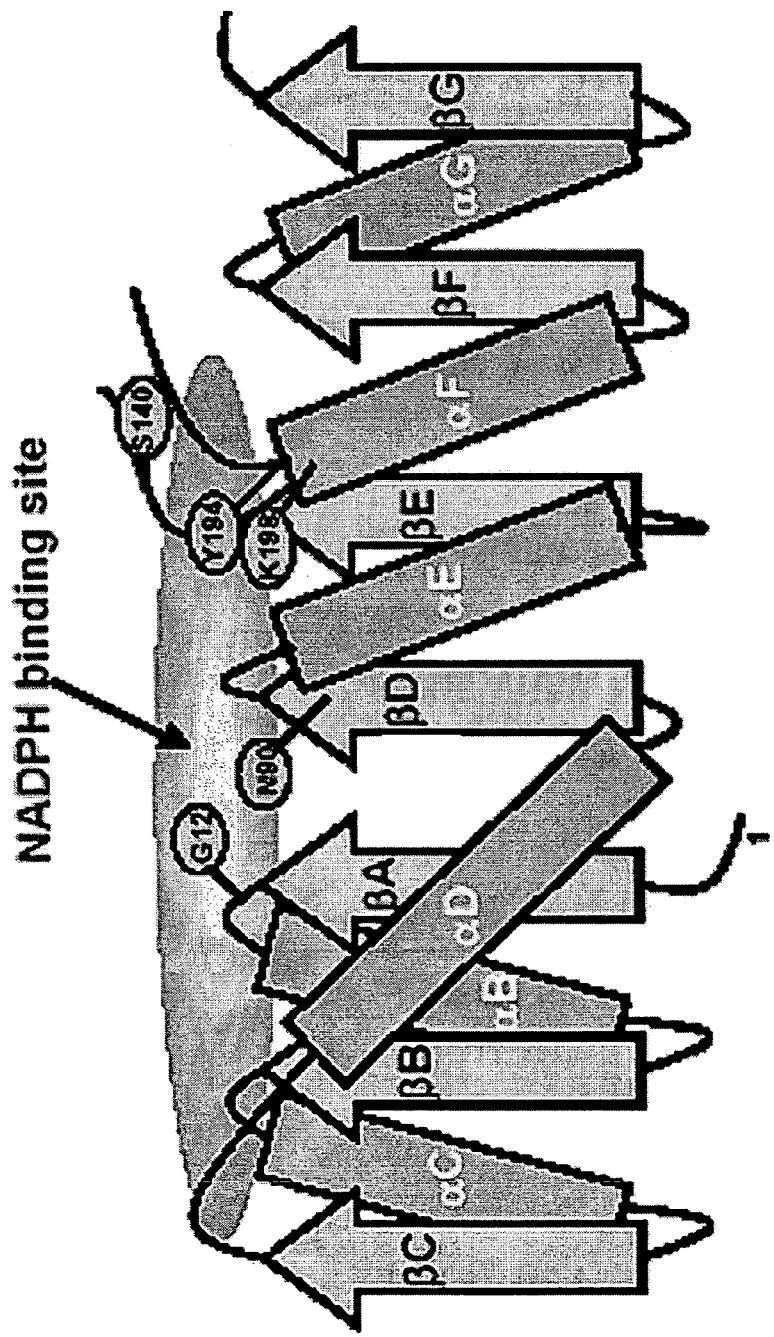
FIG. 27 shows a Rossman fold of SDR enzymes.
Figure 30:
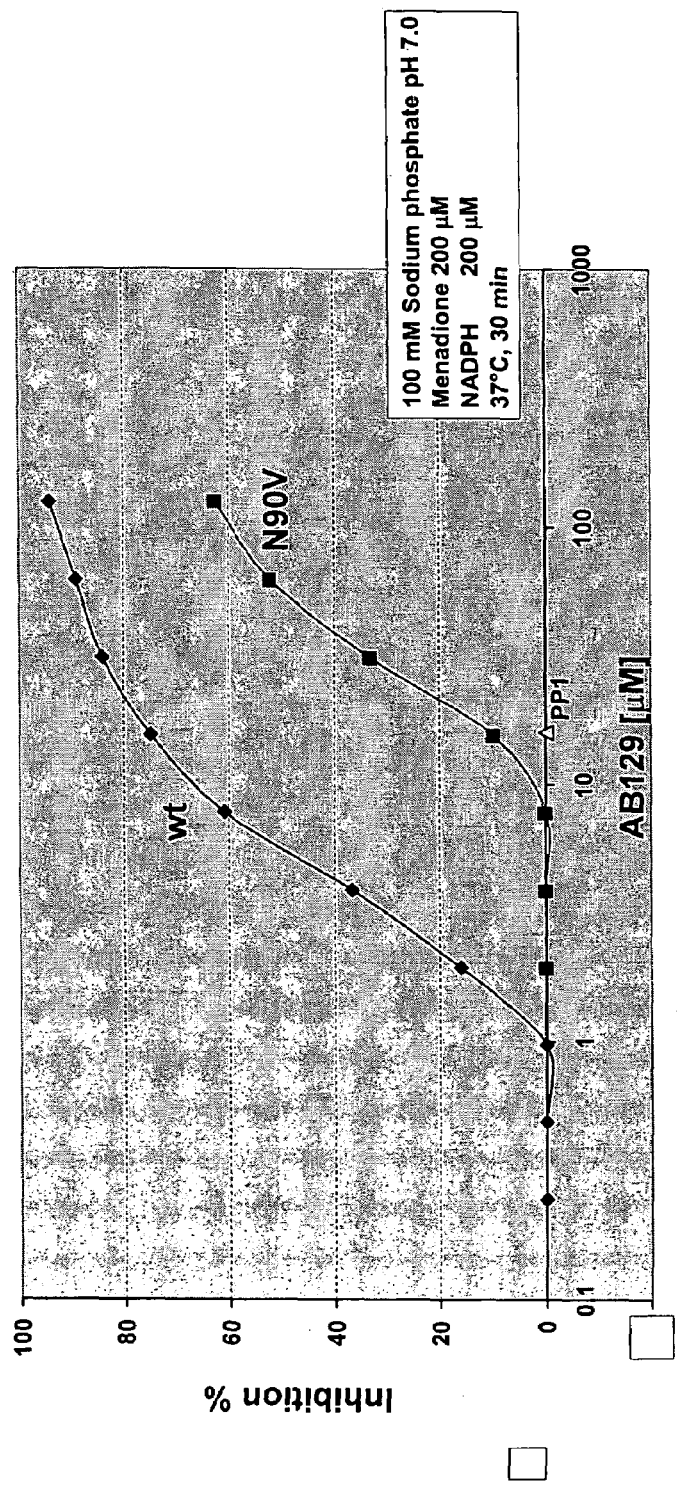
FIG. 30 shows N90V mutant of carbonyl reductase 1 (CBR1) is less sensitive to AB129 than wild type CBR1.

To understand the basis for the potency of AB129 against CBR1, a computer algorithm was used for molecular docking of AB129 to an available crystal structure of porcine CBR1 to produce a model of the bound structure of AB129 (FIG. 24). This modeled co-structure was experimentally validated by site-directed mutagenesis of multiple amino acids in the proposed AB129 binding pocket (including a conserved Asn residue common to all SDR family members—FIGS. 25-27) and identification of AB129 resistant mutants of CBR1 (FIGS. 28-30). This binding model also potentially explains the importance of the hydroxyl moiety attached to the phenyl ring of AB129, as being critical for a H-bonding interaction with an active site Asn. Since PP1 lacks this key hydroxyl group, this model potentially explains the structure activity relationship difference between PP1 and AB129 in terms of CBR1 inhibition. A conclusion from these data is that AB129 is a potent inhibitor of CBR1, a member of the SDR family of enzymes, which are responsible for a number of important small molecule metabolic steps in a variety of organs and cell types.

Figure 31:
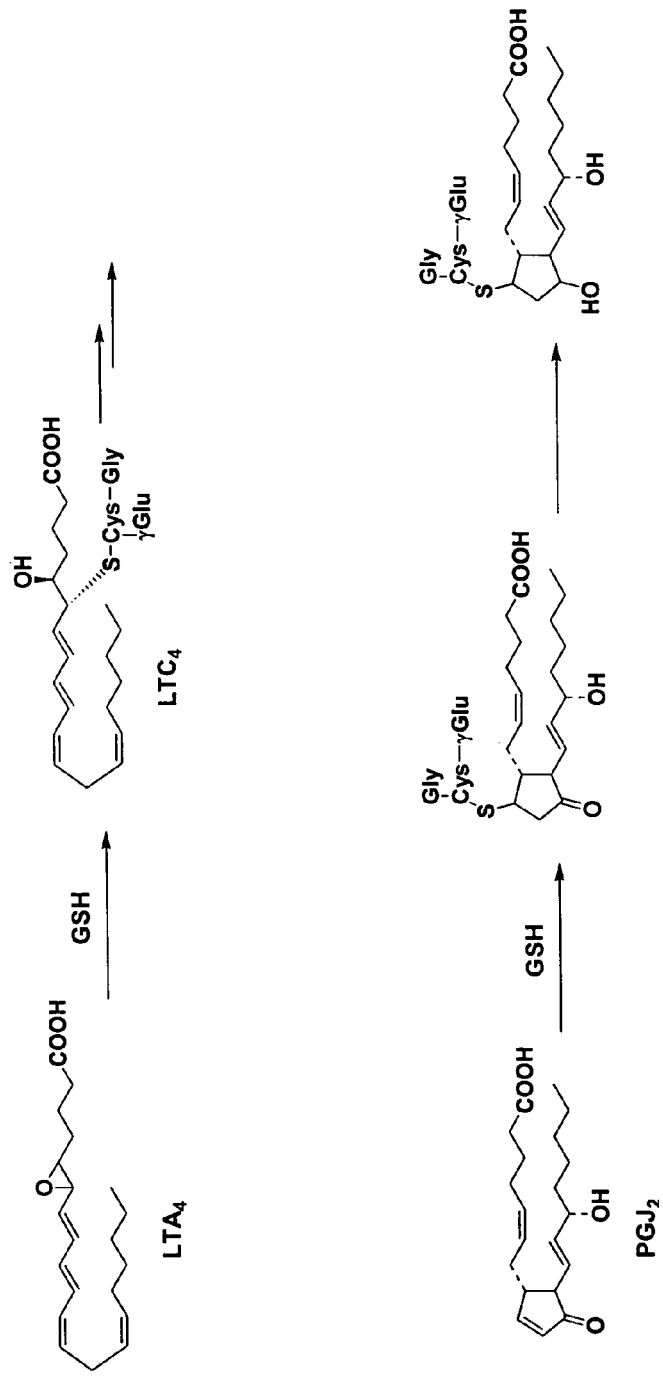
FIG. 31 shows glutathione-modified eicosanoids.
Figure 32:
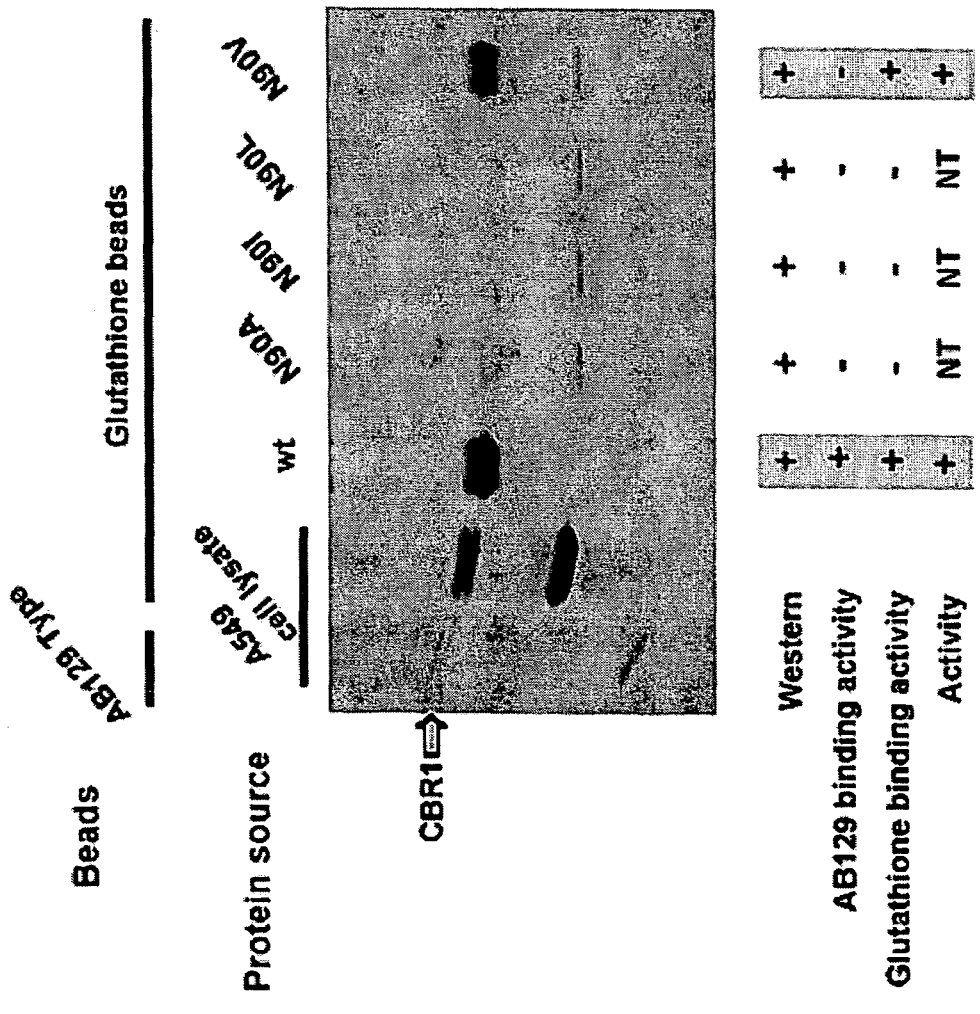
FIG. 32 shows glutathione binding activity of wild type and mutant carbonyl reductase 1 (CBR1).

GSH modified prostaglandins were recently discovered in colorectal cancer cells. (FIG. 31; *Biochim Biophys Acta* 1584: 3745, 2002) CBR1 has a glutathione binding site distinct from the AB129 binding site. Glutathione binding activity of wild type and N90V mutant CBR1 was tested. The results demonstrate that glutathione binding activity is separate from the AB129 binding activity as demonstrated for the N90V mutant CBR1. FIG. 32. These results indicate that a mechanism exists for inhibition of CBR1 and prostaglandin synthesis which can be effective in inhibition of proliferation of colorectal cancer cells.

EXAMPLE 5

Does Inhibition of CBR1 with AB129, Increase the Cell Killing Potency of Daunorubicin?

Figure 33:
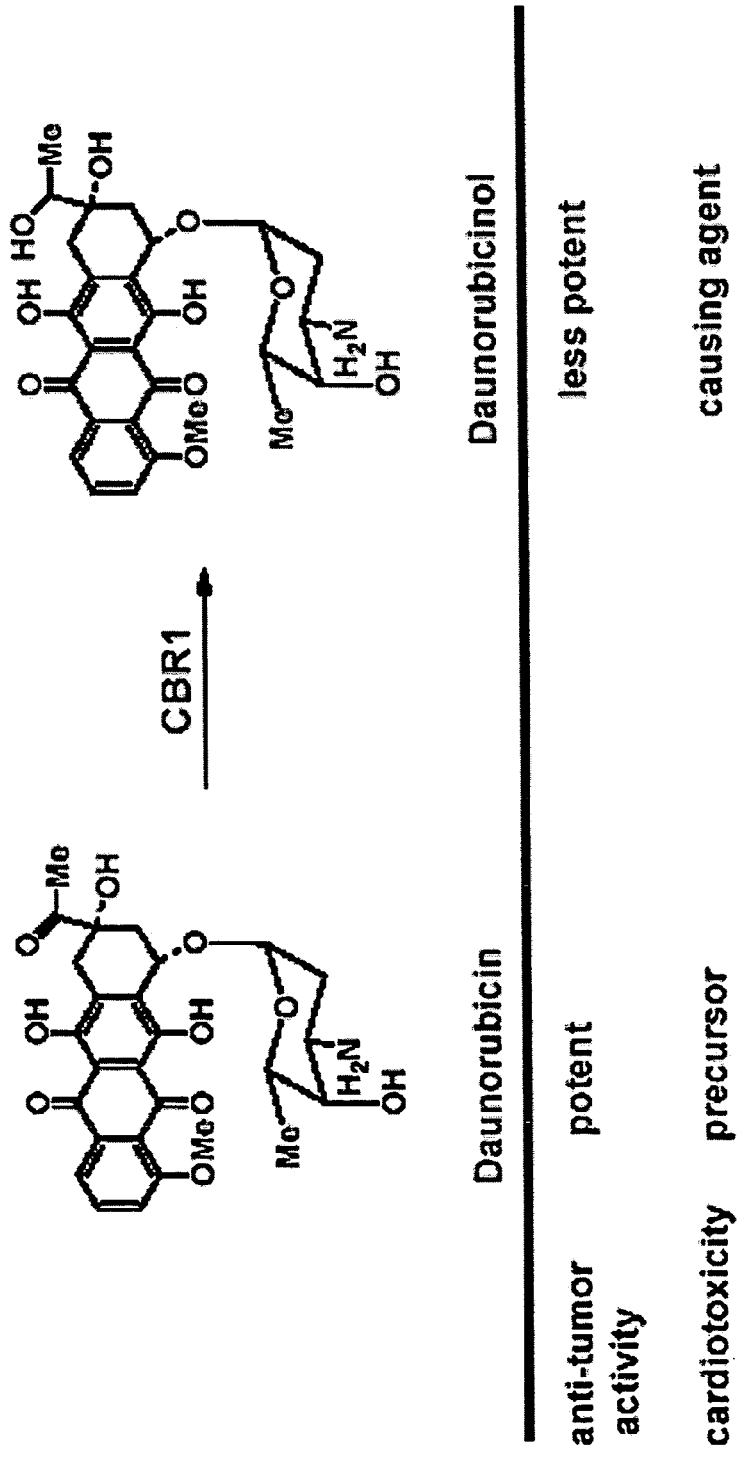
FIG. 33 shows carbonyl reductase (CBR) can cause anthracycline resistance.
Figure 34:
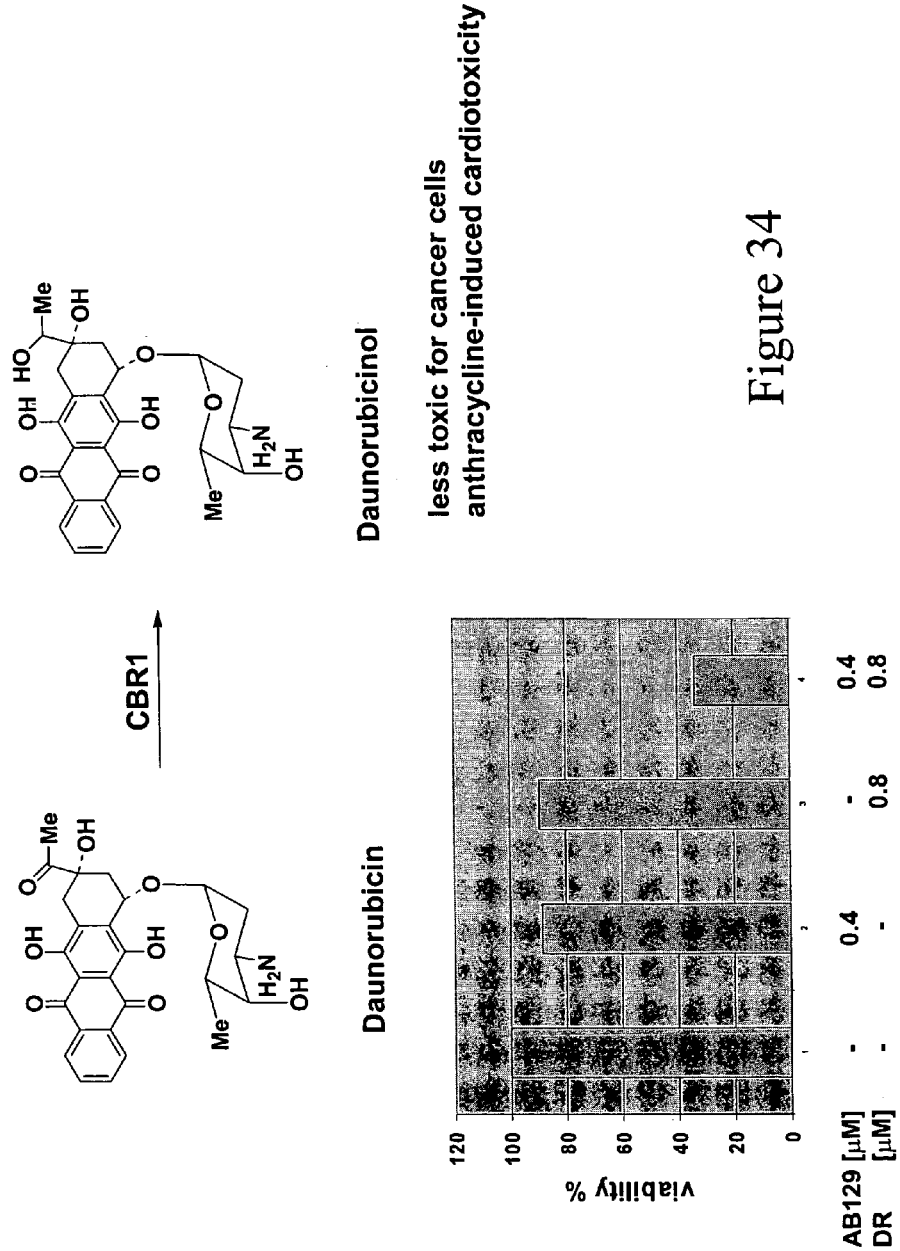
FIG. 34 shows that AB129 reinforces the cytotoxicity of daunorubicin.

One important cellular function of CBR1 is to metabolize xenobiotics such as the anticancer agent daunorubicin, a member of the anthracyclin antibiotic agents including adriamycin. Experiments were performed to test whether daunorubicin and AB129 treated cells were capable of exhibiting cell toxicity at concentrations lower than that needed for each individual compound to induce cell death alone. In agreement with this therapeutic strategy, A549 cells were treated with 0.4 μM of AB129 which led to a 15% loss of viability after two days of treatment (FIGS. 33-34). Similarly, daunorubicin, as a single agent, when added to A549 cells at 0.8 μM let to a similar 15% loss of viability of A549 cells. However, when the two drugs, AB129 and daunorubicin were added in combination at 0.4 μM and 0.8 μM, respectively, a decrease in almost 70% of A549 cell viability was observed (FIGS. 33-34). This experiment suggests that AB129 is capable of enhancing the potency of daunorubicin mediated cancer cell killing. Moreover, since AB129 does this through inhibition of CBR1, the toxic metabolite of daunorubicin, daunorubicinol is not produced and thus in vivo the cardiotoxic effects of daunorubicinol, or other anthracyclin anti-cancer therapy should be enhanced.

EXAMPLE 6

Other Targets of AB129, Including Potential Protein Kinases.

AB129 is an analog of PP1, the Src family protein kinase inhibitor. Experiments were performed to determine whether AB129 was capable of inhibiting the Src family kinase, Fyn. In fact AB129 is a potent (10 nM $IC_{50}$) inhibitor of Fyn. While the ability of AB129 to inhibit protein kinases as well as CBR1 could be important for its biological activity in some settings, AB129 compound was modified to produce a pure CBR1 inhibitor. Such a compound would serve as a test compound for determining the importance of dual inhibition of CBR1 and protein kinases. The crystal structure of PP1 bound to Hck, a Src family kinase, shows that the exocyclic amine of PP1 makes a key H-bond interaction with a backbone carbonyl group of Hck in the ATP binding pocket. It was predicted that addition of a methyl group to this amine of AB129 would disrupt this H-bond interaction because it would point away from the phenyl ring, thus eliminating the H-bond donor of AB129. In fact, the resulting analog of AB129, RB6 (FIG. 35) was found to be equipotent as a CBR1 inhibitor, yet is predicted to be >100 fold less potent as an inhibitor of Fyn. Anti-Fyn $IC_{50}$ for RB6 was 70 μM. Anti-Fyn $IC_{50}$ for AB129 was 10 nM The ability to generate inhibitors for protein kinases (PP1), or CBR1 (RB6), or both targets (AB129) (FIG. 35), should help in distinguishing between the cellular effects of CBR1 and/or kinase inhibition.

EXAMPLE 7

Designing New Potent and Selective Inhibitors of SDR Family Members Including Carbonyl Reductase 1 (CBR1), and 11β-Hydroxysteroid Dehydrogenase 1 and 2 (11β-HSD1 and 2).

Figure 36:
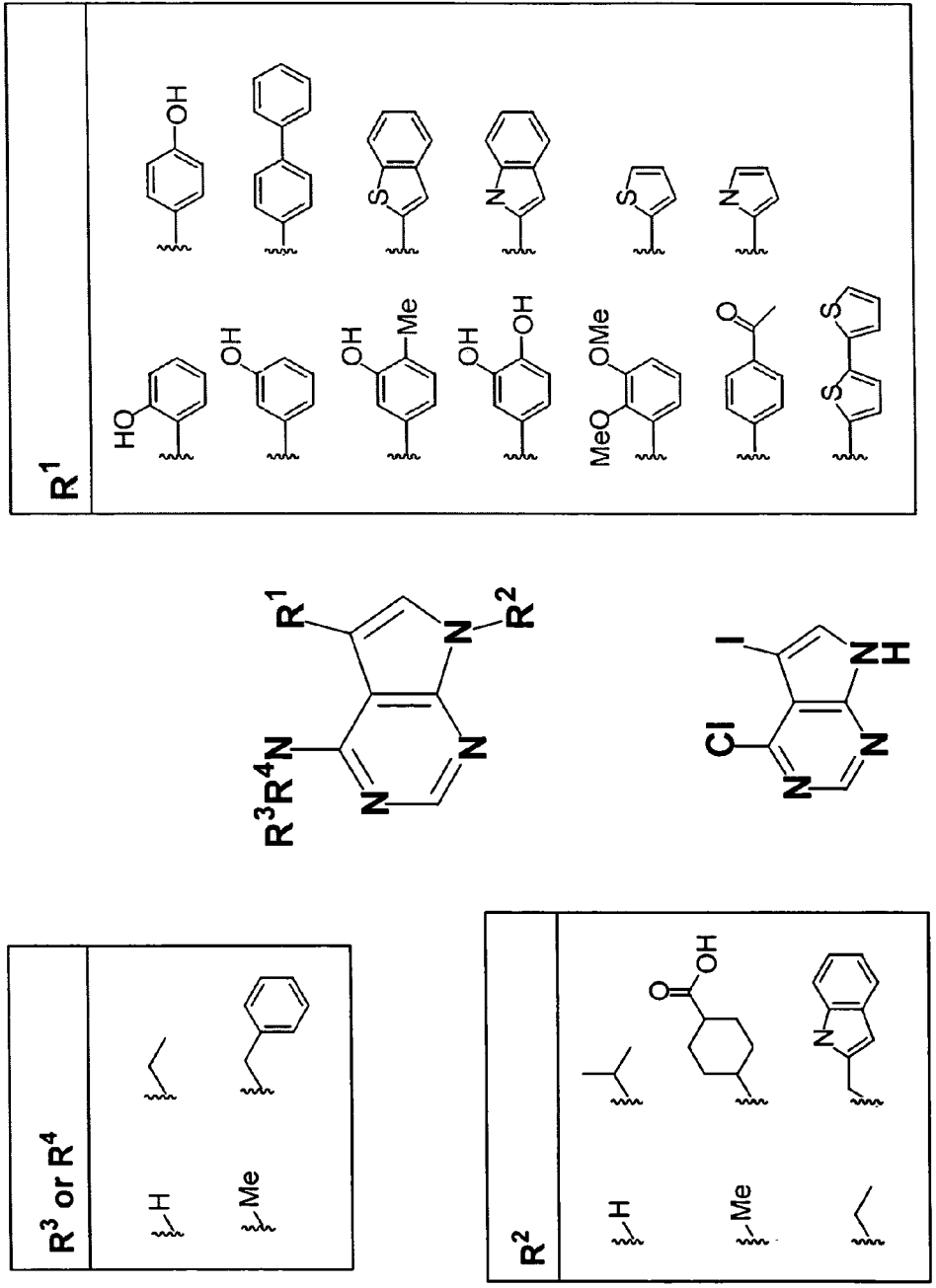
FIG. 36 shows potential library substituents for inhibitors of SDR enzymes.

Incorporating SAR data obtained from a small set of synthesized compounds, and allowing as yet untried diversity elements, a library of putative CBR inhibitors was envisioned that conserves the putative pharmacophore but introduces structural diversity elements that might increase the affinity and specificity of the library members toward various SDR enzymes. The proposed library utilizes a pyrrolopyrimidine scaffold as opposed to the pyrazolopyrimidine scaffold of AB129, and the compounds synthesized thus far indicate the anti-CBR activity of both of these scaffold types are comparable. The docked AB129-CBR structure was used to inform the choice of library substituents indicated in FIG. 36.

Diversity element $R^3$ or $R^4$ (Formula I) include either proton or alkyl substituents. Compounds with H-bond donors at this position can inhibit kinases, as does AB129, so the presence of alkyl substituents at this position should shift affinity away from kinases. AB129 and the analogs synthesized thus far possess saturated alkyl substituents at $R^2$. In addition to such substituents, the library will also include negatively charged substituents or planar aromatic groups at this position. The docking model indicates the t-butyl group (analogous to the position of $R^2$) of AB129 is solvent exposed, and in close proximity to one lysine and two arginine residues forming the binding cavity for the NADP(H) phosphate. To elicit potential ion-pairing interactions, negatively charged groups like p-cyclohexanoic acid will be included. Also adjacent to the t-butyl group of AB129 is the NADP(H) adenine binding cavity. A substituent at $R^2$ favors an orientation allowing access to this cavity. Thus, planar aromatic substituents such as indole could be accommodated resulting in increased affinity. Diversity elements at $R^1$ will include substituted phenyl, indole and thiophene moieties selected for potential H-bonding and charge interactions with specific active site residues. Substituents larger than the AB129 phenoxy may gain additional affinity by exploiting van der Walls interactions deeper within the NADPH binding channel. Although all H-bond interactions predicted between AB129 and CBR are made to conserved residues, the binding orientation and adjacent residue identity can vary throughout the SDR family. These interactions can be of particular interest for tailoring the specificity of these compounds to different enzymes of the SDR class.

Figure 37:
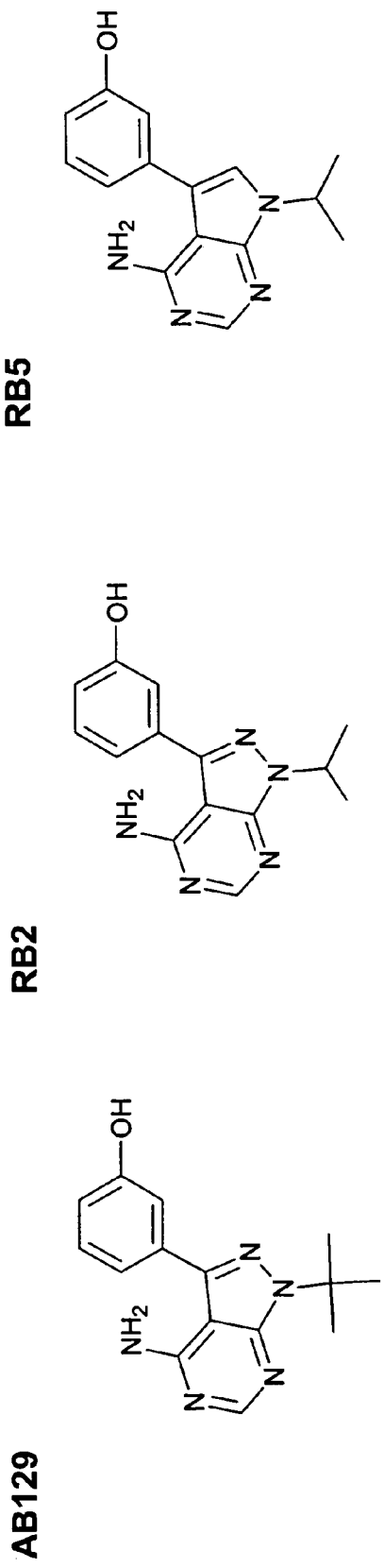
FIG. 37 shows pyrrolopyrimidine scaffold validation.

As mentioned above, it was postulated that both pyrazolopyrimidines like AB129 and analogous pyrrolopyrimidines would have comparable anti-CBR activity. In order to verify this assumption, the pyrazolopyrimidine RB2 and the analogous pyrrolopyrimidine RB5 were synthesized (FIG. 37). These compounds employ an $R^2$ isopropyl as opposed to the AB129 t-butyl because the Mitsunobu reaction used for RB5 synthesis is not amenable to t-butyl alkylation. Both of these compounds inhibit CBR with similar affinity ($IC_{50}$ values comparable to AB129) and kill adenocarcinoma cells in culture.

Figure 38:
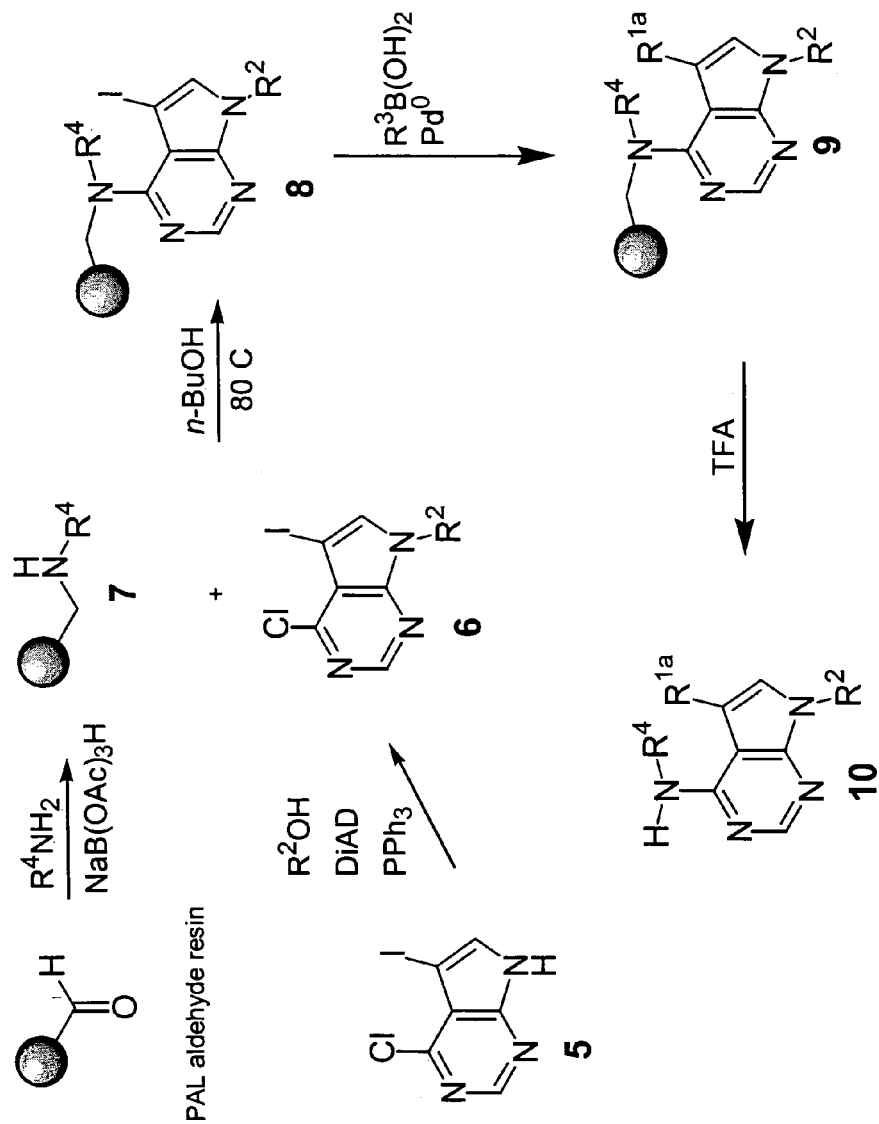
FIG. 38 shows solid phase pyrrolopyrimidine library synthesis.

The library of pyrrolopyrimidines well suited for SDR inhibition is constructed using the following solution and solid-phase reactions (FIG. 38). The pyrrolopyrimidine scaffold 4-chloro-5-iodo-7H-pyrrolo[2,3-d]pyrimidine, 5, was chosen for its synthetic utility and literature precedent. This scaffold has been synthesized previously (Pudlo, J. S., et al., *J Med Chem*, 33: 1984-92, 1990. Haslam, R., in U.K. Patent 812,366, 195 9: U.K), and was synthesized in our laboratory from ethyl cyanoacetate and bromoacetaldehyde diethyl acetal in six steps (10% yield). The library synthesis will involve introduction of $R^2$ by Mitsunobu alkylation of the scaffold, 5, using solution-phase chemistry, and a resin will be loaded with an $R^3$ $R^4$ primary amine by reductive amination. Combining these materials and heating will allow $S_NAr$ capture of the alkylated scaffold. Finally, a solid-phase Suzuki coupling to introduce $R^3$ and TFA mediated cleavage should yield the library members. Similar reaction conditions and the use of the scaffold, 5, are also amenable to solution-phase syntheses.

Primary amines containing diversity element $R^1$ will be coupled to 4-formyl-3,5-dimethoxyphenoxymethyl-functionalized (PAL) resin to yield 7 in a manner analogous to published conditions (Moon, H. S., et al., *Journal of the American Chemical Society*, 124: 11608-11609, 2002). When a primary amine at $R^3$ or $R^4$ is required, a protecting strategy can be employed. Thus, acid-labile 2,4,6-trimethoxybenzylamine should be suitable for this use. This amine mirrors the structure of the functionalized resin and should be equally acid sensitive during the cleavage reaction. Separately, in solution phase, diversity element $R^2$ will be introduced by Mitsunobu alkylation (Ding, S., et al., *J Org Chem*, 66: 8273-6, 2001) of 5 to produce 6. Although Mitsunobu alkylation has been demonstrated on solid phase (Ding, S., et al., *J Am Chem Soc*, 124: 1594-6, 2002. Ding, S., et al., *J Comb Chem*, 4: 183-6, 2002), 6 was prepared in solution. A similar coupling and reductive amination strategy using a purine scaffold has been developed for the synthesis of derivatized purines used as kinase inhibitors (Ugarkar, B. G., et al., *J Med Chem*, 43: 2894-905, 2000). In parallel, each of the resultant products 6 will be reacted with the resin bound amine 7 to yield compound 8 on solid support. Again in a manner analogous to that used for the preparation of kinase inhibitors, 8 will be treated with commercially available boronic acids using Suzuki coupling conditions to introduce the diversity element $R^1$. Similar reactions have been carried out in solution phase (Ugarkar, B. G., et al., *J Med Chem*, 43: 2894-905, 2000). The compounds can then be cleaved from the PAL resin using trifluoroacetic acid.

Figure 39:
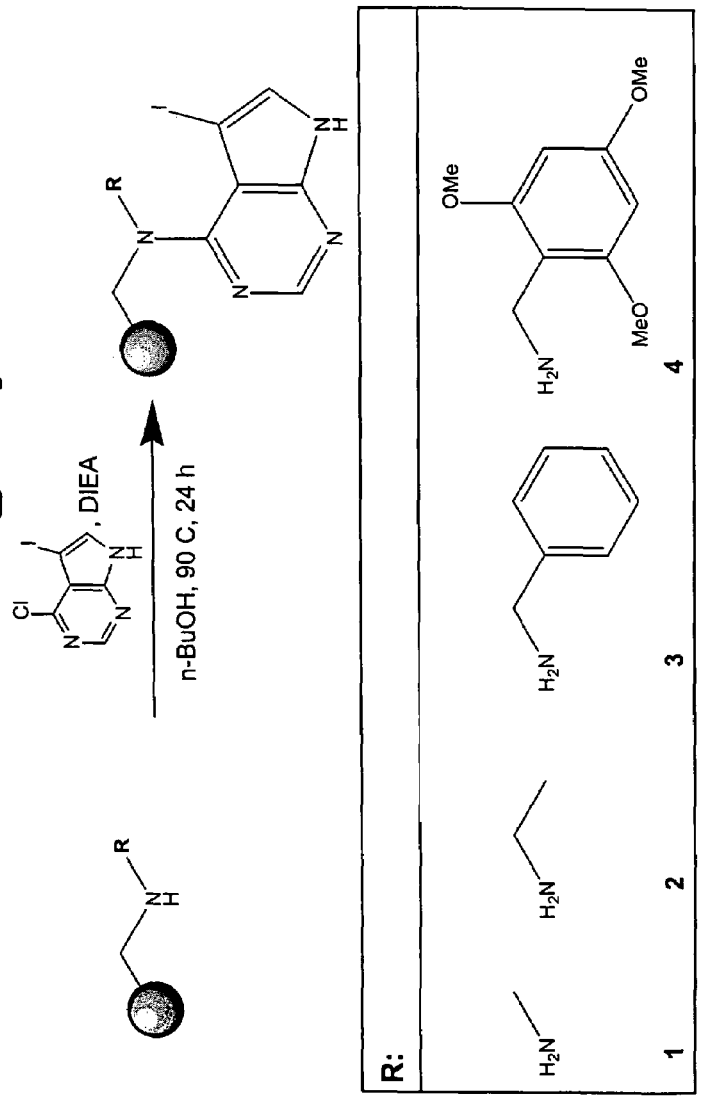
FIG. 39 shows scaffold loading optimization.

Optimizations of both reductive amination and scaffold loading (FIG. 20) have been performed using a number of conditions, and good results have been obtained. The reductive amination reactions to produce 7 have utilized methylamine, ethylamine, benzylamine and 2,4,6-trimethoxybenzylamine (FIG. 39). The reactions were carried out in peptide synthesis cartridges using the reducing agent $NaBH(OAc)_3$ in a manner analogous to that previously reported (Moon, H. S., et al., *Journal of the American Chemical Society*, 124: 11608-11609, 2002). When using 2,4,6-trimethoxybenzylamine the HCl salt was used, and a stoichiometric quantity of DIEA was also included. Comparable yields were obtained using 5 and 20 eq. (0.1 and 0.4 M respectively) of amine with either THF or 1:1 THF:DMF as evidenced by FMOC quantitation (Bunin, B., *The Combinatorial Index*, ed. San Diego: Academic Press, 1998).

Loading of the scaffold with resin bound primary amine 7 was also attempted using each of the amine-loaded resins. Either THF or n-BuOH at 60 or 90° C. respectively in the presence of 10% DIEA was employed. The values reported (FIG. 39) represent conversion at 90° C. for 18 h, as determined by FMOC quantification.

The conditions for both reductive amination and resin loading appear to work well for the conditions tested.

The pyrrolopyrimidine scaffold 5 was also used as starting material for the solution phase synthesis of RB5 and RB6 (FIG. 10) with greater than 50% overall yield. Thus, should library members demonstrate activity in vitro and larger quantities of material are needed, a solution-phase strategy can be more efficient. RB5 synthesis commenced with Mitsunobu alkylation of 5 with 2-propanol resulted in the preparation of 6 in greater than 90% yield. Mitsunobu reactions of pyrrolopyrimidines are scarce in the literature; however, the utility of the transformation has been demonstrated with purines. Therefore, an analogous procedure using DiAD, $PPh_3$ and 2-propanol was employed (Ding, S., et al., *J Org Chem*, 66: 8273-6, 2001). Compound 6 was subsequently aminolyzed at elevated temperature in a sealed vessel using a saturated methanolic ammonia solution. As expected, this reaction was selective for the 4-chloro position of 6 for both ammonia and methylamine used during the synthesis of RB5 and RB6 respectively. Treatment of the products with 3-(hydroxyphenyl)boronic acid afforded RB5 and RB6 using available Suzuki coupling conditions (Moon, H. S., et al., *Journal of the American Chemical Society*, 124: 11608-11609, 2002). These conditions do not require the protection of hydroxylic or amino substituents of the boronic acids.

In vitro assays for the measurement of CBR activity have been developed (Bohren, K. M., et al., *J Mol Biol*, 244: 659-64, 1994) and used in our laboratories. CBR was expressed in *E. coli* and purified using glutathione beads; CBR has a naturally occurring. glutathione binding site. An N-terminal 6-His tagged protein was prepared to allow purification by metal affinity. Our CBR assay employs the synthetic substrate Menadione (2-methyl-1,4-naphthoquinone). Reaction progress is monitored by the decrease in NADPH-absorbance at 340 nm. Saturating concentrations of Menadione with variable concentrations of NADPH are employed in order to ascertain $K_I$ values.

A high-throughput assay will be optimized for analyzing library compounds. A 96-well format will be employed, and the disappearance of NADPH will be monitored either by fluorescence or absorbance. Using fixed substrate and enzyme concentrations, $IC_{50}$ values for library members can be obtained. Cell culture assays for CBR inhibition can also be developed, as CBR inhibitors in the presence of daunorubicin would be expected to lead to a further decrease in cell proliferation rate than either compound alone.

In addition to the use of CBR activity for screening library compounds, recombinant 11β-HSD1 is prepared (Nobel, C. S., et al., *Protein Expr Purif*, 26: 349-56, 2002). This enzyme is a membrane-bound glycoprotein, and previous reports indicate that the isolation of active enzyme is not trivial. An expression system using *Pichia pastoris* has been described. A yeast expression vector for 11β-HSD1 incorporating an N-terminal 6-His tag and a picornavirus protease cleavage site. Following characterization of the enzyme activity, an assay similar to that used for detecting CBR activity is developed. An expression system for 17β-HSD1 is developed to allow the specificity of these compounds to be further investigated.

The inhibitor screening results should provide valuable SAR data for the pyrrolopyrimidine pharmacophore, and provide valuable information for producing even more effective inhibitors in the future. Continuing studies to assess the selectivity of these analogs among different SDR enzymes and associated cellular phenotypes will be pursued. Differential activity of the library members toward CBR and other SDR members when coupled with available crystallographic and sequence data, should help to identify important structural and electronic features that lead to effective and specific inhibition of SDR enzymes.

Chemical genetic screens for small molecules which target disease related biological processes hold great promise for development of future medicines. A well designed chemical genetic screen like a well designed genetic screen requires manipulation of the pathway of interest such that early-low potency "hits" can be identified. This precludes the simultaneous screening of more than one pathway in each assay. Since a limited portion of chemical space is probed in any library of small molecules, there is a limited chance that a potent and selective agent targeting a pathway of interest will be present. Consequently the frequency of identifying true drug-leads in such screens has been relatively low. Chemical-genetic screens have an additional challenge, compared with genetic screens, that of target identification: Identification of the target of a small molecule lead compound is difficult because the affinity of such early hits are often low, and thus not amenable to successful affinity purification strategies which require tight, or irreversible inhibitors (usually only found in natural products or advanced drug development candidates). To overcome these problems, the traditional format of chemical genetic screens was inverted. Rather than screening a very large collection of small molecules for antagonists or agonists of a single pathway, a small panel of compounds was screened for the ability to perturb any pathway in a panel of cell lines with high potency and selectivity. A strategy was exploited utilizing a cell morphology-microscopy based assay coupled with an automated image analysis algorithm designed to detect perturbations to a great many cell processes simultaneously including, for example, cell cycle arrest point, cytoskeletal structure, cell adhesion status, organelle organization. This approach allowed phenotypic effects of all members of the library to be scored, and showed that almost every compound in the library at the highest doses analyzed (10 µM), produced some phenotypic effects. AB129 was selected, which potently produced a novel phenotype, (several controls were included such as, Taxol and K252a, to define known phenotype signatures), in a single cell line-the lung cancer A549 line, but not other cell lines. Using traditional target identification methods applied to natural products, but rarely applied to first generation hits from chemical genetic screens the target of AB129 in A549 lysates was identified as an NADPH dependent reductase, carbonyl reductase 1 (CBR1). CBR1 serves a dual role of prostaglandin biosynthesis and xenobiotic metabolism. In vitro assays demonstrated AB129 is an NADPH competitive inhibitor of CBR1 with a Ki of approximately 300 to 400 nM, validating the overall approach to be successful at identification of potent lead compounds. The relevance of CBR1 to lung cancer was explored through analysis of transcriptional profiling data of various lung cancer cell lines. This analysis revealed CBR1 to be a highly upregulated transcript in adenocarcinomas suggesting it might play an important role in producing prostaglandins as autocrine factors for A549 cell survival. siRNA studies confirm that CBR1 is essential for A549 cell viability, confirming the mode of action of AB129 at inducing A549 cell death. To independently confirm the ability of AB129 to inhibit CBR1 in A549 cells, an assay based on the role of CBR1 in attenuating the anti-cancer action of daunorubicin was employed. Indeed, AB129 is able to potentiate daunorubicin action in A549 cells, suggesting the former can be an attractive combination therapy with daunorubicin. Moreover, AB129 is able to block production of the cardiotoxic metabolite daunorubicinol from daunorubicin. Thus, a new broad based phenotype profiling method allowed for system wide screening of chemical libraries allowed for the discovery of a potent small molecule capable of selective killing of lung cancer A549 cells and potentiating the action of daunorubicin.

EXAMPLE 8

New Potent and Selective Inhibitors of SDR Family Members Including Carbonyl Reductase 1 (CBR1), and 11β-Hydroxysteroid Dehydrogenase 1 and 2 (11β-HSD1 and 2).

RB8:

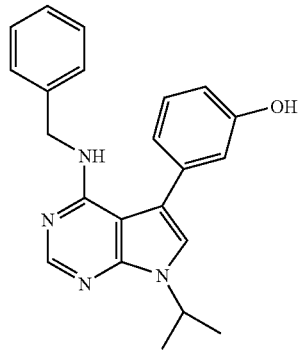

Compound RB8 employs a substituent, benzyl, at the exocyclic amine on the pyrrolopyrinidine/pyrazolopyrimidine scaffold. The anti-CBR $IC_{50}$=4.4 µM, and the anti-Fyn $IC_{50}$=20 µM.

RB11:

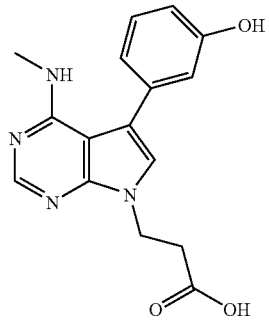

Compound RB11 employs a carboxy alkyl substituent at N-9 of the pyrrolopyrinidine/pyrazolopyrimidine scaffold. Compound RB11 demonstrates an improved anti-CBR $IC_{50}$ activity. An increased affinity can be attributed to potential hydrogen bond interactions between the carboxylate and charged residues including Asn 13, Arg 41, and Arg 37 of CBR. These residues would otherwise interact with the NADPH 3'-$OPO_3^{2-}$ phosphate upon substrate binding, and can provide specificity for short chain dehydrogenase/reductase (SDR) utilizing NADP(H) rather than NAD(H). The anti-CBR IC$_{50}$ for compound RB11 is 220 nM.

RB10:

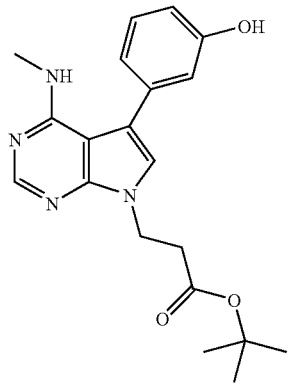

RB10 is an intermediate in the synthesis of RB11. The anti-CBR IC$_{50}$=1.15 µM. An improved IC$_{50}$ for compound RB10 may be due to its inability to hydrogen bond to residues including Asn 13, Arg 41, and Arg 37 of CBR1.

Substituents at N-9 of the pyrrolopyrimidine/pyrazolopyrimidine scaffold can further include alkyl chains substituted with carboxyl and/or phosphoryl, e.g., R$_2$ substituents of compounds of Formulas I, II, or III.

In addition to the above compounds, the effect of substituents at the meta position of the phenyl ring have been studied (see below, Compound A, as an example of a compound derived from Formula I). Potency as anti-CBR activity can be increased with electron withdrawing groups (Br, CF$_3$) at the 5-position of the pyrrolopyrinidine/pyrazolopyrimidine scaffold. The CBR binding can be tolerant of even large substituents (tert-butyl) at this position.

Substituting a halo substituent, for example, chloro or bromo, in place of the exocyclic amine (see below, Compound B. as an example of a compound derived from Formula III) provides an increased affinity for CBR binding. Compounds of the present invention can employ an exocyclic amine or a halo substituent as part of the pyrrolopyrinidine/pyrazolopyrimidine scaffold. Substituting a chloro substituent for a methylamino substituent on the pyrrolopyrinidine/pyrazolopyrimidine ring gives a roughly 10-fold increase in potency. For substituents of chloro or bromo, the IC$_{50}$ is approximately 30 nM.

Compound A:

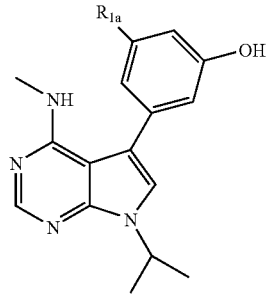

Compound B:

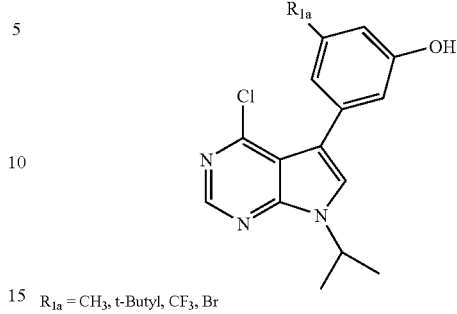

R$_{1a}$ = CH$_3$, t-Butyl, CF$_3$, Br

EXAMPLE 8

New Potent and Selective Inhibitors of SDR Family Members Including Carbonyl Reductase 1 (CBR1), and Src Family Protein Kinase, Fyn.

A chloro substituent in place of the exocyclic amine on the pyrrolopyrimidine/pyrazolopyrimidine scaffold provides increased affinity. See SD1 and SD5 below. The switch from methylamino to chloro substituents on the pyrimidine ring gives a roughly 10-fold increase in potency in all cases. For SD1 compound, having methylamino and bromo substituents, the anti-CBR IC$_{50}$ is 220 nM. For SD5 compound, having chloro and bromo substituents, the anti-CBR IC$_{50}$ is 27 nM.

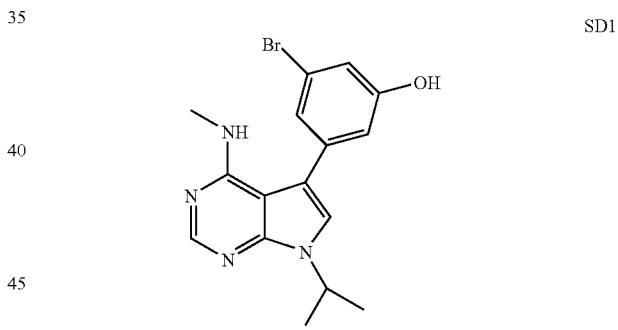

SD1

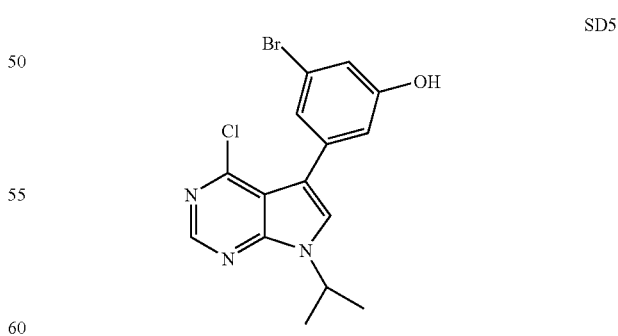

SD5

Because replacement of the exocyclic amine with a more hydrophobic, electron-withdrawing substituent (Cl) increases potency, these results suggest that exocyclic methylamino can be substituted with halogens (F, Cl, Br, I), hydrogen, small electron-withdrawing groups (NO$_2$, CN, etc.), or small alkyl and haloalkyl groups at this position.

In addition the effect of substituents at the meta position of the phenyl ring increases potency as a CBR1 inhibitor (see below). Potency as a CBR1 inhibitor increases with electron withdrawing groups (Br, $CF_3$) at the 5-position and the CBR seems tolerant of even large substituents (t-butyl) at this position. substituents at the meta position include electron withdrawing groups, for example, ester and amide linkages (—COOR, —CONHR).

SD2

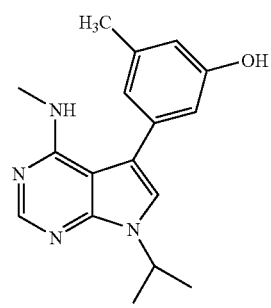

SD6

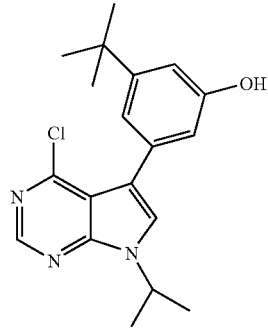

The anti-CBR $IC_{50}$ for SD2 is 3.04 μM. The anti-CBR $IC_{50}$ for SD6 is 193 nM

SD3

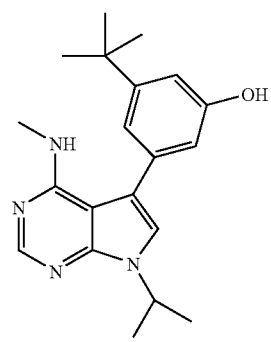

SD7

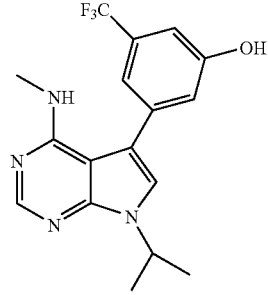

The anti-CBR $IC_{50}$ for SD3 is 7.65 μM. The anti-CBR $IC_{50}$ for SD7 is 376 nM.

SD4

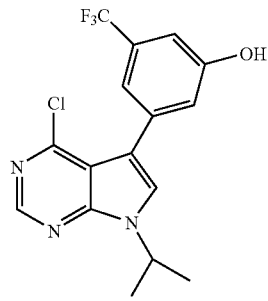

SD8

The anti-CBR $IC_{50}$ for SD4 is 416 nM. The anti-CBR $IC_{50}$ for SD8 is 67 nM.

EXAMPLE 9

New Potent and Selective Inhibitors of SDR Family Members Including Carbonyl Reductase 1 (CBR1), and Src Family Protein Kinase, Fyn.

Table 1 shows compounds of the present invention that are inhibitors of the Src family knase, Fyn, and are inhibitors of carbonyl reductase 1 (CBR1). AB129 is a potent (10 nM $IC_{50}$) inhibitor of Fyn. While the ability of AB129 to inhibit protein kinases as well as CBR1 could be important for its biological activity in some settings. AB129 compound was further modified to produce compounds of the present invention which are CBR1 inhibitors with reduced inhibitory activity for Fyn.

TABLE 1

IC$_{50}$ for anti cFYN and anti-hCBR1

| Compound | Structure | IC$_{50}$ anti-c-Fyn-wt | IC$_{50}$ anti-hCBR1 |
|---|---|---|---|
| AB001 | 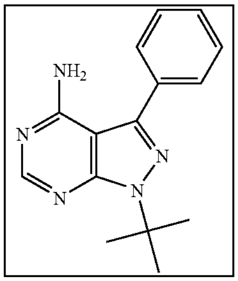 | 110 nM | >20 µM |
| AB060 | 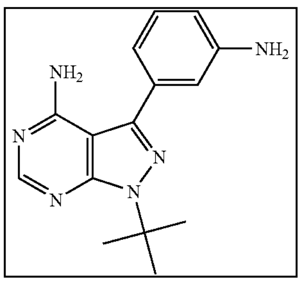 | 50 nM | >20 µM |
| AB061 | 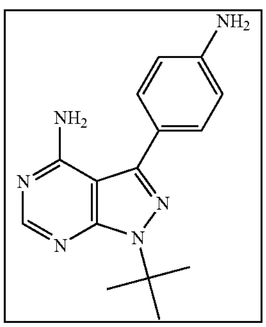 | 50 nM | >20 µM |
| AB129 | 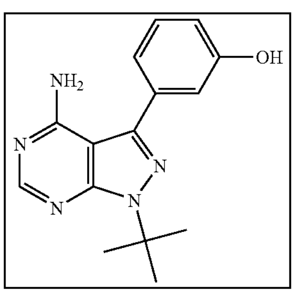 | 8 nM | 790 nM |
| PP1 | 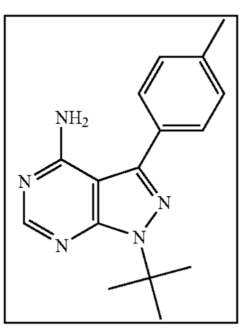 | 50 nM | >20 µM |

TABLE 1-continued

IC$_{50}$ for anti cFYN and anti-hCBR1

| Compound | Structure | IC$_{50}$ anti-c-Fyn-wt | IC$_{50}$ anti-hCBR1 |
| --- | --- | --- | --- |
| MT13 | 4-amino-3-phenyl-1-(2-ethoxyethyl)-1H-pyrazolo[3,4-d]pyrimidine | 5 µM | >20 µM |
| MT15 | 4-amino-3-(3-hydroxyphenyl)-1-(2-ethoxyethyl)-1H-pyrazolo[3,4-d]pyrimidine | 0.2 µM | 930 nM |
| MS01 | 4-amino-3-(4-fluoro-3-hydroxyphenyl)-1-tert-butyl-1H-pyrazolo[3,4-d]pyrimidine | 3 nM | 1 µM |
| RB01 | 4-amino-3-(3-hydroxybenzyl)-1-tert-butyl-1H-pyrazolo[3,4-d]pyrimidine | 1.2 µM | >20 µM |

TABLE 1-continued
IC$_{50}$ for anti cFYN and anti-hCBR1
| Compound | Structure | IC$_{50}$ anti-c-Fyn-wt | IC$_{50}$ anti-hCBR1 |
|---|---|---|---|
| RB02 | 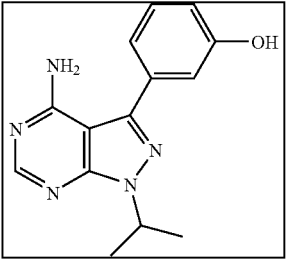 | 11 nM | 1 μM |
| RB03 | 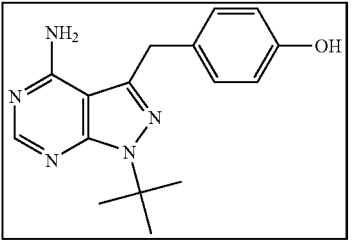 | ~20 μM | >20 μM |
| RB04 | 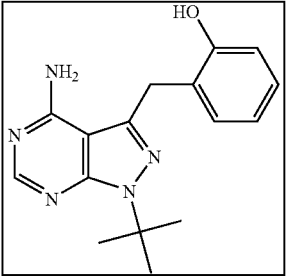 | 120 nM | >20 μM |
| RB05 | 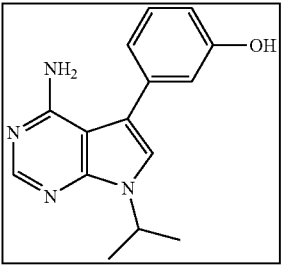 | 12 nM | 760 nM |
| RB06 | 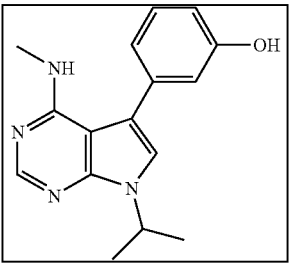 | 70 μM | 590 nM |

TABLE 1-continued

IC$_{50}$ for anti cFYN and anti-hCBR1

| Compound | Structure | IC$_{50}$ anti-c-Fyn-wt | IC$_{50}$ anti-hCBR1 |
|---|---|---|---|
| RB07 | 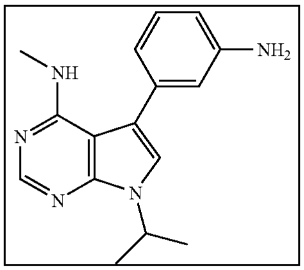 | not determined (n/d) | >20 μM |
| RB08 | 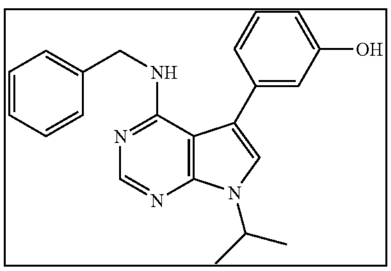 | 20 μM | 4.4 μM |
| RB09 | 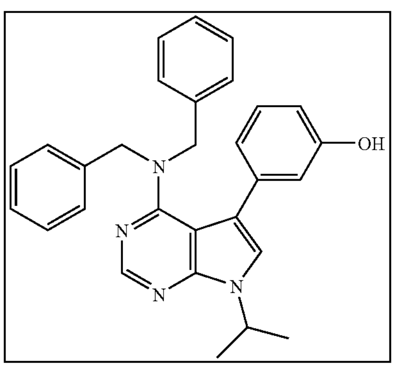 | n/d | >20 μM |
| RB10 | 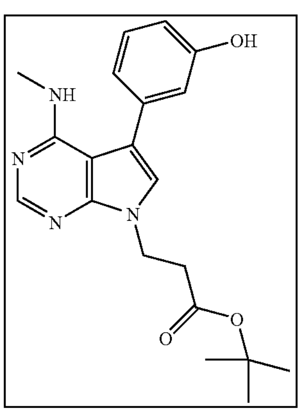 | n/d | 1.15 μM |

TABLE 1-continued

IC$_{50}$ for anti cFYN and anti-hCBR1

| Compound | Structure | IC$_{50}$ anti-c-Fyn-wt | IC$_{50}$ anti-hCBR1 |
|---|---|---|---|
| RB11 | 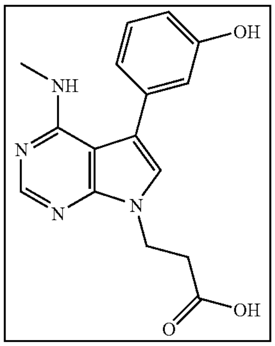 | n/d | 220 nM |
| SD1 | 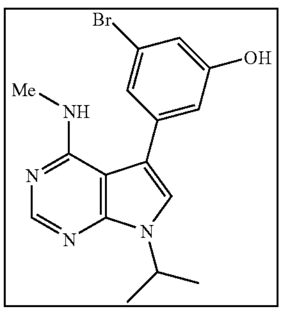 | n/d | 220 nM |
| SD2 | 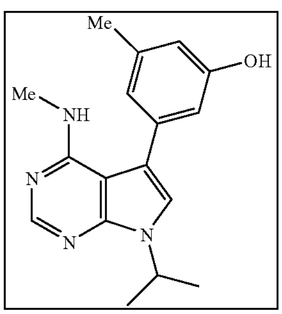 | n/d | 3.04 µM |
| SD3 | 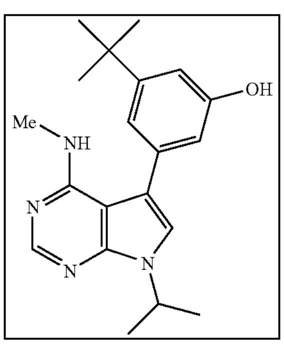 | n/d | 7.65 µM |

TABLE 1-continued

IC$_{50}$ for anti cFYN and anti-hCBR1

| Compound | Structure | IC$_{50}$ anti-c-Fyn-wt | IC$_{50}$ anti-hCBR1 |
|---|---|---|---|
| SD4 | *(structure: 4-(methylamino)-5-(3-hydroxy-5-trifluoromethylphenyl)-7-isopropyl-7H-pyrrolo[2,3-d]pyrimidine)* | n/d | 416 nM |
| SD5 | *(structure: 4-chloro-5-(3-bromo-5-hydroxyphenyl)-7-isopropyl-7H-pyrrolo[2,3-d]pyrimidine)* | n/d | 28 nM |
| SD6 | *(structure: 4-chloro-5-(3-methyl-5-hydroxyphenyl)-7-isopropyl-7H-pyrrolo[2,3-d]pyrimidine)* | n/d | 193 nM |
| SD7 | *(structure: 4-chloro-5-(3-tert-butyl-5-hydroxyphenyl)-7-isopropyl-7H-pyrrolo[2,3-d]pyrimidine)* | n/d | 376 nM |

TABLE 1-continued

IC$_{50}$ for anti cFYN and anti-hCBR1

| Compound | Structure | IC$_{50}$ anti-c-Fyn-wt | IC$_{50}$ anti-hCBR1 |
|---|---|---|---|
| SD8 | 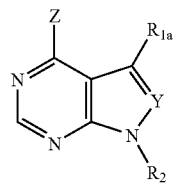 | n/d | 67 nM |

When ranges are used herein for physical properties, such as molecular weight, or chemical properties, such as chemical formulae, all combinations and subcombinations of ranges and specific embodiments therein are intended to be included.

The disclosures of each patent, patent application and publication cited or described in this document are hereby incorporated herein by reference, in their entirety.

Those skilled in the art will appreciate that numerous changes and modifications can be made to the embodiments of the invention and that such changes and modifications can be made without departing from the spirit of the invention. It is, therefore, intended that the appended claims cover all such equivalent variations as fall within the true spirit and scope of the invention.

What is claimed is :

1. A compound of Formula I:

I or a pharmaceutically-acceptable salt thereof;
wherein:
Y is CR$_5$;
Z is NR$_3$R$_4$, halo, H, OH, alkyl, alkyloxy, or haloalkyl;
R$_{1a}$ is phenyl substituted with —OH, wherein said phenyl is additionally substituted with at least one of —OH, —CN, NO$_2$, C(=O)OH, —C(=O)O-alkyl, (C$_1$-C$_4$) alkyl, halo, haloalkyl or haloaryl;
R$_2$ is C$_1$-C$_6$ alkyl or C$_4$-C$_7$ cycloalkyl, wherein said alkyl or said cycloalkyl is optionally substituted with mono- or di-alkoxy, mono- or di-halophenyl, mono- or di-(C$_{1-4}$) alkoxy phenyl, mono- or di-(C$_{1-4}$)alkyl phenyl, perhalo (C$_{1-4}$)alkyl phenyl, carboxyl, tert-butyl carboxyl, phosphoryl, (C$_{1-6}$)alkyl, (C$_{4-7}$)cycloalkyl, indolyl, isoindolyl, pyridyl, naphthyl, pyrrolyl, imidazolyl, pyrazolyl, pyrimidinyl, pyrazinyl, pyridazinyl, furyl, thienyl, or alkylmorpholino;
R$_3$ and R$_4$ are independently H, C$_1$-C$_6$ alkyl, tert-butyloxycarbonyl (t-Boc), morpholino(C$_1$-C$_4$)alkyl, carboxy (C$_1$-C$_3$)alkyl, (C$_1$-C$_4$)alkoxycarbonyl(C$_1$-C$_3$)alkyl, aryl, heteroaryl, aryloxy, heterocyclyl, cycloalkyl, alkenyl with the proviso that the double bond of the alkenyl is not present at the carbon atom that is directly linked to N, alkynyl with the proviso that the triple bond of the alkynyl is not present at the carbon atom that is directly linked to N, perfluoroalkyl, —S(O)$_2$alkyl, —S(O)$_2$aryl, —(C=O)heteroaryl, —(C=O)aryl, —(C=O)(C$_1$-C$_6$) alkyl, —(C=O)cycloalkyl, —(C=O)heterocyclyl, alkyl-heterocyclyl, aralkyl, arylalkenyl, —CON R$_6$R$_7$, —SO$_2$R$_6$R$_7$, arylalkoxyalkyl, arylalkylalkoxy, heteroarylalkylalkoxy, aryloxyalkyl, heteroaryloxyalkyl, aryloxyaryl, aryloxyheteroaryl, alkylaryloxyaryl, alkylaryloxyheteroaryl, alkylaryloxyalkylamine, alkoxycarbonyl, aryloxycarbonyl, or heteroaryloxycarbonyl;

R$_5$ is H, —OH, halo, optionally monosubstituted (C$_1$-C$_6$) alkyl, optionally monosubstituted (C$_1$-C$_4$)alkoxycarbonyl, optionally monosubstituted (C$_1$-C$_4$)alkanoyl, carbamoyl, optionally monosubstituted (C$_1$-C$_4$)alkyl carbamoyl, phenyl, halophenyl, optionally monosubstituted (C$_1$-C$_4$)alkylphenyl, optionally monosubstituted (C$_1$-C$_4$)alkoxyphenyl, or optionally monosubstituted perhalo(C$_1$-C$_4$)alkylphenyl, wherein said optional substitution is (C$_1$-C$_4$)alkyl, OH, or halogen;

R$_6$ and R$_7$ are independently H, alkyl, aryl, heteroaryl, alkylaryl, arylalkyl, heteroarylalkyl, or alkylheteroaryl.

2. A compound according to claim 1, wherein R$_{1a}$ is phenyl substituted with mono, di, or tri-OH and further substituted with a halo.

3. A compound according to claim 2, wherein said halo is F.

4. A compound according to claim 1, wherein R$_3$ and R$_4$ are H.

5. A compound according to claim 1, wherein R$_5$ is H.

6. A compound according to claim 1, wherein R$_6$ is H and R$_7$ is methyl.

7. A compound according to claim 1, wherein, independently, R$_{1a}$ is phenyl substituted at a meta position with —OH, —CH$_3$, tert-butyl, —CF$_3$ or halo.

8. A compound according to claim 1, wherein, independently, R$_{1a}$ is phenyl substituted at a meta position with halo, (C$_1$-C$_4$)alkyl, haloalkyl, haloaryl, CN, NO$_2$, —C(=O)OH, or —C(=O)O-alkyl.

9. A compound according to claim 1, wherein Z is F, Br, Cl, or I.

10. A compound selected from the group consisting of:
3-(4-amino-7-isopropyl-7H-pyrrolo[2,3-d]pyrimidin-5-yl)-phenol;

3-(7-isopropyl-4-methylamino-7H-pyrrolo[2,3-d]pyrimidin-5-yl)-phenol;
[5-(3-amino-phenyl)-7-isopropyl-7H-pyrrolo[2,3-d]pyrimidin-4-yl]-methyl-amine;
3-(4-benzylamino-7-isopropyl-7H-pyrrolo[2,3-d]pyrimidin-5-yl)-phenol;
3-(4-dibenzylamino-7-isopropyl-7H-pyrrolo[2,3-d]pyrimidin-5-yl)-phenol;
3-[5-(3-hydroxy-phenyl)-4-methylamino-pyrrolo[2,3-d]pyrimidin-7-yl]-propionic acid tert-butyl ester;
3-[5-(3-hydroxy-phenyl)-4-methylamino-pyrrolo[2,3-d]pyrimidin-7-yl]-propionic acid;
3-bromo-5-(7-isopropyl-4-methylamino-7H-pyrrolo[2,3-d]pyrimidin-5-yl)-phenol;
3-(7-isopropyl-4-methylamino-7H-pyrrolo[2,3-d]pyrimidin-5-yl)-5-methyl-phenol;
3-tert-butyl-5-(7-isopropyl-4-methylamino-7H-pyrrolo[2,3-d]pyrimidin-5-yl)-phenol;
3-(7-Isopropyl-4-methylamino-7H-pyrrolo[2,3-d]pyrimidin-5-yl)-5-trifluoromethyl-phenol;
3-bromo-5-(4-chloro-7-isopropyl-7H-pyrrolo[2,3-d]pyrimidin-5-yl)-phenol;
3-(4-chloro-7-isopropyl-7H-pyrrolo[2,3-d]pyrimidin-5-yl)-5-methyl-phenol;
3-tert-butyl-5-(4-chloro-7-isopropyl-7H-pyrrolo[2,3-d]pyrimidin-5-yl)-phenol; and
3-(4-Chloro-7-isopropyl-7H-pyrrolo[2,3-d]pyrimidin-5-yl)-5-trifluoromethyl-phenol or a pharmaceutically-acceptable salt thereof.

11. A pharmaceutical composition, comprising:
a pharmaceutically acceptable carrier, and a compound according to claim 1.

12. A pharmaceutical composition according to claim 11, further comprising at least one anthracycline.

13. A pharmaceutical composition according to claim 12, wherein said anthracycline is daunorubicin, doxorubicin, epirubicin, idarubicin, or a mixture thereof.

14. A compound according to claim 1, wherein $R_{1a}$ is meta-hydroxyphenyl, wherein said phenyl is additionally substituted with at least one of OH, —CN, NO$_2$, —C(=O)OH, —C(=O)O-alkyl, (C$_1$-C$_4$)alkyl, halo, haloalkyl or haloaryl.

* * * * *